US012570663B2

(12) United States Patent
Zhu et al.

(10) Patent No.: US 12,570,663 B2
(45) Date of Patent: Mar. 10, 2026

(54) CRYSTAL FORMS OF AN ANTI-SARS CoV-2 AGENT

(71) Applicant: Enanta Pharmaceuticals, Inc., Watertown, MA (US)

(72) Inventors: Kaicheng Zhu, Belmont, MA (US); Tao Wang, Berkeley Heights, NJ (US); Joseph Helble, Hudson, MA (US); Anthony Toto, Boonton Township, NJ (US); Jiajun Zhang, Cambridge, MA (US); George G. Wu, Waltham, MA (US); Yat Sun Or, Waltham, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 342 days.

(21) Appl. No.: 18/377,105

(22) Filed: Oct. 5, 2023

(65) Prior Publication Data

US 2024/0132512 A1 Apr. 25, 2024

Related U.S. Application Data

(60) Provisional application No. 63/413,850, filed on Oct. 6, 2022.

(51) Int. Cl.

| | |
|---|---|
| ***C07D 487/20*** | (2006.01) |
| ***A61K 31/407*** | (2006.01) |
| ***C07D 487/10*** | (2006.01) |

(52) U.S. Cl.

CPC .......... *C07D 487/10* (2013.01); *A61K 31/407* (2013.01); *C07B 2200/13* (2013.01)

(58) Field of Classification Search

None

See application file for complete search history.

(56) References Cited

U.S. PATENT DOCUMENTS

| | | | |
|---|---|---|---|
| 8,546,416 | B2 | 10/2013 | Ambarkhane et al. |
| 11,352,363 | B1 | 6/2022 | Wang et al. |

(Continued)

FOREIGN PATENT DOCUMENTS

| | | | |
|---|---|---|---|
| WO | 2005113580 | A1 | 12/2005 |
| WO | 2006061714 | A3 | 8/2006 |

(Continued)

OTHER PUBLICATIONS

Pubchem, SID 367622864, May 25, 2018.

(Continued)

*Primary Examiner* — Jeffrey S Lundgren
*Assistant Examiner* — Sara Elizabeth Townsley
(74) *Attorney, Agent, or Firm* — Edgar W. Harlan; Carolyn S. Elmore; Elmore Patent Law Group, P.C.

(57) ABSTRACT

The present invention features crystalline forms of Compound I,

Compound I (Continued)

including polymorphs and pseudopolymorphs, which are useful in the preparation of pharmaceutical compositions.

14 Claims, 34 Drawing Sheets

(56) References Cited

U.S. PATENT DOCUMENTS

| | | | |
|---|---|---|---|
| 11,384,090 | B2 | 7/2022 | Wang et al. |
| 11,858,945 | B2 | 1/2024 | Panarese et al. |
| 11,912,714 | B2 | 2/2024 | Cao et al. |
| 11,919,910 | B2 | 3/2024 | Wang et al. |
| 2006/0014821 | A1 | 1/2006 | He et al. |
| 2023/0103494 | A1 | 4/2023 | Wang et al. |
| 2023/0174542 | A1 | 6/2023 | Panarese et al. |
| 2023/0295175 | A1 | 9/2023 | Zhu et al. |
| 2023/0331734 | A1 | 10/2023 | Cao et al. |
| 2024/0132512 | A1 | 4/2024 | Zhu et al. |
| 2024/0327334 | A1 | 10/2024 | Gao et al. |

FOREIGN PATENT DOCUMENTS

| | | | |
|---|---|---|---|
| WO | 2013049382 | A1 | 5/2013 |
| WO | 2018042343 | A2 | 3/2018 |
| WO | 2021226546 | A1 | 11/2021 |
| WO | 2021250648 | A1 | 12/2021 |
| WO | 2021252644 | A1 | 12/2021 |
| WO | 2022159644 | A1 | 7/2022 |
| WO | 2022235605 | A1 | 11/2022 |
| WO | 2023086350 | A1 | 5/2023 |
| WO | 2023109926 | A1 | 6/2023 |
| WO | 2024076680 | A1 | 4/2024 |

OTHER PUBLICATIONS

Anonymous, "Nirmatrelvir", Cortellis Database, Retrieved from the Internet:URL:https://www.cortellis.com/drugdiscovery/entity/drug/1126756/product?ent=qR5ruNw5&updateHistoryPage=5&orderBy=_ score:desc, Nov. 8, 2022, 3 pgs.

Anonymous, "Pfizer Initiates Phase 1 Study of Novel Oral Antiviral Therapeutic Agent Against SARS-CoV-2 Science Products Stories Newsroom About", Retrieved from the Internet: URL:https://www.pfizer.com/news/press-release/press-release-detail/pfizer-initiatesphase-1-study-novel-oral-antiviral [retrieved on Nov. 11, 2022].

Chen, L., "Design, Synthesis, Characterization, and Biological Activities of Novel Spirooxindole Analogues Containing Hydantoin, Thiohydantoin, Urea, and Thiourea Moieties", J. Agric. Food Chem., 68(39), https://doi.org/10.1021/acs.jafc.0c04488, Aug. 31, 2020, 10618-10625.

Chia, C.S. Brian, "Novel Coronavirus Main Protease Di- and Tripeptide Inhibitors for Treating COVID-19", ACS Med. Chem. Lett., 13(9), URL:https://pubs.acs.org/doi/pdf/10.1021/acsmedchemlett.2c00332, Aug. 8, 2022, 1388-1389.

Dai, W., "Structure-based design of antiviral drug candidates targeting the SARS-CoV-2 main protease", Science, 368(6497), DOI: 10.1126/science. abb4489, Jun. 19, 2020, 1331-1335.

Owen, D., "Oral inhibitors of the SARS-CooV-2 main protease for the treatment of COVID-19", 261ST Am. Chem. Soc. (ACS) Natl Meet (virtual), Apr. 16, 2021, 1 pg.

Wang, Y., "Inhibition of Enterovirus 71 Replication by an a-Hydroxy-Nitrile Derivative NK-1.9k", Antiviral Res., 141, DOI: 10.1016/J.ANTIVIRAL.2017.01.002, Jan. 5, 2017, 91-100.

Zhai, Y., "Cyanohydrin as an Anchoring Group for Potent and Selective Inhibitors of Enterovirus 71 3C Protease", J. Med. Chem., 58(23), DOI: 10.1021/acs.jmedchem.5b01013, Dec. 10, 2015, 9414-9420.

CRYSTAL FORMS OF AN ANTI-SARS CoV-2 AGENT

RELATED APPLICATION

This application claims the benefit of U.S. Provisional Application No. 63/413,850, filed on Oct. 6, 2022. The entire teachings of the above application are incorporated herein by reference.

FIELD OF THE INVENTION

The present invention relates to crystalline polymorphic forms of novel Compound I, process for their preparation, pharmaceutical compositions comprising the polymorphic forms, methods of using the same to prepare pharmaceutical compositions, and methods of using the polymorphic forms to treat or prevent a coronavirus infection.

BACKGROUND

Coronaviruses are enveloped, positive-sense, single-stranded RNA viruses. The genomic RNA of CoVs has a 5'-cap structure and 3'-poly-A tail and contains at least 6 open reading frames (ORFs). The first ORF (ORF 1a/b) directly translates two polyproteins: pp1a and pp1ab. These polyproteins are processed by a 3C-Like protease (3CLpro), also known as the main protease (Mpro), into 16 non-structural proteins. These non-structural proteins engage in the production of subgenomic RNAs that encode four structural proteins, namely envelope, membrane, spike, and nucleocapsid proteins, among other accessory proteins. As a result, it is understood that 3C-Like protease has a critical role in the coronavirus life cycle.

3CLpro is a cysteine protease involved in most cleavage events within the precursor polyprotein. Active 3CLpro is a homodimer containing two protomers and features a Cys-His dyad located in between domains I and II. 3CLpro is conserved among coronaviruses and several common features are shared among the substrates of 3CLpro in different coronaviruses. As there is no human homolog of 3CLpro, it is an ideal antiviral target. Although compounds have been reported to inhibit 3CLpro activity, they have not been approved as coronavirus therapies. (Refer to WO 2004101742 A2, US 2005/0143320 A1, US 2006/0014821 A1, US 2009/0137818 A1, WO 2013/049382 A2, WO 2013/166319 A1, WO2018042343, WO2018023054, WO 2022013684, WO 2021252644, WO2022020711, WO 2022020242, U.S. Pat. No. 11,174,231 B1, U.S. Pat. No. 11,124,497 B1, WO2005113580, and WO2006061714).

There is a need for novel therapeutic agents that treat, ameliorate or prevent SARS-CoV-2 infection.

SUMMARY OF THE INVENTION

The present invention provides polymorphic and pseudopolymorphic forms of Compound I [Chemical name: N—((S)-1-((3R,5'S)-5'-cyano-2-oxospiro[indoline-3,3'-pyrrolidin]-1'-yl)-4-methyl-1-oxopentan-2-yl)-4,6,7-trifluoro-N-methyl-1H-indole-2-carboxamide], which has the structure below.

Compound I

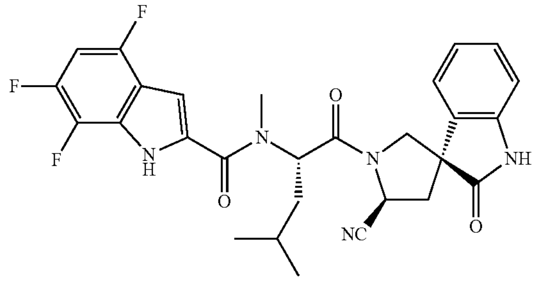

In certain embodiments, the invention provides Compound I in a polymorphic or pseudopolymorphic form as disclosed herein.

In certain embodiments, the invention provides methods of producing the polymorphs and pseudopolymorphs of Compound I disclosed herein.

In certain embodiments, the invention provides compositions comprising a polymorph or pseudopolymorph of Compound I disclosed herein. In certain embodiments, the composition is a pharmaceutical composition comprising at least one polymorph or pseudopolymorph of Compound I and a pharmaceutically acceptable carrier or excipient. In certain embodiments, the composition is substantially free of other polymorphs or pseudopolymorphs of Compound I.

In certain embodiments, the invention provides a method of treating or preventing a coronavirus infection in a subject in need thereof. The method comprises the step of administering to the subject (a) a therapeutically effective amount of a polymorph or pseudopolymorph of Compound I, (b) a therapeutically effective amount of two or more polymorph or pseudopolymorph forms of Compound I, or (c) a therapeutically effective amount of one or more polymorphs and/or pseudopolymorphs of Compound I and an amorphous form of Compound I.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
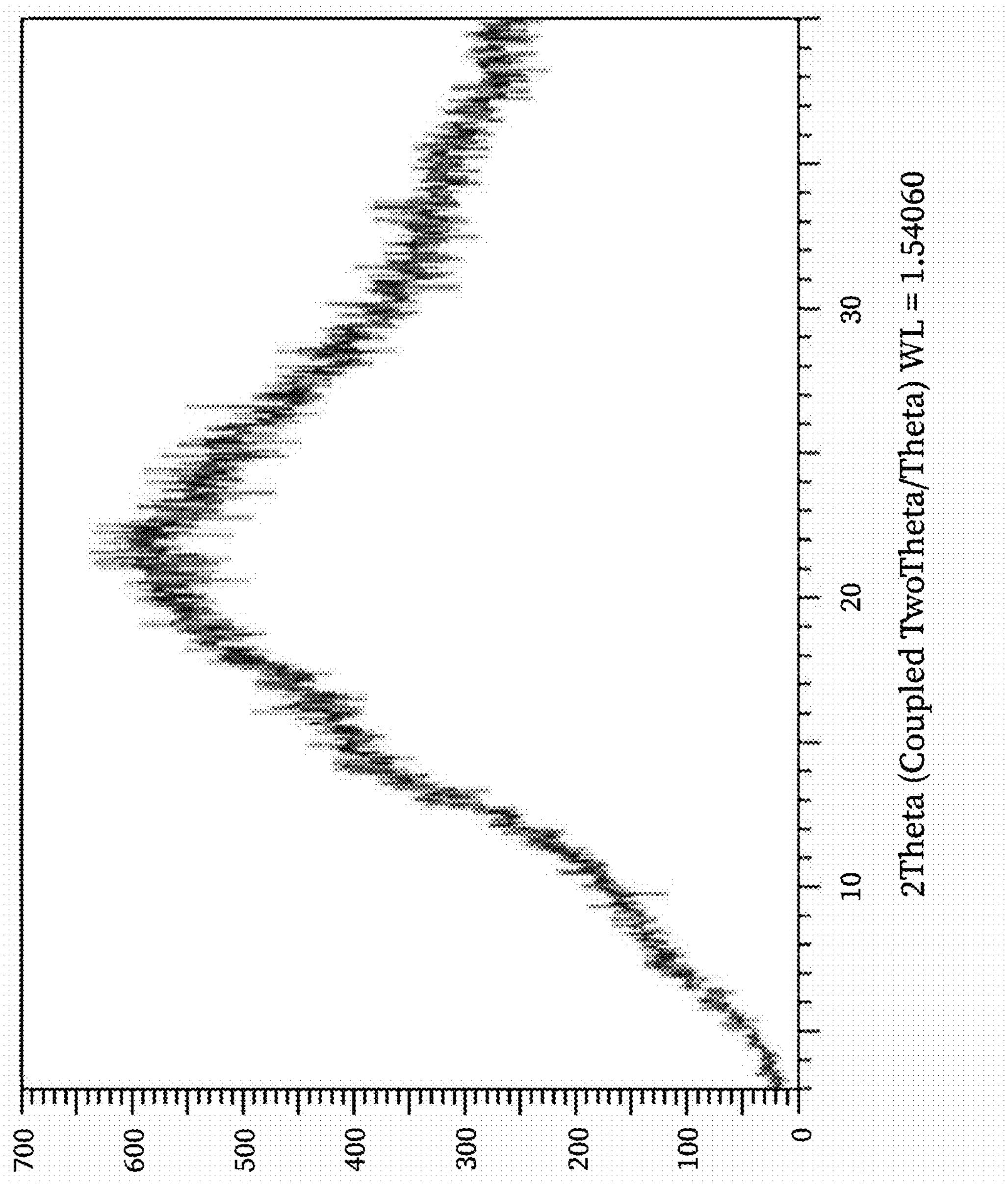
FIG. 1 is the x-ray powder diffraction (XRPD) pattern of the amorphous form of Compound I.
Figure 2:
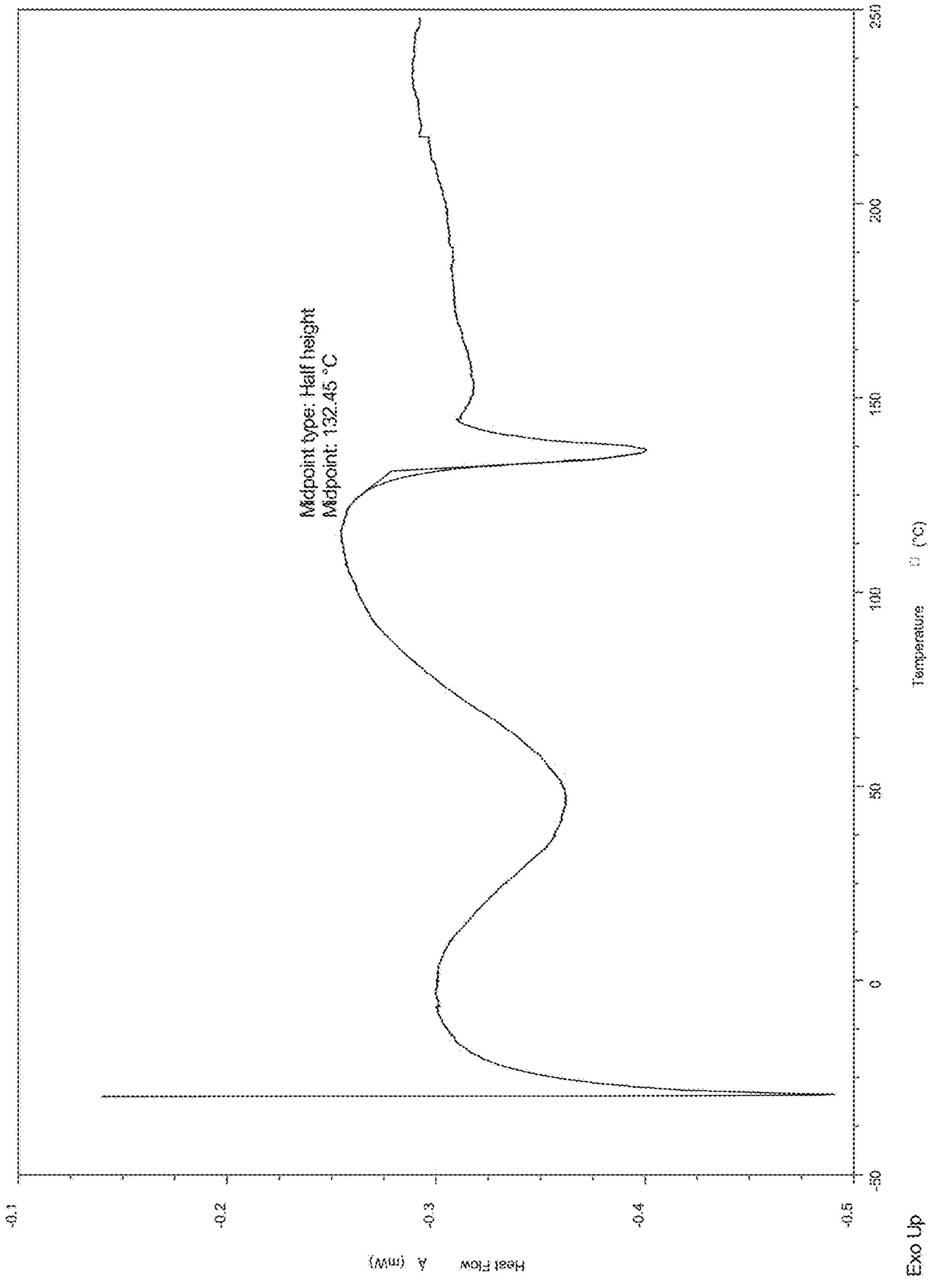
FIG. 2 is the Differential Scanning calorimetry (DSC) thermogram of the amorphous form of Compound I.

Compound I is a potent 3CL Protease protein inhibitor and is described in patent application WO 2022/109363, the contents of which are incorporated herein by reference in their entirety. Compound I is a single enantiomer with three chiral centers. The method for preparing Compound I disclosed in WO 2022/109363 yields the amorphous form of Compound I disclosed herein. Summaries of the procedures for generating four polymorphic forms (Forms 1, 2, 3, 4), a mixture of Form 2 and Form 4, and ten pseudopolymorphic forms (Forms A, B, C, D, E, F, G, H, H1, J) are listed in Table 1.

TABLE 1

Procedures for preparing polymorphs and pseudopolymorphs of Compound I.

| Polymorph or pseudo-polymorph | Preparation procedure |
|---|---|
| Form 1 | A clear solution of Form D in ethanol was added to water to provide Form 1 |
| Form 2 | Form J was heated to 155° C. and cooled to provide Form 2 |
| Form 3 | Form J was heated to 80° C. and cooled to provide Form 3 |
| Form 4 | Form J was heated to 60° C. and cooled to provide Form 4 |
| Mixture of Form 2 and Form 4 | Form J was heated to 125° C., and cooled to provide a mixture of Form 2 and Form 4 |

TABLE 1-continued

Procedures for preparing polymorphs and pseudopolymorphs of Compound I.

| Polymorph or pseudo-polymorph | Preparation procedure |
|---|---|
| Form A | Amorphous Compound I was equilibrated in mixed benzyl alcohol and toluene under temperature cycles to provide Form A |
| Form B | Amorphous Compound I was equilibrated in anisole under temperature cycles to provide Form B |
| Form C | A clear solution of amorphous Compound I in anisole was slow evaporated to provide for Form C |
| Form D | Form A was equilibrated in mixed acetone and water to provide Form D |
| Form E | Form D was equilibrated in mixed dimethyl sulfoxide and water under temperature cycles to provide Form E |
| Form F | Form D was equilibrated in mixed PEG and water under temperature cycles to provide Form F |
| Form G | Form D was equilibrated in mixed methyl ethyl ketone and water under temperature cycles to provide Form G |
| Form H | Form D was equilibrated in mixed isopropyl alcohol and water under temperature cycles to provide Form H |
| Form H1 | Form H was stored at room temperature to provide Form H1 |
| Form J | Heptane was added to a clear solution of Form 1 in tetrahydrofuran solution to provide Form J |

All polymorphs and pseudopolymorphs were proved to be identical in solution as evidenced by proton Nuclear Magnetic Resource ($^1H$ NMR). Solid-state techniques such as Differential Scanning calorimetry (DSC), Fourier-transform infrared spectroscopy (FT-IR), and Powder X-Ray Diffractometry (XRD) revealed the differences among those forms. The current synthetic process produces the drug substance as an anhydrous, unsolvated amorphous solid, which is stable under the storage conditions described in this application.

In one embodiment, the present invention provides four polymorphic forms (Forms 1, 2, 3, 4), a mixture of Form 2 and Form 4, and ten pseudopolymorphs (Forms A, B, C, D, E, F, G, H, H1, J), which are characterized by differential scanning calorimetry (DSC). The DSC thermal characteristics of the polymorph forms and pseudopolymorph forms are described in FIG. 4, FIG. 8, FIG. 10, FIG. 14, FIG. 16, FIG. 18, FIG. 21, FIG. 24, FIG. 27, FIG. 29, FIG. 33, and in Table 2 and Table 3.

TABLE 2

The thermal events (exotherms or endotherms) and relevant temperatures of polymorphic Forms 1, 2, 3, and 4 and a mixture of Forms 2 and 4

| Form | Thermal Event | FIG. No. |
|---|---|---|
| Form 1 | 251° C. (endotherm) | FIG. 4 |
| Form 2 | 175° C. (exotherm) | FIG. 8 |
| | 251° C. (endotherm) | |
| Form 3 | 150° C. (endotherm) | FIG. 10 |
| | 176° C. (exotherm) | |
| | 251° C. (endotherm) | |
| Mixture of Form 2 and Form 4 | 139° C. (endotherm) | FIG. 14 |
| | 147° C. (endotherm) | |
| | 176° C. (exotherm) | |
| | 250° C. (endotherm) | |

TABLE 3

The thermal events (exotherms or endotherms) and relevant temperatures of polymorph of Forms A, B, D, E, F, G, H, and J

| Form | Thermal Event | FIG. No. |
|---|---|---|
| Form A | 109° C. (endotherm) | FIG. 16 |
| Form B | 108° C. (endotherm) | FIG. 18 |
| Form D | 118° C. (endotherm) | FIG. 21 |
| Form E | 142° C. (endotherm) | FIG. 24 |
| Form G | 130° C. (endotherm) | FIG. 27 |
| Form H | 74° C. (endotherm) | FIG. 29 |
| | 157° C. (endotherm) | |
| Form J | 110° C. (endotherm) | FIG. 33 |
| | 133° C. (endotherm) | |
| | 169° C. (exotherm) | |
| | 250° C. (endotherm) | |

In one embodiment, the present invention provides four polymorphs (Forms 1, 2, 3, 4), a mixture of Form 2 and Form 4, and ten pseudopolymorphs (Forms A, B, C, D, E, F, G, H, H1, J), which are further characterized by powder X-ray diffraction (XRPD). The characteristic powder diffraction peaks are expressed in degrees 2θ. The positions of the peaks (2θ) for all the forms are different to each other. The position of intense peaks of the polymorph forms and pseudopolymorph forms are presented in Table 4 and Table 5. The relative intensity, as well as the position of intense peaks in FIG. 3, FIG. 7, FIG. 9, FIG. 12, FIG. 13, FIG. 15, FIG. 17, FIG. 19, FIG. 20, FIG. 23, FIG. 25, FIG. 26, FIG. 28, FIG. 30, and FIG. 32 may change or shift under certain conditions, although the crystalline form is the same. One of ordinary skill in the art is able to readily determine whether a given polymorph Form is the same polymorph Form as described in one of FIG. 3, FIG. 7, FIG. 9, FIG. 12, FIG. 13, FIG. 15, FIG. 17, FIG. 19, FIG. 20, FIG. 23, FIG. 25, FIG. 26, FIG. 28, FIG. 30, FIG. 32, Table 4 or Table 5 by comparing their peak positions and intensities in the XRPD data.

The powder X-ray diffractograms of the crystalline polymorphic and pseudopolymorphic forms, and the mixture were found to be different from each other.

TABLE 4

The position (2θ) of intense peaks for polymorph of Forms 1, 2, 3, 4 and mixture of Form 2 and Form 4.

| Form 1 (FIG. 3) | Form 2 (FIG. 7) | Form 3 (FIG. 9) | Form 4 (FIG. 12) | Mixture of Form 2 and Form 4 (FIG. 13) |
|---|---|---|---|---|
| | | | | 4.36 |
| | | | 4.39 | |
| | | | 5.14 | |
| | | | | 6.87 |
| 6.88 | 6.88 | | | |
| | | | 7.06 | 7.06 |
| | | 7.10 | | |
| | | | 7.50 | |
| 8.32 | | | | |
| | | | | 8.46 |
| | | | 8.47 | 8.71 |
| | | 8.71 | | |
| | | 8.92 | 8.92 | 8.92 |
| | | | 9.75 | |
| | | | | 9.77 |
| | | | 10.08 | |
| | | | 10.33 | |
| | | | | 10.80 |
| 10.82 | 10.82 | | | |
| | | 11.03 | 11.03 | |
| | | | | 11.04 |
| | | 11.70 | | |
| | | 11.71 | | |
| | | | | 11.72 |
| | | | | 11.89 |
| 11.90 | 11.90 | | | |
| | | | | 12.43 |
| | | 12.45 | | |
| | | | | 12.58 |
| | | 13.07 | | |
| | | | 13.09 | |
| 13.15 | | | | |
| | | | | 13.73 |
| | | | 13.83 | |
| | | 14.06 | 14.06 | 14.06 |
| 13.74 | 13.74 | | | |
| | | | | 14.53 |
| 14.54 | 14.54 | | | |
| | | | 14.62 | |
| | | | 14.84 | |
| | | 15.23 | | |
| | | | 15.38 | |
| 15.41 | | | | |
| | | 15.55 | | |
| | | | 15.78 | |
| | | | | 15.81 |
| | | | 15.95 | |
| | | | | 16.07 |
| | 16.08 | | | |
| 16.09 | | | | |
| | | 16.17 | | |
| | | | 16.91 | |
| | | 17.14 | | |
| | | 17.45 | 17.45 | |
| | | | 17.93 | |
| | | 17.96 | | |
| | | | | 18.08 |
| | 18.10 | | | |
| 18.19 | | | | |
| | | | 18.54 | |
| | | | | 18.55 |
| | | 19.16 | | |
| 19.19 | | | | |
| | | | 19.23 | |
| | | 19.56 | | |
| | | | 19.66 | |
| | | | | 20.03 |
| 20.04 | 20.04 | | | |
| | | | 20.07 | |
| | | 20.43 | | |
| 20.56 | 20.56 | | | 20.56 |
| | | 20.68 | | |
| | | | 20.96 | |
| | | | | 21.06 |
| | 21.68 | | | 21.68 |
| 21.69 | | | | |
| | | | 21.84 | |
| | | | | 21.87 |
| | | 21.89 | | |
| 22.29 | 22.29 | | | |
| | | | | 22.30 |
| | | | 22.50 | |
| | | 22.56 | | |
| | | | | 22.58 |
| | | | 23.42 | |
| | | | | 23.44 |
| | | 23.45 | | |
| | | 23.83 | | |
| | | | | 23.86 |

TABLE 4-continued

| The position (2θ) of intense peaks for polymorph of Forms 1, 2, 3, 4 and mixture of Form 2 and Form 4. | | | | |
|---|---|---|---|---|
| Form 1 (FIG. 3) | Form 2 (FIG. 7) | Form 3 (FIG. 9) | Form 4 (FIG. 12) | Mixture of Form 2 and Form 4 (FIG. 13) |
| 23.87 | 23.87 | | | |
| | | | 24.19 | 24.21 |
| | | 24.74 | | |
| | | | | 24.79 |
| | 24.80 | | | |
| 24.83 | | | | |
| | | | 24.91 | |
| | | | 25.13 | |
| | 25.18 | | | 25.18 |
| 25.19 | | | | |
| 25.31 | | | | |
| | | 25.79 | | |
| | | | | 26.11 |
| | 26.12 | | | |
| 26.13 | | | | |
| | | | 26.18 | |
| | | 26.26 | | |
| | | | 26.54 | |
| 26.66 | | | | 26.66 |
| | 26.67 | | | |
| | | 26.95 | | |
| 27.63 | | | | |
| | | | 27.81 | |
| | | | | 27.90 |
| 27.92 | | | | |
| | 27.93 | | | |
| | | 28.12 | | |
| | | | 28.54 | |
| | | 28.64 | | |
| | 28.77 | | | |
| 28.90 | | | | |
| | 29.23 | | | |
| 29.29 | | | | |
| | | | 29.41 | |
| | | 29.68 | | |
| | | | | 30.11 |
| | 30.13 | | | |

TABLE 4-continued

| The position (2θ) of intense peaks for polymorph of Forms 1, 2, 3, 4 and mixture of Form 2 and Form 4. | | | | |
|---|---|---|---|---|
| Form 1 (FIG. 3) | Form 2 (FIG. 7) | Form 3 (FIG. 9) | Form 4 (FIG. 12) | Mixture of Form 2 and Form 4 (FIG. 13) |
| 30.14 | | | | |
| | | 30.44 | | |
| | | | 30.99 | |
| | 31.25 | | | 31.25 |
| | | 31.28 | | |
| 31.32 | | | | |
| | | | | 31.72 |
| 31.74 | | | | |
| | | 31.76 | | |
| | 32.84 | | | |
| | | 32.34 | | |
| 32.48 | | | | |
| | | 32.79 | | |
| 32.86 | | | | |
| | | | | 32.88 |
| | | 33.30 | | |
| | 34.28 | | | |
| 34.66 | 34.66 | | | |
| | | 34.67 | | |
| 34.95 | | | | |
| | | 35.56 | | |
| | 35.71 | | | |
| | | | | 35.72 |
| 35.75 | | | | |
| | 36.07 | | | |
| 36.11 | | 36.11 | | |
| | | 36.47 | | |
| 36.79 | | | | |
| | | 37.07 | | |
| | 37.10 | | | |
| 37.12 | | | | |
| 37.79 | | | | |
| | | 37.85 | | |
| | | 38.22 | | |
| 38.76 | | | | |
| | 39.66 | | | |
| 39.74 | | | | |

TABLE 5

| The position (2θ) of intense peaks for polymorph of Forms A, B, C, D, E, F, G, H, H1, and J. | | | | | | | | | |
|---|---|---|---|---|---|---|---|---|---|
| Form A (FIG. 15) | Form B (FIG. 17) | Form C (FIG. 19) | Form D (FIG. 20) | Form E (FIG. 23) | Form F (FIG. 25) | Form G (FIG. 26) | Form H (FIG. 28) | Form H1 (FIG. 30) | Form J (FIG. 32) |
| | | | | | | | 3.83 | | |
| | | | | | | | | 3.91 | |
| | | | | | | 4.18 | | | |
| | | | | | | | | | 4.36 |
| | | 4.99 | | | | | | | |
| | | | | 5.85 | | | | | |
| | | 6.01 | | | | | | | |
| | | | | | | | | 6.45 | |
| | | 6.72 | | | | | | | |
| | | | | | | 6.86 | | | |
| | | | | | 6.87 | | | | |
| | | | | | | | | | 6.92 |
| 6.96 | | | | | | | | | |
| | | | | | | | | | 7.05 |
| | | | | | | | | 7.08 | |
| | | | 7.10 | | | | | | |
| | 7.17 | | | | | | | | |
| | | | | | | | 7.04 | | |
| | | | | | | | | | 7.44 |
| | | | | | | | | 7.58 | |
| | | | | | | | 7.61 | | |
| | | | | | | | 7.79 | | |
| | | 7.83 | | | | | | | |

TABLE 5-continued

The position (2θ) of intense peaks for polymorph of Forms A, B, C, D, E, F, G, H, H1, and J.

| Form A (FIG. 15) | Form B (FIG. 17) | Form C (FIG. 19) | Form D (FIG. 20) | Form E (FIG. 23) | Form F (FIG. 25) | Form G (FIG. 26) | Form H (FIG. 28) | Form H1 (FIG. 30) | Form J (FIG. 32) |
|---|---|---|---|---|---|---|---|---|---|
| | | | | | | | | 7.90 | |
| | | | 7.99 | | | | | | |
| 8.05 | | | | | | | | | |
| | | | | | | | | 8.14 | |
| | | | | | | | | | 8.21 |
| | | | 8.27 | | | | | | |
| | | | | | | 8.35 | | | |
| | | | | | | | | | 8.45 |
| | | | | 8.52 | | | | | |
| | | 8.70 | | | | | | | |
| | | | | | | | 8.94 | | |
| | | | 8.98 | | | | | | |
| | | | | | | 9.03 | | | |
| | | | | 9.26 | | | | 9.28 | |
| | | 9.33 | | | | | | | |
| | | | | | | | 9.37 | | |
| | | | | | | 9.44 | | | |
| | | | | | | | | | 9.47 |
| | | | | | | | | 9.76 | 9.76 |
| | | | 9.89 | | | | | | |
| | | | | | | | | | 10.22 |
| | | | | | | | | 10.32 | |
| | | | | | | 10.34 | | | |
| | | 10.68 | | | | | | 10.68 | |
| | | | | | | | | | 10.80 |
| | | 10.98 | | | | | | | |
| | | | | 11.08 | | 11.08 | | | |
| | | | | | | | | | 11.26 |
| | | | | | | 11.39 | | | |
| | | | | | | | 11.46 | | |
| | | | | | | | | | 11.49 |
| | | 11.66 | | | | | | 11.63 | |
| | | | | | | | 11.68 | | |
| | | | 11.88 | | | | | | |
| | | 11.90 | | | | | | | |
| | | | | | | | | | 12.02 |
| | | | | | | | 12.32 | | |
| | | | | | | | | | 12.41 |
| | | | | | | | | 12.51 | |
| | | | | | | 12.53 | | | |
| | | | | 12.69 | | | | | |
| | | | | | | | 12.81 | | |
| | | | | | | 12.86 | | | |
| | | | | | | | | | 12.90 |
| | | 12.96 | | | | | | | |
| | | | | 12.95 | | | | 12.95 | |
| 13.00 | | | | | | | | | |
| | | | | | 13.07 | | | | |
| | | | 13.14 | | | | | | |
| | | | | | | | 13.21 | | |
| | | | | 13.22 | | | | | |
| | | | 13.27 | | | | | 13.27 | |
| | | | | | | 13.28 | | | |
| | | 13.43 | | | | | | | |
| | | | | | | | | | 13.48 |
| | | | | | | 13.52 | | | |
| | | 13.71 | | | | | | | |
| | | | | | | | 13.74 | | 13.74 |
| 13.97 | | | | | | | | | |
| | | 14.01 | | | | | | | |
| | | | | | | | 14.06 | | |
| | | | | | | | | | 14.09 |
| | | | 14.16 | | | | | 14.15 | |
| | | | | | | 14.31 | | | |
| | 14.33 | | | | | | | | |
| | | | | | | | | | 14.53 |
| | | | | | | | 14.56 | | |
| | | | | 14.71 | | | | | |
| | | | | | | 14.75 | | | |
| | | | | | | | | 14.78 | |
| | | | | | | | 14.80 | | |
| | | | | | | | | | 14.82 |
| | | 14.92 | | | | | | | |
| | | | | 15.01 | | | | | |
| | | | | | | | | 15.12 | |

TABLE 5-continued

The position (2θ) of intense peaks for polymorph of Forms A, B, C, D, E, F, G, H, H1, and J.

| Form A (FIG. 15) | Form B (FIG. 17) | Form C (FIG. 19) | Form D (FIG. 20) | Form E (FIG. 23) | Form F (FIG. 25) | Form G (FIG. 26) | Form H (FIG. 28) | Form H1 (FIG. 30) | Form J (FIG. 32) |
|---|---|---|---|---|---|---|---|---|---|
| | | | | | | 15.14 | 15.14 | | |
| | | 15.19 | | | | | | | |
| | | | | | | | | 15.24 | |
| | | | | | | | 15.47 | | |
| | | 15.53 | | | | | | | |
| | | | | | | | | | 15.63 |
| | | | | | | 15.73 | | | |
| | | | | | | | | | 15.78 |
| | | | | | | | | 15.86 | |
| | | | | | | | 15.93 | | |
| | | | | 16.01 | | | | | |
| | | | | | | | | | 16.07 |
| | | | | | | | 16.15 | | |
| | | | 16.21 | | | | | | |
| | | | | | | 16.22 | | | |
| | | 16.28 | | | | | | | |
| | | | | | | | | | 16.41 |
| | | | | | | | | 16.57 | |
| | | | | | | | | | 16.61 |
| | | | | | | | 16.63 | | |
| | | | | | | 16.72 | | | |
| | | | | 16.83 | | | | | |
| | | | | | | 16.96 | | | |
| | | | | 17.04 | | | | | |
| | | | | | | | 17.17 | | |
| | | | | | | | 17.44 | | |
| | | | | | | 17.48 | | | |
| | | | 17.55 | | | | | | |
| | | | | 17.56 | | | | 17.56 | |
| | | | | | | | | | 17.60 |
| | | | | | | 17.62 | | | |
| | | 17.73 | | | | | | | |
| | | | | | | | | | 17.95 |
| | | | | | | 17.97 | | | |
| | | | | | | | | 17.98 | |
| | | | | | | | 18.01 | | |
| | | | | | | | | | 18.20 |
| | | 18.22 | | | | | | | |
| | | | | | | | | 18.43 | |
| | | | 18.45 | | | | | | |
| | | | | 18.54 | | | | | |
| | | | | | | | 18.64 | | 18.64 |
| | | | | | | | | 18.67 | |
| | | | | | | 18.75 | | | |
| | | | 18.77 | | | | | | |
| | | | | 18.83 | | | | | |
| | | 18.96 | | | | | | | |
| | | | | | | | 19.03 | | |
| | | | | | | 19.08 | | | |
| | | | | | | | 19.13 | | 19.13 |
| | | | | 19.18 | | | | | |
| | | | | | | | | 19.41 | |
| | | | | | | | | | 19.43 |
| | | | | | | | 19.59 | | |
| | | | | | | 19.68 | | | |
| | | | | | | | | | 19.72 |
| | | | | 19.73 | | | | | |
| | | | | | | | | | 20.03 |
| | | | | | | 20.16 | | | |
| | | | | 20.19 | | | | | |
| | | | | | | | | 20.25 | |
| | | | | | | | | | 20.26 |
| | | | | | | | | | 20.36 |
| | | 20.44 | | | | | | | |
| | | | | | | | 20.46 | | |
| | | | | | | | | | 20.51 |
| | | | | | | 20.60 | | | |
| | | | | | 20.63 | | | | |
| | | | | | | | | 20.79 | |
| | | | | | | | 20.82 | | |
| | | | | 20.83 | | | | | |
| | | | | | | 20.90 | | | |
| | | | 20.97 | | | | | | |
| 21.03 | | | | | | | | | |
| | | | | 21.09 | | | | | |

TABLE 5-continued

The position (2θ) of intense peaks for polymorph of Forms A, B, C, D, E, F, G, H, H1, and J.

| Form A (FIG. 15) | Form B (FIG. 17) | Form C (FIG. 19) | Form D (FIG. 20) | Form E (FIG. 23) | Form F (FIG. 25) | Form G (FIG. 26) | Form H (FIG. 28) | Form H1 (FIG. 30) | Form J (FIG. 32) |
|---|---|---|---|---|---|---|---|---|---|
| | | 21.11 | | | | | | | 21.11 |
| | | | | | | 21.13 | | | |
| | | | | | | | 21.21 | | |
| | | | | | | | | 21.25 | |
| | | | 21.32 | | | | | | |
| | | | | 21.38 | | | | | |
| | | | | | | | | 21.42 | |
| | 21.55 | | | | | | | | |
| | | | | | | | | 21.74 | |
| | | | 21.79 | | | | | | |
| | | | | | | | | | 21.87 |
| | | 21.99 | | 21.99 | | | | | |
| | | | | | | 22.02 | | | |
| | | | | | | | 22.20 | | |
| | | | | | | | | | 22.32 |
| | | | | | | 22.39 | | | |
| | | | | 22.67 | | | | | |
| | | | | | | | | 22.93 | |
| | | | | | | | | | 22.97 |
| | | | | | | 23.01 | | | |
| | | | | | | | 23.02 | | |
| | | | | | | | | | 23.07 |
| | | 23.09 | | | | | | | |
| | | | 23.11 | | | | | | |
| | | | | 23.19 | | | | | |
| | | | | | | | 23.22 | | |
| | | | | | | | | | 23.35 |
| | | | | | | | | 23.36 | |
| | | | | | | 23.38 | | | |
| | | | | | | | 23.56 | | |
| | | | | | | 23.57 | | | |
| | | | | 23.77 | | | | | |
| | | | | | | | 23.80 | | 23.80 |
| | | | | | | | | 23.86 | |
| | | | | | | 23.98 | | | |
| | | 24.06 | | | | | | | |
| | | | | | | | | 24.09 | |
| | | | | | | | 24.14 | | 24.14 |
| | | | | | | 24.31 | | | |
| | | | | | | 24.64 | | | |
| | | | | 24.67 | | | | | |
| | | | | | | | | 24.69 | |
| | | | 24.72 | | | | | | |
| | | | | | | | | | 24.75 |
| | | | | | | | | | 24.99 |
| | | | | | | 25.07 | | | |
| | | | | 25.10 | | | | | |
| | | | | | | | | | 25.16 |
| | | 25.33 | | | | | | | |
| | | | | | | 25.38 | | | |
| | | | | | | | | 25.40 | |
| | | | | | | | | | 25.42 |
| | | | | 25.84 | | 25.84 | | | |
| | | | | | | | 25.85 | | |
| | | 25.86 | | | | | | | |
| | | | | | | | | | 26.11 |
| | | | | | | | | 26.24 | |
| | | | | | | 26.63 | | | |
| | | | | 26.68 | | | | | |
| | | | | | | | | | 26.69 |
| | | | 26.71 | | | | | | |
| | | | | | | | 26.76 | | |
| | | | | | | | | 26.94 | |
| | | | | | | | 26.96 | | |
| | | | | | | | | | 27.12 |
| | | | | | | 27.21 | | | |
| | | | | | | | | 27.24 | |
| | | | | 27.40 | | | | | |
| | | | | | | | | | 27.42 |
| | | | | | | | 27.56 | | |
| | | | | 27.69 | | | | | |
| | | | 27.72 | | | | | | |
| | | | | | | | | | 27.89 |
| | | 27.91 | | | | | | | |
| | | | | | | | | 28.16 | |

TABLE 5-continued

| The position (2θ) of intense peaks for polymorph of Forms A, B, C, D, E, F, G, H, H1, and J. | | | | | | | | | |
|---|---|---|---|---|---|---|---|---|---|
| Form A (FIG. 15) | Form B (FIG. 17) | Form C (FIG. 19) | Form D (FIG. 20) | Form E (FIG. 23) | Form F (FIG. 25) | Form G (FIG. 26) | Form H (FIG. 28) | Form H1 (FIG. 30) | Form J (FIG. 32) |
| | | | | | | 28.29 | | | |
| | | | | 28.41 | | | | | |
| | | | | | | | | | 28.51 |
| | | 28.52 | | | | | | | |
| | | | | | | | | 28.67 | |
| | | | | | | 28.72 | | | |
| | | | | | | | | | 28.74 |
| | | | | 28.97 | | | | | |
| | | | | | | 29.01 | | | |
| | | | | | | | | | 29.16 |
| | | | | 29.60 | | | | | |
| | | | | | | | | 29.67 | |
| | | | | | | | | | 29.89 |
| | | | | | | 29.91 | | | |
| | | | | | | | | | 30.06 |
| | | | | | | | | 30.48 | |
| | | | | 30.51 | | | | | 30.51 |
| | | | | 30.83 | | | | | |
| | | | | | | | | | 31.07 |
| | | | | | | | | 31.12 | |
| | | | | | | 31.30 | | | |
| | | | | | | | | | 31.42 |
| | | | | | | | | 31.75 | |
| | | | | | | | | | 31.98 |
| | | | | 31.99 | | | | | |
| | | | | | | | | | 32.33 |
| | | | | 32.56 | | | | | |
| | | | | | | | | | 32.88 |
| | | | | 33.52 | | | | | |
| | | | | | | | | | 33.67 |
| | | | | | | | | | 34.13 |
| | | | | | | | | | 34.38 |
| | | | | | | | | | 35.03 |
| | | | | | | | | | 35.73 |
| | | | | | | | | | 36.53 |
| | | | | | | | | | 37.47 |
| | | | | | | | | | 38.84 |

In one embodiment, the present invention provides Forms 1, Form 3, Form D, From H1 and Form J, which are further characterized by Fourier-transform infrared spectroscopy (FT-IR). The characteristic peaks are expressed in wave numbers ($cm^{-1}$). The positions of the characteristic peaks for each form are unique to that form. The position of intense peaks of the polymorphs and pseudopolymorphs are presented in Table 6. The relative intensity, as well as the position of intense peaks in FIG. 5, FIG. 11, FIG. 22, FIG. 31 or FIG. 34 may change or shift under certain condition, although the crystalline form is the same. One of ordinary skill in the art should be able to readily determine whether a given polymorph Form is the same polymorph Form as described in one of FIG. 5, FIG. 11, FIG. 22, FIG. 31, FIG. 34 or Table 6 by comparing their peak positions and intensities in the IR data.

The FT-IR spectra of Form 1, Form 3, Form D, Form H1 and Form J were found to be different from each other.

TABLE 6

| The intense peaks in the FT-IR spectra (in $cm^{-1}$) for Forms 1, Form 3, Form D, Form H1 and Form J | | | | |
|---|---|---|---|---|
| Form 1 (FIG. 5) | Form 3 (FIG. 11) | Form D (FIG. 22) | Form H1 (FIG. 31) | Form J (FIG. 34) |
| | | | 537 | |
| 549 | | | | |
| | 563 | | | |
| | | | | 564 |

TABLE 6-continued

| The intense peaks in the FT-IR spectra (in $cm^{-1}$) for Forms 1, Form 3, Form D, Form H1 and Form J | | | | |
|---|---|---|---|---|
| Form 1 (FIG. 5) | Form 3 (FIG. 11) | Form D (FIG. 22) | Form H1 (FIG. 31) | Form J (FIG. 34) |
| 572 | | | | |
| | 589 | | | |
| | | | 590 | |
| | | 591 | | |
| 592 | | | | |
| | | | | 598 |
| 602 | | | | |
| | | | | 620 |
| | 623 | | | |
| | | 626 | | |
| | | | 627 | |
| | 646 | | | |
| | | | | 648 |
| 649 | | | | |
| | 674 | | 674 | |
| | | 671 | | |
| 676 | | | | 676 |
| | | 696 | | |
| 706 | 706 | | | 706 |
| | | 707 | | |
| | | | 708 | |
| | 725 | | | |
| 726 | | | | |
| | | 731 | | |
| | | | 732 | |

TABLE 6-continued

| The intense peaks in the FT-IR spectra (in $cm^{-1}$) for Forms 1, Form 3, Form D, Form H1 and Form J | | | | |
|---|---|---|---|---|
| Form 1 (FIG. 5) | Form 3 (FIG. 11) | Form D (FIG. 22) | Form H1 (FIG. 31) | Form J (FIG. 34) |
| | | | | 737 |
| | 740 | | | |
| | | | 744 | |
| | | | | 749 |
| 751 | | | | 813 |
| | | 752 | | |
| | 754 | | | |
| | | | 755 | |
| 762 | | | | |
| | | | 791 | |
| | 802 | | | |
| 803 | | | | |
| | | 810 | | |
| | | | 811 | |
| | | 815 | | |
| 884 | | | | |
| 897 | | | | |
| | | | | 910 |
| 934 | | | | |
| | 966 | | | |
| 967 | | | | |
| | | 968 | | 968 |
| | | | 969 | |
| | | | | 1005 |
| 1016 | | | | |
| | | | | 1019 |
| | 1023 | | | |
| | 1049 | | | |
| 1050 | | 1050 | | |
| | | | 1053 | |
| | | | | 1065 |
| | 1079 | 1079 | | |
| | | | 1084 | |
| 1087 | | | | |
| | | | | 1089 |
| | | 1094 | | |
| | 1096 | | | |
| | | | 1110 | |
| 1111 | | | | |
| | | | 1114 | |
| | 1119 | | | |
| | | | | 1120 |
| 1128 | | | | |
| | 1130 | 1130 | | |
| | | | 1132 | |
| | | | | 1133 |
| | | | | 1156 |
| | 1158 | | | |
| 1161 | | 1161 | 1161 | |
| 1185 | | | | |
| | 1186 | | 1203 | |
| 1201 | | | | |
| | | 1202 | | |
| | | | | 1209 |
| | 1215 | | | |
| 1227 | | | | |
| | | | 1234 | |
| 1243 | | | | |
| | | | | 1249 |
| | 1254 | | | |
| | | | | 1267 |
| | 1283 | | | |
| | | | 1284 | |
| | | | | 1306 |
| | 1310 | | | |
| 1320 | | | | |
| | | | 1325 | |
| | | | | 1326 |
| | | 1329 | | |
| | 1352 | | | |
| | | | | 1353 |
| | 1376 | 1376 | | |
| | | | | 1377 |
| | 1385 | | | |
| | | 1387 | | |
| | | | 1388 | |
| 1392 | | | | |
| | 1394 | | | 1394 |
| | | | | 1426 |
| 1447 | | 1431 | | |
| | 1439 | | | 1439 |
| | | | 1445 | |
| | 1469 | 1469 | | |
| 1470 | | | 1470 | |
| | | | | 1471 |
| | 1484 | | | 1484 |
| 1485 | | 1485 | | |
| | 1519 | | | |
| | | | | 1522 |
| | | 1524 | | |
| | | | 1525 | |
| 1528 | | | | |
| 1546 | | 1546 | | 1546 |
| | 1549 | | | |
| | | 1595 | | |
| | 1598 | | 1598 | 1598 |
| 1599 | | | | |
| | | | 1638 | |
| | | 1649 | | |
| | 1656 | | | |
| | | | | 1657 |
| | | | 1658 | |
| 1673 | | | | |
| 1694 | | | | |
| | | | 1711 | |
| 1712 | | | | |
| | | | | 1723 |
| | 1727 | 1727 | | |
| 2868 | | | | |
| | | | | 2870 |
| | 2878 | | | |
| | 2957 | | | 2957 |
| | | 2958 | | |
| 2960 | | | | |
| | | | | 3196 |
| 3199 | | | | |
| | | 3231 | | |
| | | | | 3335 |
| | | | 3245 | |
| | 3422 | | | |
| | 3464 | | | |

Form 1 of Compound I provides improved or modulated physicochemical properties of the compound, including, but not limited to, solid state properties (e.g., crystallinity, hygroscopicity, melting point), pharmaceutical properties (e.g., stability, or compatibility), as well as crystallization characteristics (e.g., purity, yield, or morphology).

Crystalline Form 1 was further characterized by single crystal X-ray diffraction. The crystal parameters obtained from this analysis are presented in Table 7.

TABLE 7

| Crystal Parameter Data of Form 1 | |
|---|---|
| Parameter | Data |
| $M_r$ | 537.54 |
| Trigonal | $P3_2$ |
| A | 14.9109 (2) Å |
| C | 10.4352 (2) Å |
| V | 2009.27 (7) $Å^3$ |
| Z | 3 |
| F(000) | 840 |

TABLE 7-continued

| Crystal Parameter Data of Form 1 | |
|---|---|
| Parameter | Data |
| $D_x$ | 1.333 Mg $m^{-3}$ |
| Cu Kα radiation, λ | 1.54178 Å |
| Cell parameters from 7014 reflections | θ = 5.5-74.6° |
| | μ = 0.87 $mm^{-1}$ |
| | T = 170 K |
| | Block, colourless |
| | 0.15 × 0.08 × 0.05 mm |

Figure 6:
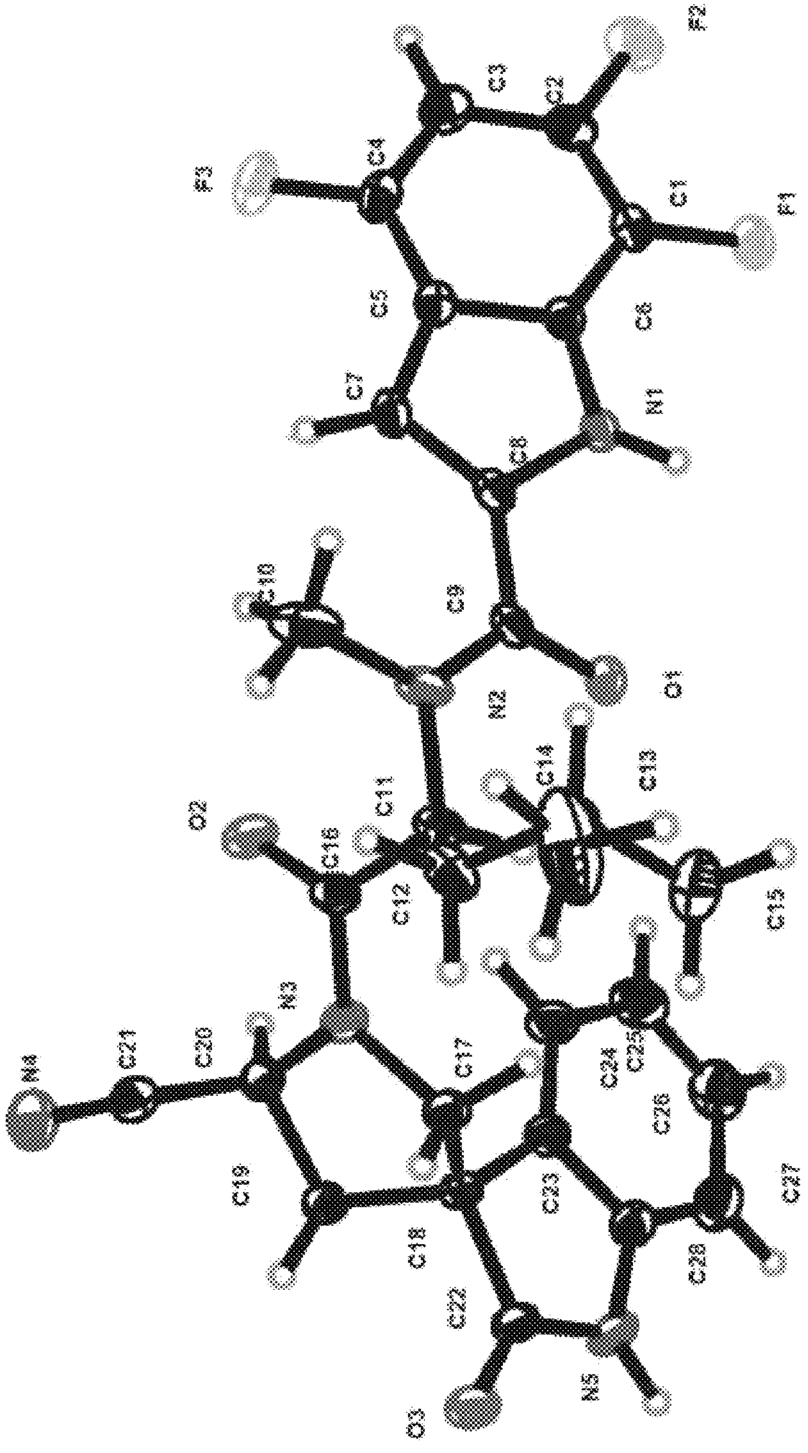
FIG. 6 is the ORTEP plot of the single crystal X-ray structure of Form 1.

Crystalline Form 1 was further characterized by single crystal X-ray diffraction analysis. The results of single crystal X-ray diffraction analysis describe the atomic positions and other structural parameters which determine the structure of Form 1 are shown in Table 8 and Table 9, and the bond distances and bond angles of the Form 1 are listed in Table 10. The distances are in angstroms and the bond angles are in degrees. The estimated standard deviations for bond distances and bond angles in the least significant figure are given in parentheses. The molecular structure from single crystal X-ray diffraction analysis for Form 1 is depicted in FIG. 6 as an Oak Ridge Thermal Ellipsoid plot (ORTEP).

TABLE 8

Form 1 Fractional atomic coordinates and isotropic or equivalent isotropic displacement parameters (Å2)

| | X | Y | Z | $U_{iso}$*/$U_{eq}$ | Occ. (<1) |
|---|---|---|---|---|---|
| F3 | 0.45327 (15) | 0.10216 (15) | 0.4062 (2) | 0.0590 (5) | |
| F2 | 0.78285 (18) | 0.13361 (17) | 0.3911 (2) | 0.0619 (6) | |
| F1 | 0.87565 (14) | 0.34384 (15) | 0.3866 (2) | 0.0531 (5) | |
| O2 | 0.46034 (17) | 0.56292 (16) | 0.5889 (2) | 0.0436 (5) | |
| N3 | 0.53704 (19) | 0.73528 (18) | 0.6022 (2) | 0.0342 (5) | |
| O3 | 0.64500 (17) | 1.05095 (16) | 0.6862 (2) | 0.0437 (5) | |
| N1 | 0.73524 (17) | 0.43146 (17) | 0.3947 (2) | 0.0299 (5) | |
| H1 | 0.798524 | 0.484942 | 0.392541 | 0.036* | |
| O1 | 0.74257 (15) | 0.60993 (16) | 0.4611 (3) | 0.0452 (5) | |
| N5 | 0.7824 (2) | 1.04798 (18) | 0.7821 (3) | 0.0444 (6) | |
| H5 | 0.820583 | 1.114314 | 0.799969 | 0.053* | |
| C16 | 0.5241 (2) | 0.6473 (2) | 0.5454 (3) | 0.0342 (6) | |
| N2 | 0.5800 (2) | 0.5587 (2) | 0.3974 (3) | 0.0456 (7) | |
| C6 | 0.7100 (2) | 0.3306 (2) | 0.3930 (3) | 0.0293 (5) | |
| C8 | 0.6449 (2) | 0.4366 (2) | 0.4005 (3) | 0.0312 (6) | |
| N4 | 0.2899 (2) | 0.6710 (2) | 0.6851 (3) | 0.0521 (7) | |
| C17 | 0.6157 (2) | 0.8441 (2) | 0.5788 (3) | 0.0356 (6) | |
| H17A | 0.586495 | 0.880220 | 0.529588 | 0.043* | |
| H17B | 0.675804 | 0.849275 | 0.531698 | 0.043* | |
| C5 | 0.6013 (2) | 0.2688 (2) | 0.3976 (3) | 0.0320 (6) | |
| C22 | 0.6898 (2) | 1.0058 (2) | 0.7226 (3) | 0.0351 (6) | |
| C7 | 0.5618 (2) | 0.3377 (2) | 0.4017 (3) | 0.0346 (6) | |
| H7 | 0.490867 | 0.318922 | 0.404776 | 0.042* | |

TABLE 8-continued

Form 1 Fractional atomic coordinates and isotropic or equivalent isotropic displacement parameters (Å2)

| | X | Y | Z | $U_{iso}$*/$U_{eq}$ | Occ. (<1) |
|---|---|---|---|---|---|
| C21 | 0.3742 (2) | 0.6924 (2) | 0.7024 (3) | 0.0369 (6) | |
| C1 | 0.7715 (2) | 0.2846 (2) | 0.3898 (3) | 0.0356 (6) | |
| C20 | 0.4836 (2) | 0.7247 (2) | 0.7240 (3) | 0.0330 (6) | |
| H20 | 0.489134 | 0.673307 | 0.780095 | 0.040* | |
| C9 | 0.6584 (2) | 0.5410 (2) | 0.4206 (3) | 0.0319 (6) | |
| C23 | 0.7322 (2) | 0.8764 (2) | 0.7718 (3) | 0.0366 (6) | |
| C4 | 0.5577 (2) | 0.1612 (2) | 0.3995 (3) | 0.0397 (7) | |
| C19 | 0.5420 (2) | 0.8330 (2) | 0.7852 (3) | 0.0358 (6) | |
| H19A | 0.552622 | 0.828145 | 0.877960 | 0.043* | |
| H19B | 0.503193 | 0.870341 | 0.773332 | 0.043* | |
| C28 | 0.8108 (2) | 0.9737 (2) | 0.8121 (3) | 0.0413 (7) | |
| C18 | 0.6465 (2) | 0.8885 (2) | 0.7137 (3) | 0.0328 (6) | |
| C2 | 0.7238 (3) | 0.1789 (2) | 0.3928 (3) | 0.0423 (7) | |
| C24 | 0.7438 (3) | 0.7909 (3) | 0.7880 (3) | 0.0468 (8) | |
| H24 | 0.691657 | 0.724414 | 0.759904 | 0.056* | |
| C11 | 0.5942 (2) | 0.6607 (2) | 0.4322 (3) | 0.0386 (7) | |
| H11 | 0.667034 | 0.703467 | 0.463367 | 0.046* | |
| C3 | 0.6166 (3) | 0.1153 (2) | 0.3966 (3) | 0.0442 (7) | |
| H3 | 0.585688 | 0.042059 | 0.397249 | 0.053* | |
| C27 | 0.8991 (3) | 0.9878 (3) | 0.8715 (4) | 0.0571 (9) | |
| H27 | 0.951364 | 1.054222 | 0.899461 | 0.069* | |
| C25 | 0.8335 (3) | 0.8043 (3) | 0.8466 (4) | 0.0608 (10) | |
| H25 | 0.843111 | 0.746441 | 0.857590 | 0.073* | |
| C12 | 0.5827 (3) | 0.7181 (3) | 0.3170 (3) | 0.0476 (8) | |
| H12C | 0.542212 | 0.750915 | 0.344535 | 0.057* | 0.4 |
| H12D | 0.541891 | 0.666485 | 0.250263 | 0.057* | 0.4 |
| H12A | 0.513728 | 0.674344 | 0.277731 | 0.057* | 0.6 |
| H12B | 0.586080 | 0.782661 | 0.347428 | 0.057* | 0.6 |
| C10 | 0.4784 (3) | 0.4804 (4) | 0.3480 (5) | 0.0799 (17) | |
| H10A | 0.487912 | 0.446608 | 0.272899 | 0.120* | |
| H10B | 0.438571 | 0.513758 | 0.323657 | 0.120* | |
| H10C | 0.440968 | 0.428572 | 0.414617 | 0.120* | |
| C26 | 0.9085 (3) | 0.9003 (3) | 0.8889 (4) | 0.0646 (11) | |
| H26 | 0.968135 | 0.907040 | 0.930822 | 0.077* | |
| C13 | 0.6640 (4) | 0.7446 (5) | 0.2177 (5) | 0.0426 (12) | 0.6 |
| H13 | 0.667746 | 0.681275 | 0.195677 | 0.051* | 0.6 |
| C15 | 0.7684 (6) | 0.8271 (6) | 0.2748 (8) | 0.0644 (18) | 0.6 |
| H15A | 0.764163 | 0.888298 | 0.299179 | 0.097* | 0.6 |
| H15B | 0.823248 | 0.846605 | 0.210791 | 0.097* | 0.6 |
| H15C | 0.784297 | 0.798773 | 0.350626 | 0.097* | 0.6 |
| C14 | 0.6374 (7) | 0.7830 (11) | 0.1021 (8) | 0.106 (4) | 0.6 |
| H14A | 0.577790 | 0.725410 | 0.059590 | 0.159* | 0.6 |
| H14B | 0.696643 | 0.813051 | 0.043400 | 0.159* | 0.6 |
| H14C | 0.620027 | 0.835974 | 0.126314 | 0.159* | 0.6 |
| C29 | 0.6943 (11) | 0.8102 (13) | 0.2503 (12) | 0.069 (3) | 0.4 |
| H29 | 0.732724 | 0.861016 | 0.320157 | 0.082* | 0.4 |
| C31 | 0.7611 (11) | 0.7734 (12) | 0.2074 (17) | 0.091 (5) | 0.4 |
| H31A | 0.783192 | 0.748293 | 0.280843 | 0.137* | 0.4 |
| H31B | 0.822012 | 0.830002 | 0.165575 | 0.137* | 0.4 |
| H31C | 0.723964 | 0.716757 | 0.146160 | 0.137* | 0.4 |
| C30 | 0.6711 (11) | 0.8701 (14) | 0.1484 (16) | 0.089 (4) | 0.4 |
| H30A | 0.597402 | 0.831292 | 0.125944 | 0.134* | 0.4 |
| H30B | 0.712792 | 0.879251 | 0.071757 | 0.134* | 0.4 |
| H30C | 0.688181 | 0.938141 | 0.182402 | 0.134* | 0.4 |

TABLE 9

Form 1 Atomic displacement parameters (Å$^2$)

| | $U^{11}$ | $U^{22}$ | $U^{33}$ | $U^{12}$ | $U^{13}$ | $U^{23}$ |
|---|---|---|---|---|---|---|
| F3 | 0.0354 (10) | 0.0449 (11) | 0.0753 (14) | 0.0039 (8) | 0.0010 (9) | 0.0062 (10) |
| F2 | 0.0676 (14) | 0.0536 (12) | 0.0835 (16) | 0.0445 (11) | 0.0075 (11) | 0.0054 (11) |
| F1 | 0.0331 (9) | 0.0528 (12) | 0.0792 (15) | 0.0257 (9) | 0.0034 (9) | 0.0010 (10) |
| O2 | 0.0501 (13) | 0.0296 (11) | 0.0522 (14) | 0.0208 (10) | −0.0117 (10) | −0.0069 (9) |
| N3 | 0.0389 (13) | 0.0279 (11) | 0.0322 (13) | 0.0139 (10) | 0.0042 (10) | −0.0033 (9) |
| O3 | 0.0485 (12) | 0.0312 (10) | 0.0543 (14) | 0.0220 (10) | −0.0061 (10) | −0.0025 (9) |
| N1 | 0.0240 (10) | 0.0329 (12) | 0.0327 (12) | 0.0141 (9) | −0.0004 (9) | −0.0031 (9) |
| O1 | 0.0236 (10) | 0.0391 (11) | 0.0721 (16) | 0.0150 (9) | −0.0001 (10) | −0.0061 (10) |
| N5 | 0.0411 (14) | 0.0214 (11) | 0.0636 (17) | 0.0104 (11) | −0.0085 (12) | −0.0014 (11) |
| C16 | 0.0398 (15) | 0.0358 (15) | 0.0358 (15) | 0.0256 (13) | −0.0099 (12) | −0.0064 (11) |

TABLE 9-continued

| Form 1 Atomic displacement parameters (Å$^2$) | | | | | | |
|---|---|---|---|---|---|---|
| | $U^{11}$ | $U^{22}$ | $U^{33}$ | $U^{12}$ | $U^{13}$ | $U^{23}$ |
| N2 | 0.0448 (14) | 0.0548 (16) | 0.0538 (17) | 0.0374 (13) | −0.0242 (12) | −0.0302 (13) |
| C6 | 0.0287 (13) | 0.0347 (14) | 0.0248 (13) | 0.0160 (11) | 0.0010 (10) | −0.0001 (10) |
| C8 | 0.0276 (13) | 0.0430 (15) | 0.0269 (13) | 0.0206 (12) | −0.0001 (10) | −0.0039 (11) |
| N4 | 0.0396 (15) | 0.0580 (18) | 0.0551 (18) | 0.0218 (14) | −0.0064 (13) | −0.0022 (14) |
| C17 | 0.0425 (16) | 0.0286 (13) | 0.0348 (15) | 0.0170 (12) | 0.0064 (12) | 0.0013 (11) |
| C5 | 0.0298 (13) | 0.0372 (14) | 0.0267 (14) | 0.0151 (12) | 0.0000 (10) | 0.0013 (11) |
| C22 | 0.0396 (15) | 0.0244 (13) | 0.0392 (16) | 0.0143 (12) | 0.0013 (12) | −0.0016 (11) |
| C7 | 0.0248 (13) | 0.0452 (16) | 0.0330 (15) | 0.0167 (12) | 0.0003 (10) | −0.0026 (12) |
| C21 | 0.0421 (17) | 0.0327 (14) | 0.0318 (15) | 0.0157 (13) | 0.0015 (12) | 0.0013 (11) |
| C1 | 0.0306 (14) | 0.0417 (16) | 0.0351 (15) | 0.0184 (12) | 0.0036 (11) | 0.0020 (12) |
| C20 | 0.0346 (14) | 0.0298 (14) | 0.0317 (14) | 0.0139 (12) | 0.0021 (11) | −0.0006 (11) |
| C9 | 0.0288 (13) | 0.0443 (15) | 0.0279 (14) | 0.0222 (12) | 0.0011 (10) | −0.0043 (11) |
| C23 | 0.0413 (16) | 0.0319 (14) | 0.0375 (16) | 0.0188 (13) | 0.0060 (12) | 0.0035 (12) |
| C4 | 0.0335 (15) | 0.0379 (16) | 0.0353 (16) | 0.0087 (13) | 0.0011 (11) | 0.0040 (12) |
| C19 | 0.0384 (15) | 0.0328 (14) | 0.0344 (15) | 0.0166 (12) | 0.0049 (12) | −0.0043 (11) |
| C28 | 0.0391 (16) | 0.0339 (15) | 0.0492 (18) | 0.0171 (13) | 0.0021 (13) | 0.0048 (13) |
| C18 | 0.0356 (14) | 0.0245 (13) | 0.0376 (15) | 0.0145 (11) | 0.0034 (11) | −0.0003 (11) |
| C2 | 0.0520 (18) | 0.0438 (17) | 0.0419 (17) | 0.0319 (15) | 0.0028 (14) | 0.0027 (13) |
| C24 | 0.0553 (19) | 0.0376 (16) | 0.054 (2) | 0.0278 (15) | 0.0032 (15) | 0.0037 (14) |
| C11 | 0.0403 (16) | 0.0471 (17) | 0.0401 (16) | 0.0305 (14) | −0.0119 (12) | −0.0172 (13) |
| C3 | 0.0534 (19) | 0.0350 (15) | 0.0420 (17) | 0.0204 (15) | 0.0009 (14) | 0.0054 (13) |
| C27 | 0.0439 (19) | 0.0495 (19) | 0.071 (3) | 0.0180 (16) | −0.0067 (17) | 0.0051 (17) |
| C25 | 0.071 (3) | 0.059 (2) | 0.070 (3) | 0.046 (2) | 0.003 (2) | 0.0103 (19) |
| C12 | 0.0476 (18) | 0.076 (2) | 0.0340 (17) | 0.0419 (18) | −0.0054 (13) | −0.0091 (15) |
| C10 | 0.070 (3) | 0.088 (3) | 0.114 (4) | 0.063 (3) | −0.067 (3) | −0.074 (3) |
| C26 | 0.055 (2) | 0.074 (3) | 0.075 (3) | 0.040 (2) | −0.0082 (19) | 0.010 (2) |
| C13 | 0.040 (3) | 0.047 (3) | 0.039 (3) | 0.021 (3) | 0.005 (2) | −0.012 (2) |
| C15 | 0.044 (4) | 0.062 (4) | 0.071 (5) | 0.015 (3) | 0.006 (3) | 0.015 (4) |
| C14 | 0.069 (5) | 0.197 (12) | 0.041 (4) | 0.059 (7) | 0.017 (4) | 0.033 (6) |
| C29 | 0.078 (8) | 0.094 (9) | 0.053 (6) | 0.057 (7) | 0.017 (5) | 0.015 (6) |
| C31 | 0.081 (9) | 0.092 (10) | 0.118 (12) | 0.056 (8) | 0.058 (9) | 0.049 (9) |
| C30 | 0.078 (9) | 0.118 (11) | 0.084 (10) | 0.057 (9) | 0.024 (7) | 0.055 (8) |

TABLE 10

| Form 1 Geometric parameters | | | | | |
|---|---|---|---|---|---|
| Bond distance (Å) | | | | | |
| F3—C4 | 1.354 (4) | C5—C7 | 1.417 (4) | C12—H12D | 0.9900 |
| F2—C2 | 1.351 (4) | C5—C4 | 1.398 (4) | C12—H12A | 0.9900 |
| F1—C1 | 1.350 (3) | C22—C18 | 1.535 (4) | C12—H12B | 0.9900 |
| O2—C16 | 1.223 (4) | C7—H7 | 0.9500 | C12—C13 | 1.491 (6) |
| N3—C16 | 1.363 (4) | C21—C20 | 1.469 (4) | C12—C29 | 1.689 (14) |
| N3—C17 | 1.471 (4) | C1—C2 | 1.368 (4) | C10—H10A | 0.9800 |
| N3—C20 | 1.466 (4) | C20—H20 | 1.0000 | C10—H10B | 0.9800 |
| O3—C22 | 1.222 (4) | C20—C19 | 1.539 (4) | C10—H10C | 0.9800 |
| N1—H1 | 0.8800 | C23—C28 | 1.398 (4) | C26—H26 | 0.9500 |
| N1—C6 | 1.356 (3) | C23—C18 | 1.505 (4) | C13—H13 | 1.0000 |
| N1—C8 | 1.388 (3) | C23—C24 | 1.379 (4) | C13—C15 | 1.541 (9) |
| O1—C9 | 1.233 (3) | C4—C3 | 1.357 (5) | C13—C14 | 1.472 (11) |
| N5—H5 | 0.8800 | C19—H19A | 0.9900 | C15—H15A | 0.9800 |
| N5—C22 | 1.348 (4) | C19—H19B | 0.9900 | C15—H15B | 0.9800 |
| N5—C28 | 1.405 (4) | C19—C18 | 1.543 (4) | C15—H15C | 0.9800 |
| C16—C11 | 1.522 (4) | C28—C27 | 1.373 (5) | C14—H14A | 0.9800 |
| N2—C9 | 1.344 (4) | C2—C3 | 1.393 (5) | C14—H14B | 0.9800 |
| N2—C11 | 1.472 (4) | C24—H24 | 0.9500 | C14—H14C | 0.9800 |
| N2—C10 | 1.467 (4) | C24—C25 | 1.392 (5) | C29—H29 | 1.0000 |
| C6—C5 | 1.409 (4) | C11—H11 | 1.0000 | C29—C31 | 1.428 (16) |
| C6—C1 | 1.392 (4) | C11—C12 | 1.534 (5) | C29—C30 | 1.536 (16) |
| C8—C7 | 1.371 (4) | C3—H3 | 0.9500 | C31—H31A | 0.9800 |
| C8—C9 | 1.482 (4) | C27—H27 | 0.9500 | C31—H31B | 0.9800 |
| N4—C21 | 1.146 (4) | C27—C26 | 1.392 (6) | C31—H31C | 0.9800 |
| C17—H17A | 0.9900 | C25—H25 | 0.9500 | C30—H30A | 0.9800 |
| C17—H17B | 0.9900 | C25—C26 | 1.376 (6) | C30—H30B | 0.9800 |
| C17—C18 | 1.525 (4) | C12—H12C | 0.9900 | C30—H30C | 0.9800 |
| Bond angle (°) | | | | | |
| C16—N3—C17 | 129.8 (2) | C24—C23—C28 | 119.6 (3) | C13—C12—H12B | 109.0 |
| C16—N3—C20 | 117.8 (2) | C24—C23—C18 | 131.8 (3) | C29—C12—H12C | 108.3 |
| C20—N3—C17 | 110.7 (2) | F3—C4—C5 | 118.0 (3) | C29—C12—H12D | 108.3 |
| C6—N1—H1 | 125.6 | F3—C4—C3 | 119.8 (3) | N2—C10—H10A | 109.5 |
| C6—N1—C8 | 108.8 (2) | C3—C4—C5 | 122.1 (3) | N2—C10—H10B | 109.5 |

TABLE 10-continued

| Form 1 Geometric parameters | | | | | |
|---|---|---|---|---|---|
| C8—N1—H1 | 125.6 | C20—C19—H19A | 110.8 | N2—C10—H10C | 109.5 |
| C22—N5—H5 | 123.9 | C20—C19—H19B | 110.8 | H10A—C10—H10B | 109.5 |
| C22—N5—C28 | 112.1 (2) | C20—C19—C18 | 104.6 (2) | H10A—C10—H10C | 109.5 |
| C28—N5—H5 | 123.9 | H19A—C19—H19B | 108.9 | H10B—C10—H10C | 109.5 |
| O2—C16—N3 | 119.5 (3) | C18—C19—H19A | 110.8 | C27—C26—H26 | 119.3 |
| O2—C16—C11 | 123.5 (3) | C18—C19—H19B | 110.8 | C25—C26—C27 | 121.5 (4) |
| N3—C16—C11 | 117.0 (3) | C23—C28—N5 | 108.9 (3) | C25—C26—H26 | 119.3 |
| C9—N2—C11 | 118.0 (2) | C27—C28—N5 | 128.6 (3) | C12—C13—H13 | 109.4 |
| C9—N2—C10 | 124.0 (3) | C27—C28—C23 | 122.5 (3) | C12—C13—C15 | 107.8 (5) |
| C10—N2—C11 | 117.8 (3) | C17—C18—C22 | 114.5 (2) | C15—C13—H13 | 109.4 |
| N1—C6—C5 | 108.4 (2) | C17—C18—C19 | 102.1 (2) | C14—C13—C12 | 109.3 (5) |
| N1—C6—C1 | 131.3 (3) | C22—C18—C19 | 108.6 (2) | C14—C13—H13 | 109.4 |
| C1—C6—C5 | 120.3 (3) | C23—C18—C17 | 114.1 (2) | C14—C13—C15 | 111.6 (7) |
| N1—C8—C9 | 116.0 (2) | C23—C18—C22 | 102.3 (2) | C13—C15—H15A | 109.5 |
| C7—C8—N1 | 108.7 (2) | C23—C18—C19 | 115.6 (2) | C13—C15—H15B | 109.5 |
| C7—C8—C9 | 134.7 (3) | F2—C2—C1 | 118.9 (3) | C13—C15—H15C | 109.5 |
| N3—C17—H17A | 111.1 | F2—C2—C3 | 118.2 (3) | H15A—C15—H15B | 109.5 |
| N3—C17—H17B | 111.1 | C1—C2—C3 | 122.9 (3) | H15A—C15—H15C | 109.5 |
| N3—C17—C18 | 103.1 (2) | C23—C24—H24 | 120.8 | H15B—C15—H15C | 109.5 |
| H17A—C17—H17B | 109.1 | C23—C24—C25 | 118.5 (3) | C13—C14—H14A | 109.5 |
| C18—C17—H17A | 111.1 | C25—C24—H24 | 120.8 | C13—C14—H14B | 109.5 |
| C18—C17—H17B | 111.1 | C16—C11—H11 | 106.7 | C13—C14—H14C | 109.5 |
| C6—C5—C7 | 106.6 (2) | C16—C11—C12 | 114.9 (2) | H14A—C14—H14B | 109.5 |
| C4—C5—C6 | 118.2 (3) | N2—C11—C16 | 108.7 (3) | H14A—C14—H14C | 109.5 |
| C4—C5—C7 | 135.1 (3) | N2—C11—H11 | 106.7 | H14B—C14—H14C | 109.5 |
| O3—C22—N5 | 126.9 (3) | N2—C11—C12 | 112.6 (3) | C12—C29—H29 | 105.9 |
| O3—C22—C18 | 125.0 (3) | C12—C11—H11 | 106.7 | C31—C29—C12 | 114.2 (11) |
| N5—C22—C18 | 108.0 (2) | C4—C3—C2 | 118.0 (3) | C31—C29—H29 | 105.9 |
| C8—C7—C5 | 107.5 (2) | C4—C3—H3 | 121.0 | C31—C29—C30 | 114.2 (11) |
| C8—C7—H7 | 126.3 | C2—C3—H3 | 121.0 | C30—C29—C12 | 110.0 (10) |
| C5—C7—H7 | 126.3 | C28—C27—H27 | 121.5 | C30—C29—H29 | 105.9 |
| N4—C21—C20 | 177.4 (3) | C28—C27—C26 | 117.0 (4) | C29—C31—H31A | 109.5 |
| F1—C1—C6 | 120.3 (3) | C26—C27—H27 | 121.5 | C29—C31—H31B | 109.5 |
| F1—C1—C2 | 121.3 (3) | C24—C25—H25 | 119.5 | C29—C31—H31C | 109.5 |
| C2—C1—C6 | 118.4 (3) | C26—C25—C24 | 120.9 (3) | H31A—C31—H31B | 109.5 |
| N3—C20—C21 | 110.9 (2) | C26—C25—H25 | 119.5 | H31A—C31—H31C | 109.5 |
| N3—C20—H20 | 110.0 | C11—C12—H12C | 108.3 | H31B—C31—H31C | 109.5 |
| N3—C20—C19 | 104.8 (2) | C11—C12—H12D | 108.3 | C29—C30—H30A | 109.5 |
| C21—C20—H20 | 110.0 | C11—C12—H12A | 109.0 | C29—C30—H30B | 109.5 |
| C21—C20—C19 | 111.1 (2) | C11—C12—H12B | 109.0 | C29—C30—H30C | 109.5 |
| C19—C20—H20 | 110.0 | C11—C12—C29 | 115.9 (5) | H30A—C30—H30B | 109.5 |
| O1—C9—N2 | 121.4 (3) | H12C—C12—H12D | 107.4 | H30A—C30—H30C | 109.5 |
| O1—C9—C8 | 118.1 (2) | H12A—C12—H12B | 107.8 | H30B—C30—H30C | 109.5 |
| N2—C9—C8 | 120.5 (2) | C13—C12—C11 | 112.9 (3) | | |
| C28—C23—C18 | 108.5 (2) | C13—C12—H12A | 109.0 | | |

Figure 4:
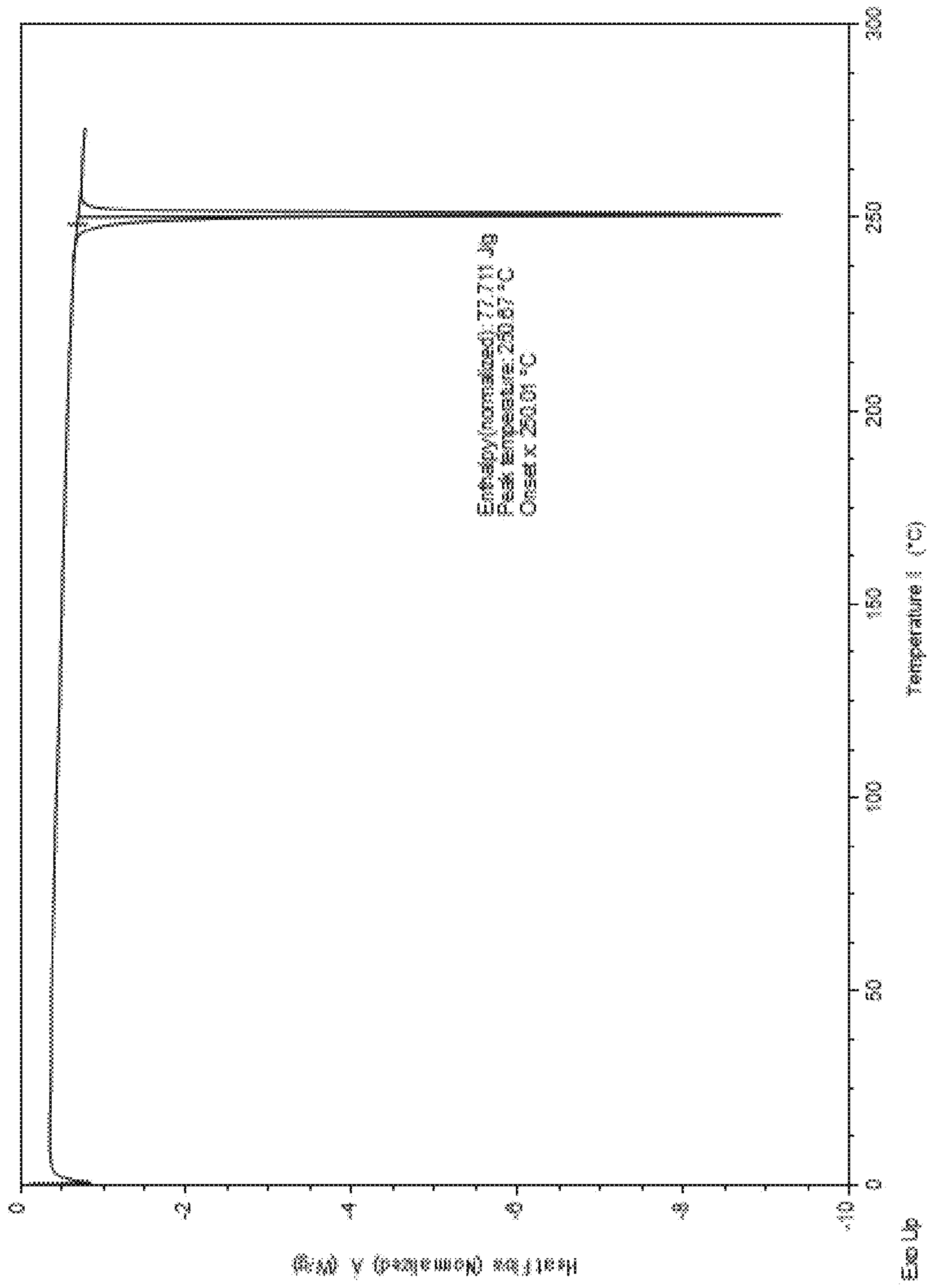
FIG. 4 is the DSC thermogram of Form 1 of Compound I.

The DSC thermogram of the crystalline Form 1 is shown in FIG. 4. The DSC thermogram of the crystalline Form 1 has a characteristic endotherm at 251° C. with an onset temperature at 250° C.

Figure 3:
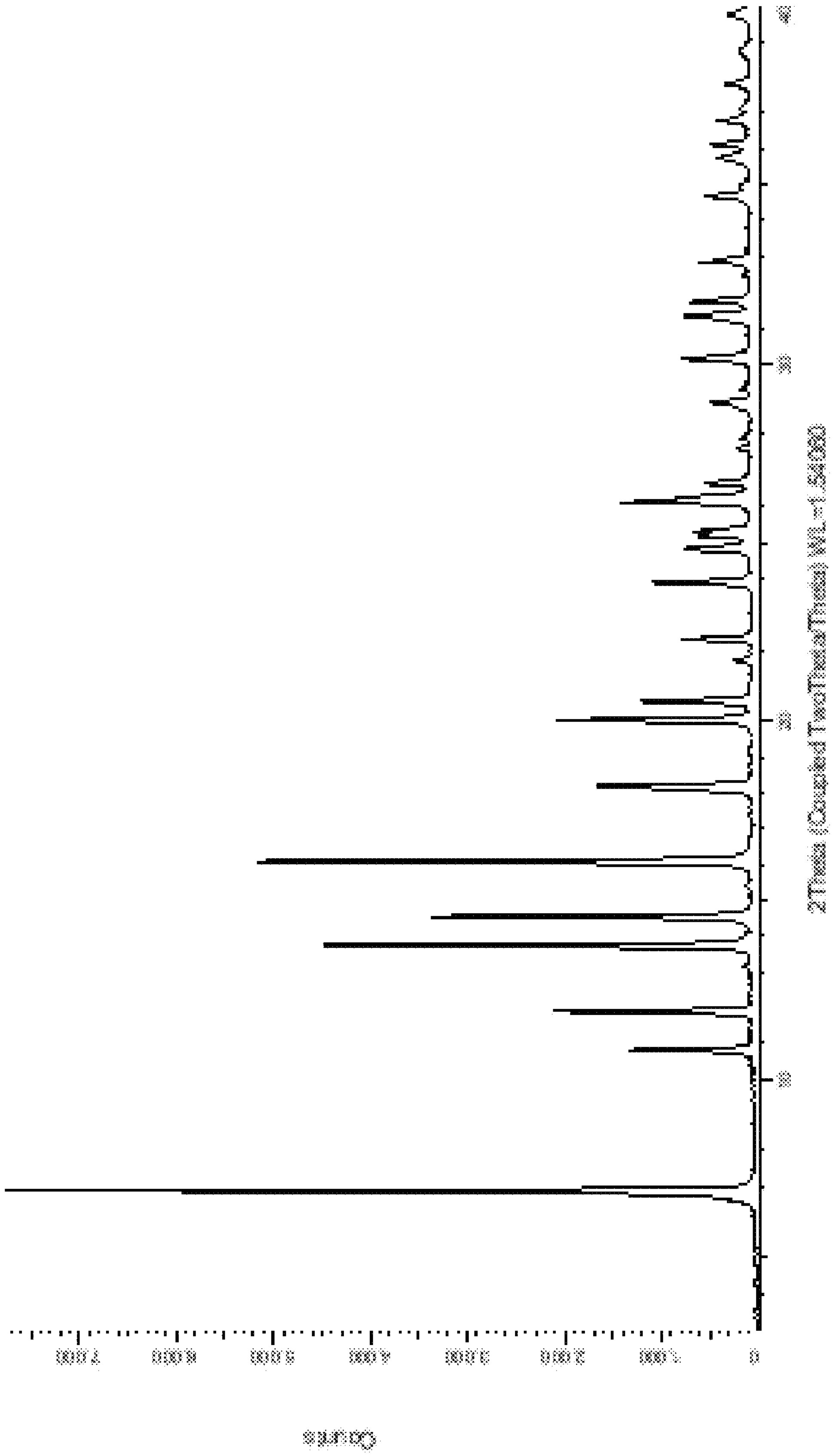
FIG. 3 is the XRPD pattern of Form 1 of Compound I.

The characteristic peaks (2θ) in the X-ray powder diffraction pattern of crystalline Form 1 are shown in FIG. 3. The characteristic peaks are at values of two theta (2θ) of 6.88, 8.32, 10.82, 11.90, 13.15, 13.74, 14.54, 15.41, 16.09, 18.19, 19.19, 20.04, 20.56, 21.69, 22.29, 23.87, 24.83, 25.19, 25.31, 26.13, 26.66, 27.63, 27.92, 28.90, 29.29, 30.14, 31.32, 31.32, 31.74, 32.48, 32.86, 34.66, 34.95, 35.75, 36.11, 36.79, 37.12, 37.79, 38.76, and 39.74. The characteristic peaks can alternatively be represented as (2θ) 6.9, 8.3, 10.8, 11.9, 13.2, 13.7, 14.5, 15.4, 16.1, 18.2, 19.2, 20.0, 20.6, 21.7, 22.3, 23.9, 24.8, 25.2, 25.3, 26.1, 26.7, 27.6, 27.9, 28.9, 29.3, 30.1, 31.3, 31.3, 31.7, 32.5, 32.9, 34.7, 35.0, 35.8, 36.1, 36.8, 37.1, 37.8, 38.8, and 39.7.

Figure 5:
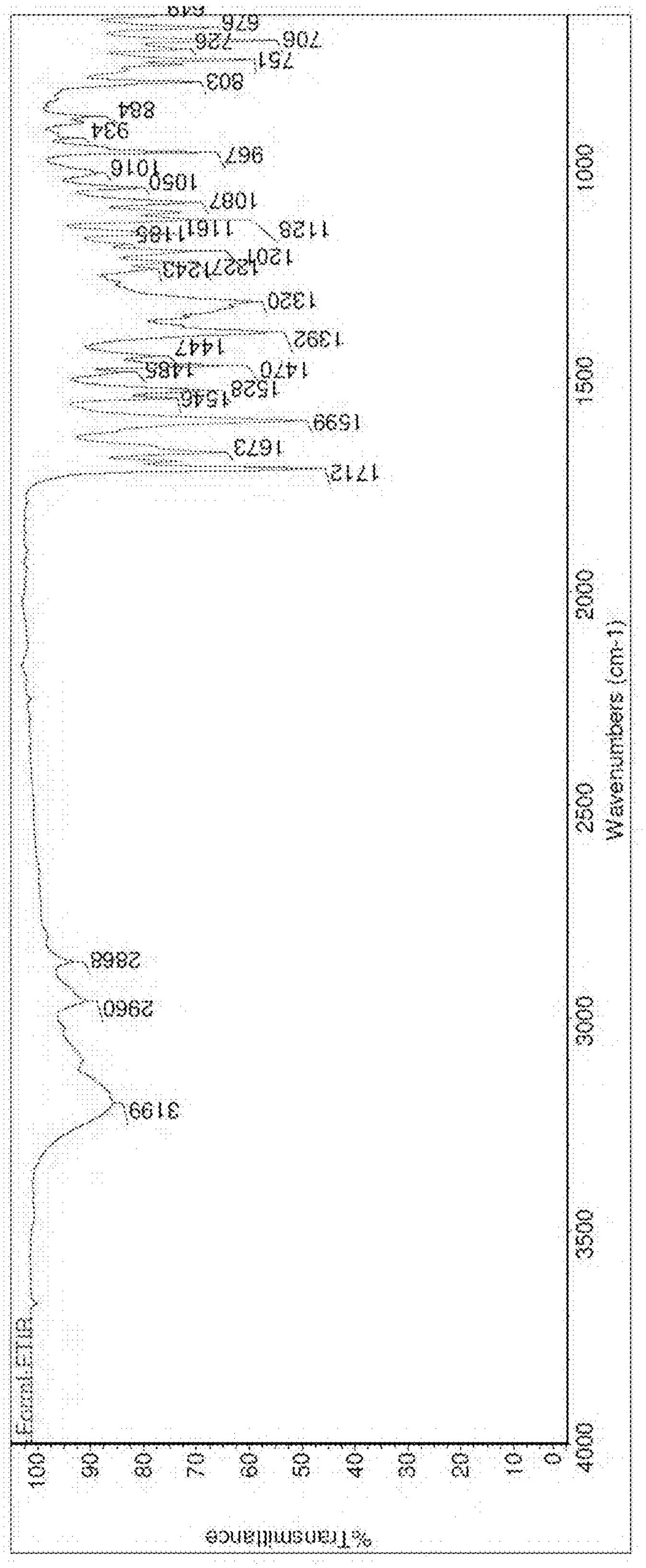
FIG. 5 is the Fourier-transform infrared (FT-IR) spectrum of Form 1 of Compound I.

The FT-IR spectrum of the crystalline Form 1 is shown in FIG. 5. Form 1 has characteristic peaks (in wave numbers ($cm^{-1}$)) at 549, 572, 592, 602, 649, 676, 706, 726, 751, 762, 803, 884, 897, 934, 967, 1016, 1050, 1087, 1111, 1128, 1161, 1185, 1201, 1227, 1243, 1320, 1392, 1447, 1470, 1485, 1528, 1546, 1599, 1673, 1694, 1712, 2868, 2960, and 3199.

Methods of preparing the polymorphs and pseudopolymorphs of the invention are described below. In each volume/weight ratio described herein, volume is in milliliters (mL) and weight is in grams (g).

The present invention provides a method of preparing Form 1 of Compound I by crystallization. In one embodiment, the method comprises the steps of:

1. preparing a solution of Compound I by dehydrating (3R,5'S)-1'-(N-methyl-N-(4,6,7-trifluoro-1H-indole-2-carbonyl)-L-leucyl)-2-oxospiro[indoline-3,3'-pyrrolidine]-5'-carboxamide (Compound N) in the presence of a suitable dehydration reagent or reagents, a suitable base, and a suitable solvent.
2. concentrating the solution of Compound I from step 1 at a temperature from about 20° C. to about 80° C., preferably from about 45° C. to about 55° C., and more preferably about 50° C., to a solvent/Compound N ratio by volume (milliliter)/weight (gram) about 2:1 to about 6:1, preferably from about 3.5:1 to about 4.5:1, and more preferably about 4:1.
3. optionally adding about 0.0001X (X=weight of Compound N in step 1) to about 0.1X of Form 1 of Compound I, more preferably 0.001X by weight as seed into concentrated solution from step 2, to induce crystallization of Form 1 of Compound I.
4. exchanging the solvent to a suitable solvent to a solvent/Compound N ratio by volume (milliliter)/ weight (gram) about 6:1 to about 10:1, preferably from about 7.5:1 to about 8.5:1, more preferably about 8:1, at a temperature from about 20° C. to about 80° C., preferably from about 45° C. to about 55° C., and more preferably about 50° C., and the said suitable solvent includes but not limited to anisole, toluene, xylene, ethyl acetate, isopropyl acetate, and mixtures of two or more thereof. Preferably the suitable solvent is the mixture of toluene and ethyl acetate.

5. cooling to a temperature of about 0° C. to about 50° C., preferably from about 20° C. to about 30° C., and more preferably about 25° C.; and
6. filtering the resulting suspension to provide Form 1 of Compound I.

In one embodiment, step 1 is carried out at a suitable temperature, such as for example from about −10° C. to about 10° C., preferably from about −5° C. to about 5° C., and more preferably about 0° C. In one embodiment, preparing a solution of Compound I takes place for a period from about 30 minutes to about 2 hours, preferably about 1 hour.

In one embodiment of step 1, suitable solvents include, but are not limited to, acetonitrile, acetone, dichloromethane, dichloroethane, N,N-dimethylformamide, dimethyl sulfoxide, N-methyl-2-pyrrolidone, dioxane, ethyl acetate, heptane, hexane, methyl t-butyl ether, tetrahydrofuran, toluene, and mixtures of two or more thereof. A preferred solvent is ethyl acetate. Suitable dehydration reagents include but are not limited to, n-propylphosphonic anhydride (T3P), trifluoroacetic anhydride (TFAA), methyl N-(triethylammoniumsulfonyl)carbamate (Burgess reagent), phosphorus oxide ($P_2O_5$). A preferred dehydration reagent is trifluoroacetic anhydride (TFAA). Suitable bases include, but are not limited to, triethylamine, diisopropylethylamine, N-methylmorpholine, 1,8-diazabicyclo(5.4.0) undec-7-ene (DBU), imidazole, pyridine, 2,6-lutidine, ethyl nicotinate, N-methylpiperazine, or 1-methylimidazole. A preferred base is triethylamine.

In certain embodiment, the invention provides a method of preparing Form 1 of Compound I by precipitation, wherein said the method comprises the steps of:

i. adding Compound I to a first solvent, such as, but not limited to, ethanol, isopropyl alcohol, ethyl acetate, isopropyl acetate, or methyl tert-butyl ether, to produce a solution; the Compound I used to form the solution can be solid form of the compound or a mixture of two or more solid forms;
ii. removing a portion of the first solvent from the solution, for example by distillation; and then adding more of the first solvent;
iii. repeating removing a portion of the first solvent from the solution and adding more of the first solvent until a solution of Compound I is produced with residual solvent controlled at no greater than a predetermined value, for example not more than 0.1% (wt/wt);
iv. adding a second solvent, such as, but not limited to, water or n-heptane to the solution to precipitate the Form 1 of Compound I; and
v. isolating the Form 1 of Compound I by filtration.

Figure 8:
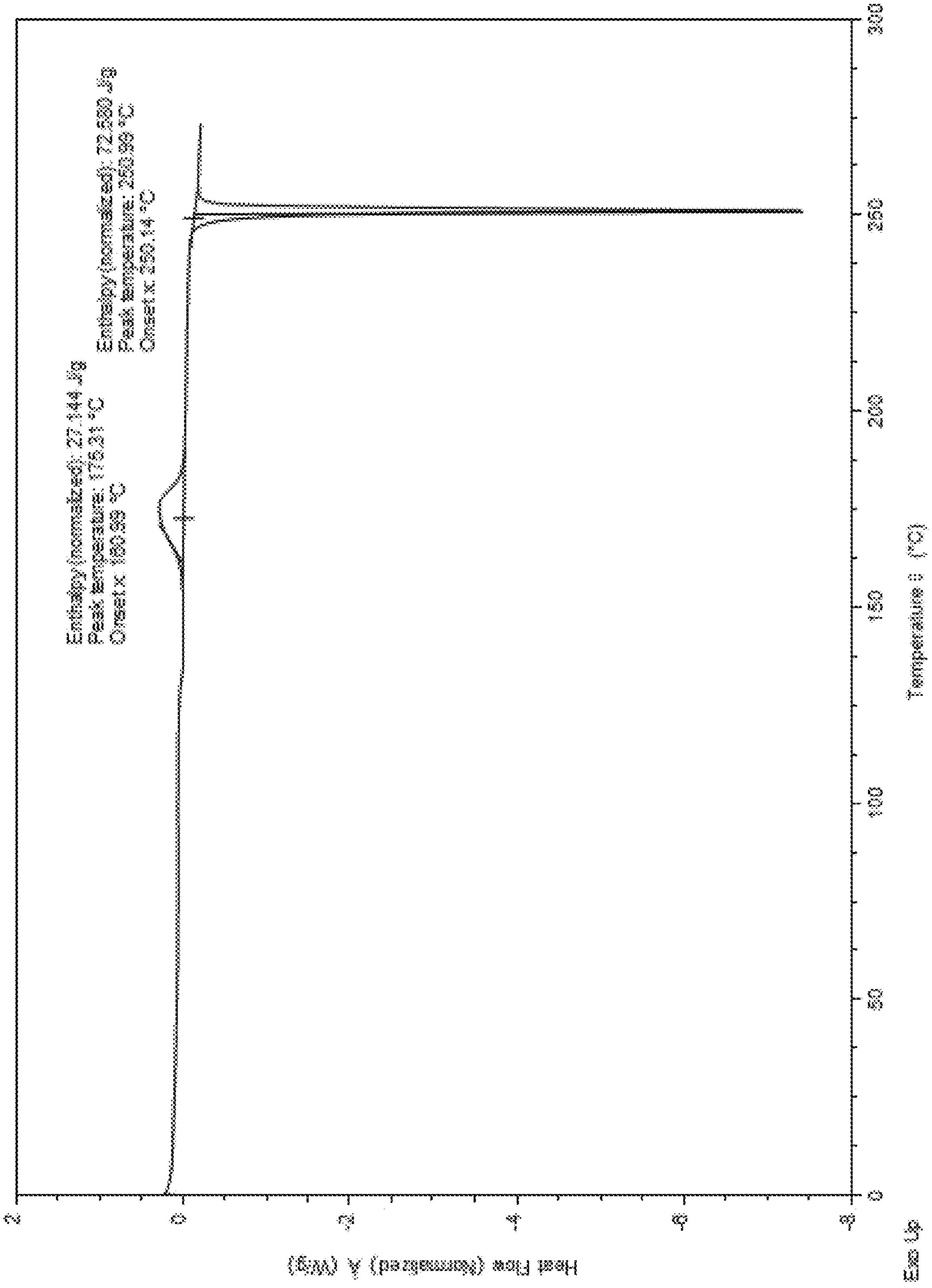
FIG. 8 is the DSC thermogram of Form 2 of Compound I.

The DSC thermogram of Form 2 is shown in FIG. 8. The DSC thermogram has a characteristic exotherm at 175° C. with an onset temperature at 175° C. and an endotherm at 251° C. with an onset temperature at 250° C.

Figure 7:
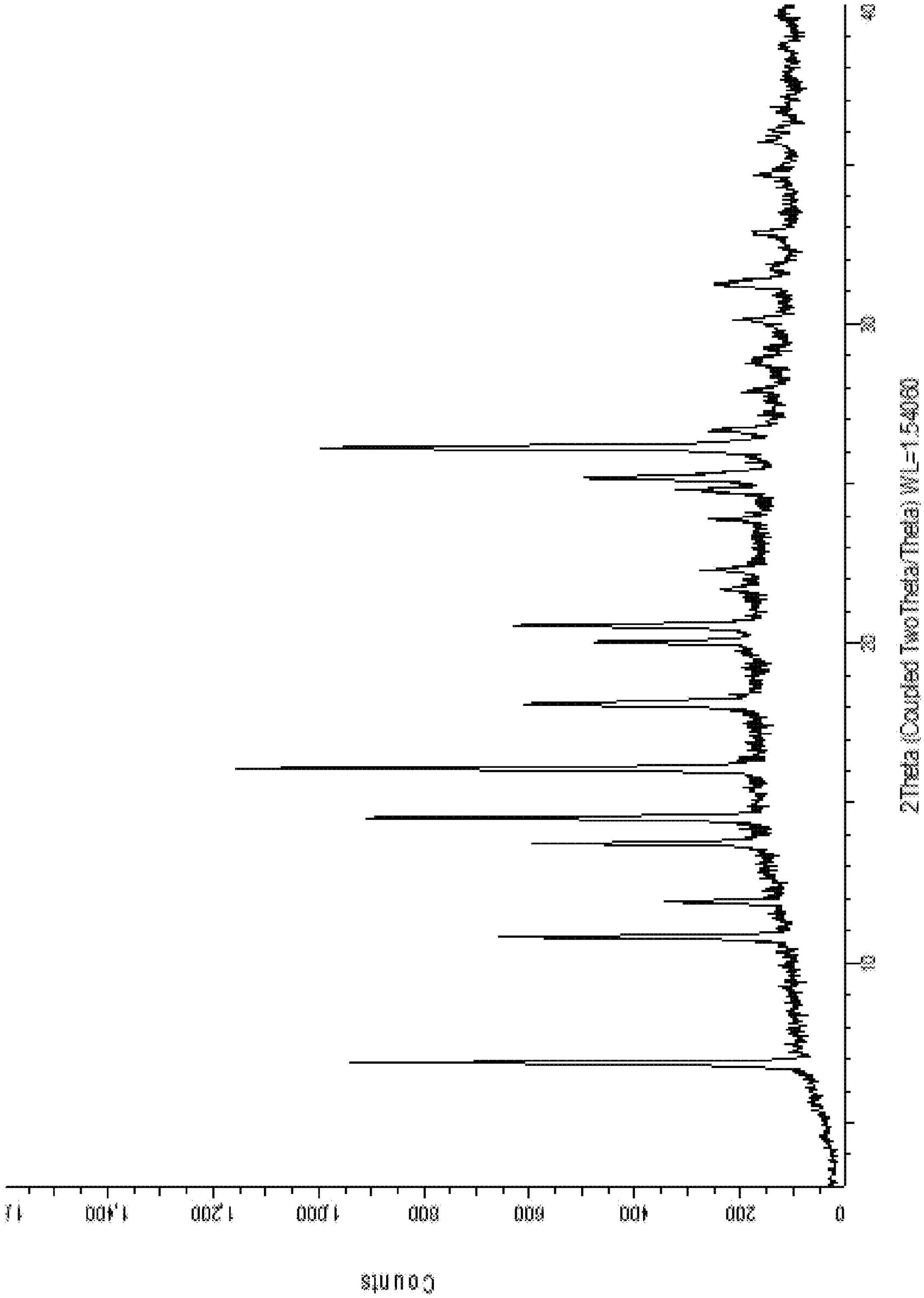
FIG. 7 is the XRPD pattern of Form 2 of Compound I.

In one embodiment, the characteristic peaks (2θ) in the X-ray powder diffraction pattern of Form 2 are shown in FIG. 7. The characteristic peaks are at values of two theta (2θ) of 6.88, 10.82, 11.90, 13.74, 14.54, 16.08, 18.10, 20.04, 20.56, 21.68, 22.29, 23.87, 24.80, 25.18, 26.12, 26.67, 27.93, 28.77, 29.23, 30.13, 31.25, 32.84, 34.28, 34.66, 35.71, 36.07, 37.10, and 39.66. The characteristic peaks can alternatively be represented as (2θ) 6.9, 10.8, 11.9, 13.7, 14.5, 16.1, 18.1, 20.0, 20.6, 21.7, 22.3, 23.9, 24.8, 25.2, 26.1, 26.7, 27.9, 28.8, 29.2, 30.1, 31.3, 32.8, 34.3, 34.7, 35.77, 36.1, 37.1, and 39.9.

In one embodiment, the present invention provides a process for preparing Form 2 of Compound I. The method comprises the step of heating form J of Compound I to a temperature from about 140° C. to about 170° C., preferably from about 150° C. to about 160° C., and more preferably about 155° C., to provide Form 2 of Compound I.

Figure 10:
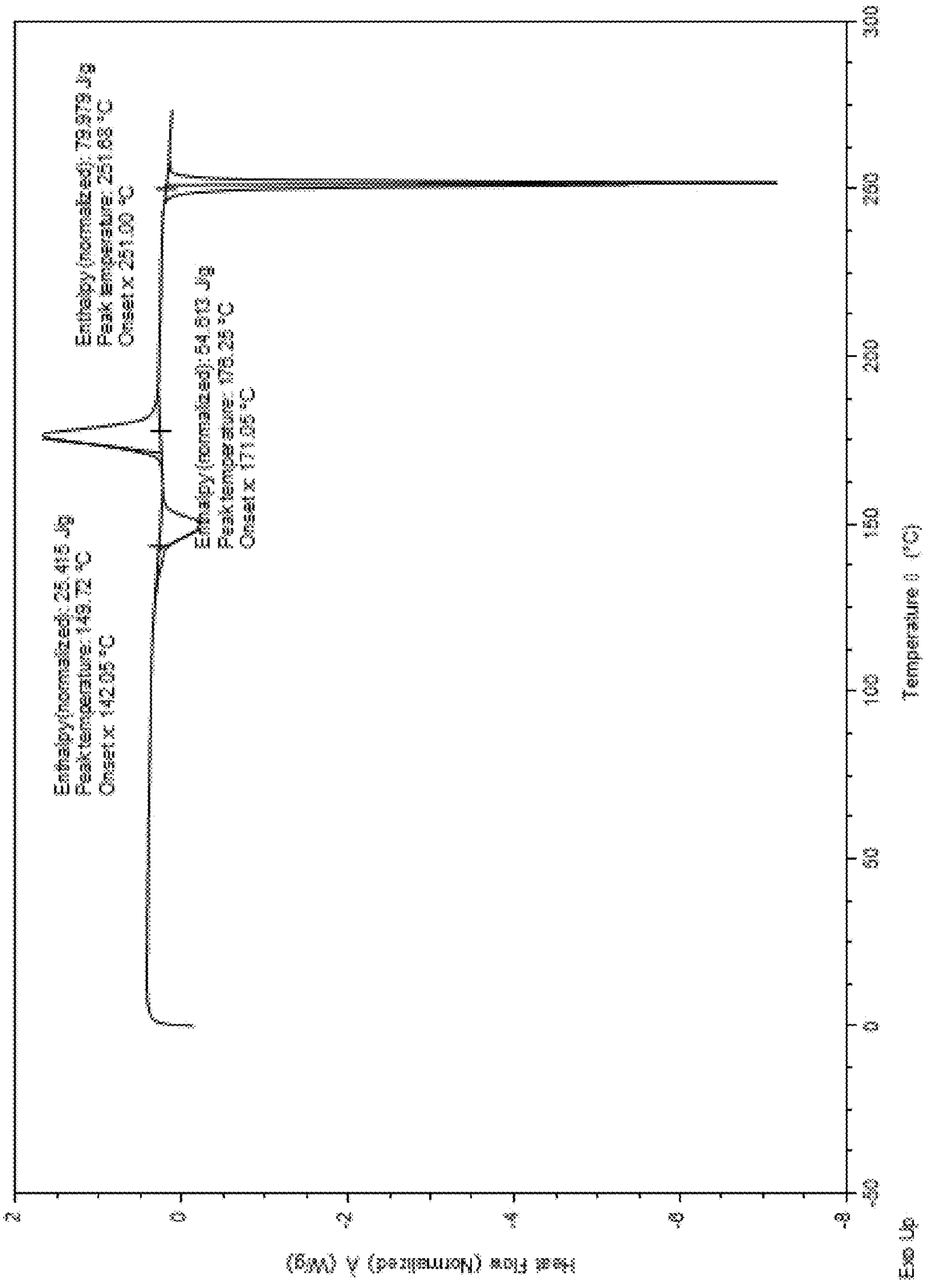
FIG. 10 is the DSC thermogram of Form 3 of Compound I.

The DSC thermogram of Form 3 is shown in FIG. 10. The DSC thermogram of Form 3 has a characteristic endotherm at 150° C. with an onset temperature at 142° C. The DSC thermogram of Form 3 also has a characteristic exotherm at 176° C. with an onset temperature at 171° C. followed by an endotherm at 252° C. with an onset temperature at 251° C.

Figure 9:
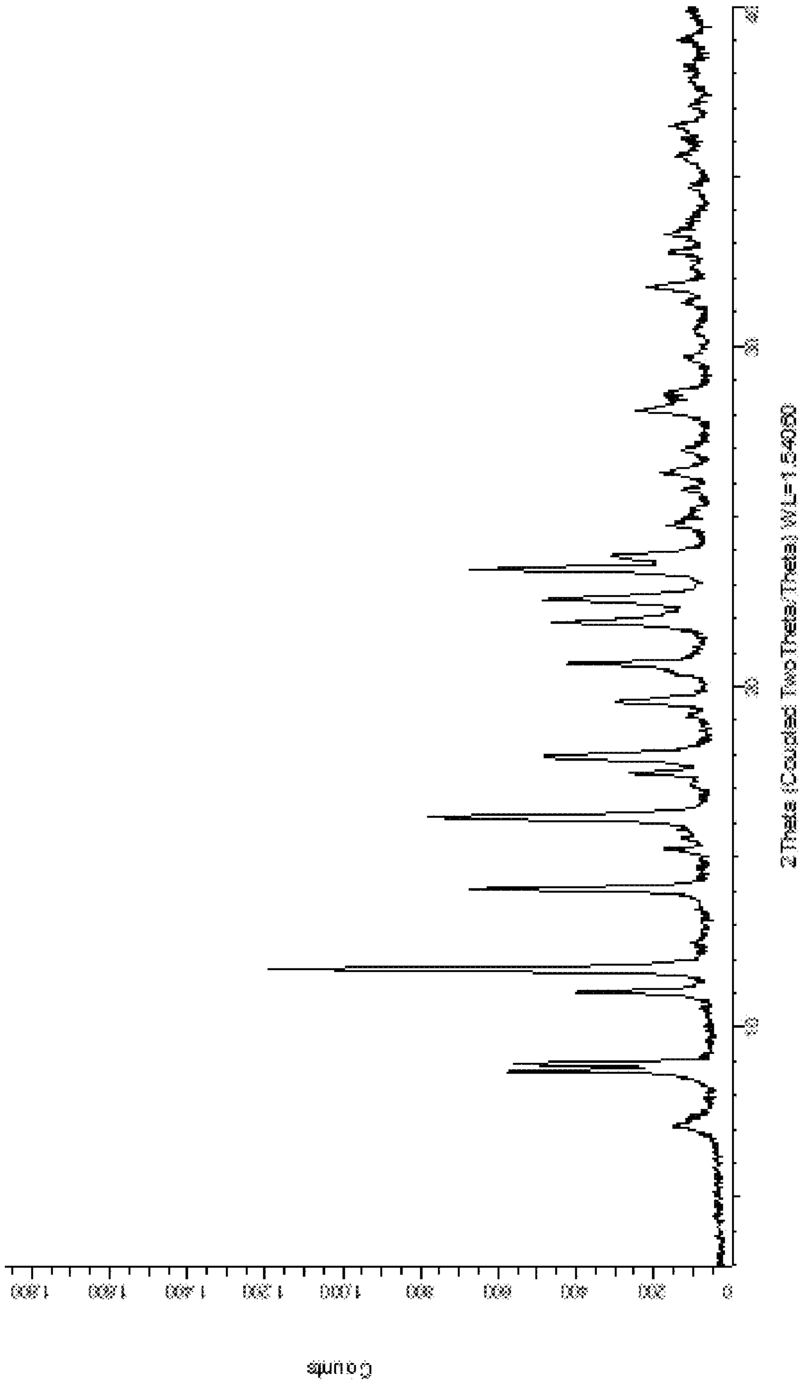
FIG. 9 is the XRPD pattern of Form 3 of Compound I.

The characteristic peaks (2θ) in the X-ray powder diffraction pattern of Form 3 are shown in FIG. 9. The characteristic peaks are at values of two theta (2θ) of 7.10, 8.71, 8.92, 11.03, 11.70, 13.07, 14.06, 15.23, 15.55, 16.17, 17.14, 17.45, 17.96, 19.16, 19.56, 20.43, 20.68, 21.89, 22.56, 23.45, 23.83, 24.74, 25.79, 26.26, 26.95, 28.12, 28.64, 29.68, 30.44, 31.28, 31.76, 32.34, 32.79, 33.30, 34.67, 35.56, 36.11, 36.47, 37.07, 37.85, and 38.22. The characteristic peaks can alternatively be represented as (2θ) 7.1, 8.7, 8.9, 11.0, 11.7, 13.1, 14.1, 15.2, 15.6, 16.2, 17.1, 17.5, 18.0, 19.2, 19.6, 20.4, 20.7, 21.9, 22.6, 23.5, 23.8, 24.7, 25.8, 26.3, 27.0, 28.1, 28.6, 29.7, 30.4, 31.3, 31.8, 32.3, 32.8, 33.3, 34.7, 35.6, 36.1, 36.5, 37.1, 37.9, and 38.2.

Figure 11:
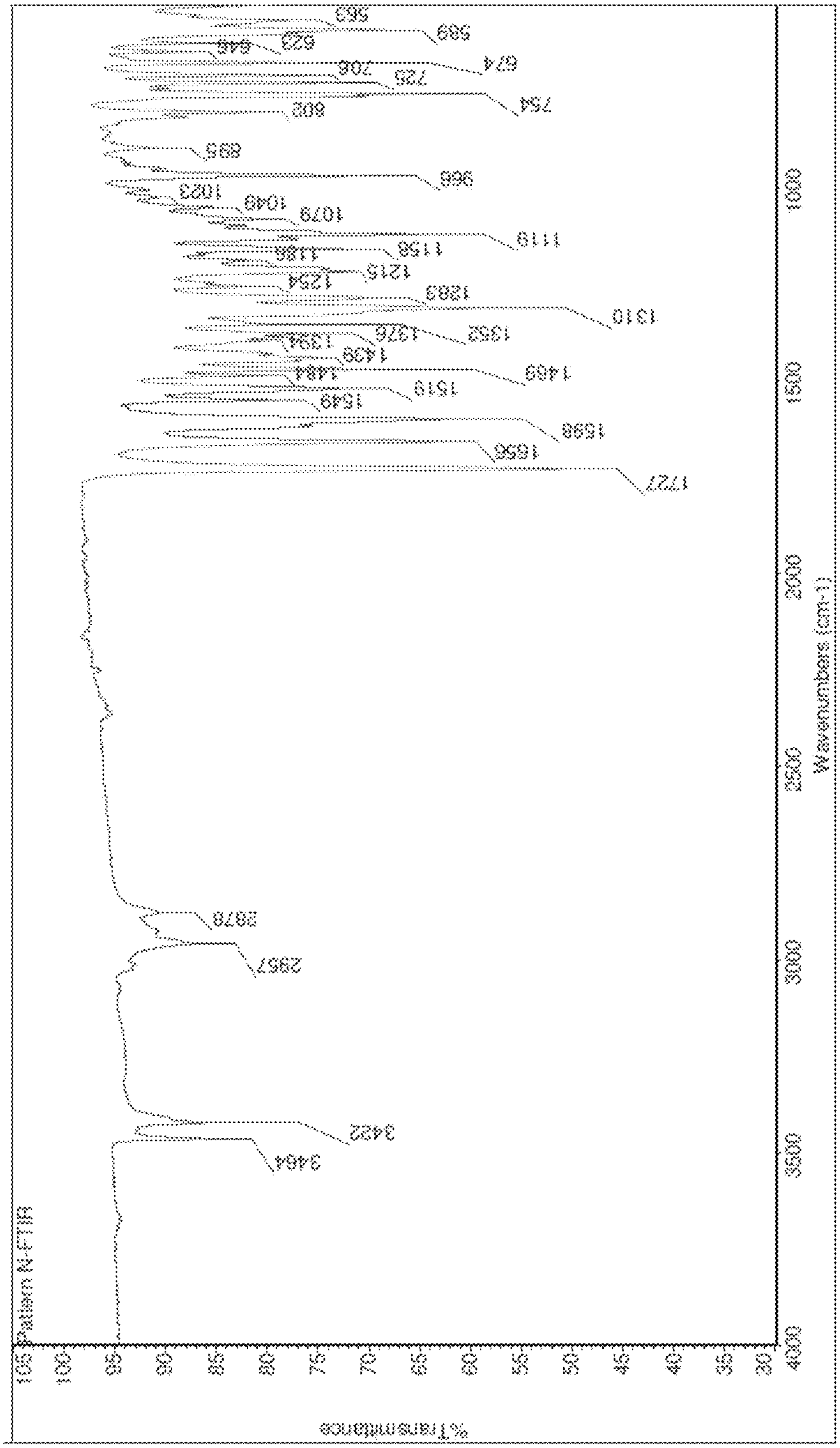
FIG. 11 is the FT-IR spectrum of Form 3 of Compound I.

The characteristic peaks of the Fourier-transform infrared (FT-IR) spectrum of the crystalline Form 3 are shown in FIG. 11. The characteristic peaks in wave numbers ($cm^{-1}$) are at 563, 589, 623, 646, 674, 706, 725, 740, 754, 802, 815, 966, 1023, 1049, 1079, 1096, 1119, 1130, 1158 1186, 1215, 1254, 1283, 1310, 1352, 1376, 1385, 1394, 1439, 1469, 1484, 1519, 1549, 1598, 1656, 1727 2878, 2957, 3422, and 3464.

In one embodiment, the present invention provides a process for preparing Form 3 of Compound I. The method comprises the step of heating Form J of Compound I to a temperature from about 70° C. to about 100° C., preferably from about 75° C. to about 85° C., and more preferably about 80° C. to provide Form 3 of Compound I.

Figure 12:
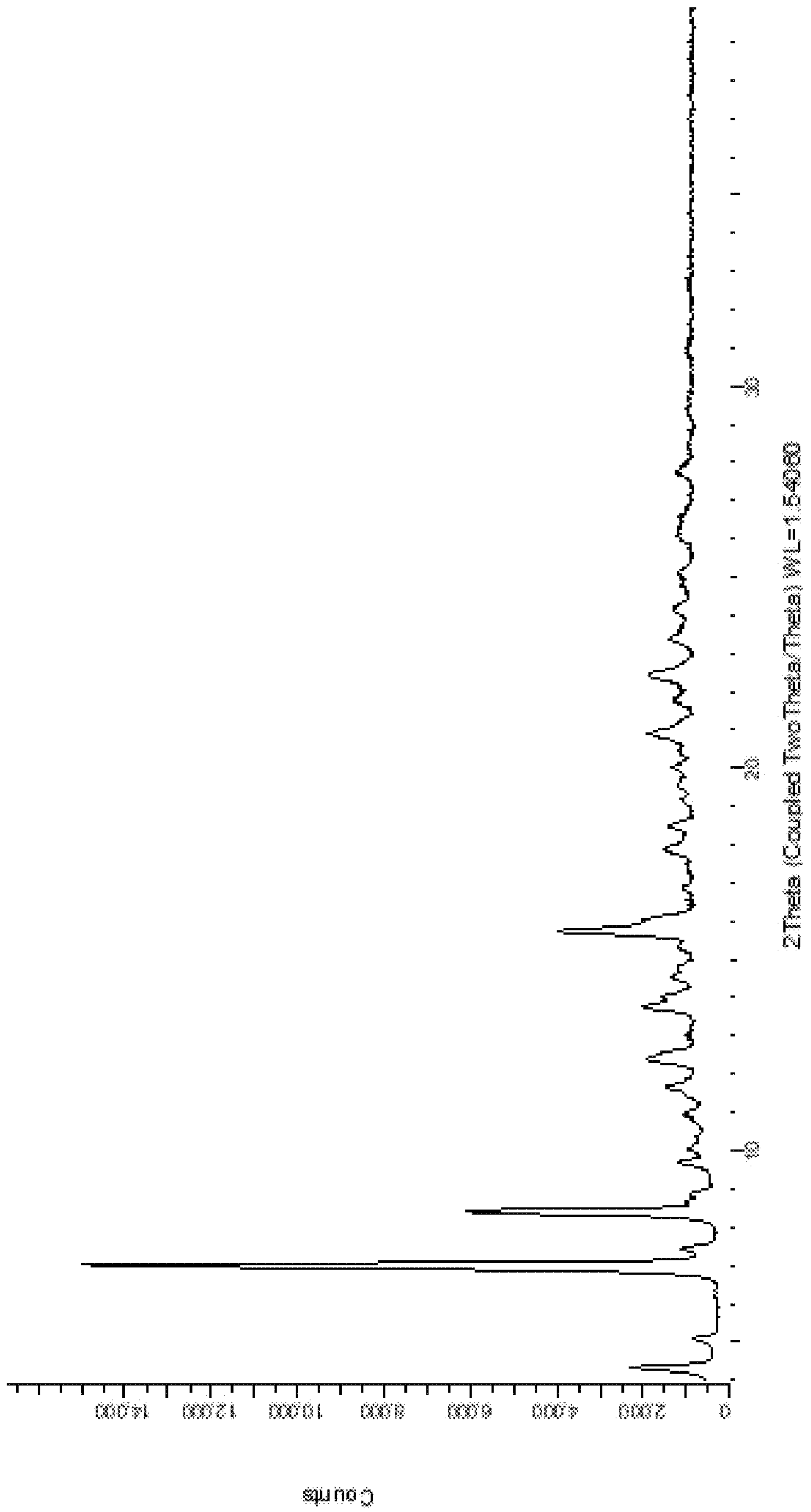
FIG. 12 is the XRPD pattern of Form 4 of Compound I.

The characteristic peaks (2θ) in X-ray powder diffraction pattern of Form 4 are shown in FIG. 12. Form 4 has characteristic peaks in the X-ray powder diffraction (XRPD) pattern at values of two theta (2θ) of 4.39, 5.14, 7.06, 7.50, 8.47, 8.92, 9.75, 10.08, 10.33, 11.03, 11.71, 12.45, 13.09, 13.83, 14.06, 14.62, 14.84, 15.38, 15.78, 15.95, 16.91, 17.45, 17.93, 18.54, 19.23, 19.66, 20.07, 20.96, 21.84, 22.50, 23.42, 24.19, 24.91, 25.13, 26.18, 26.54, 27.81, 28.54, 29.41, and 30.99. The characteristic peaks can alternatively be represented as (2θ) 4.4, 5.1, 7.1, 7.5, 8.5, 8.9, 9.8, 10.1, 10.3, 11.0, 11.7, 12.5, 13.1, 13.8, 14.1, 14.6, 14.8, 15.4, 15.8, 16.0, 16.9, 17.5, 17.9, 18.5, 19.2, 19.7, 20.1, 21.0, 21.8, 22.5, 23.4, 24.2, 24.9, 25.1, 26.2, 26.5, 27.8, 28.5, 29.4, and 31.0.

In one embodiment, the present invention provides a method of preparing Form 4 of Compound I. The method comprises the step of heating form J of Compound I to a temperature from about 40° C. to about 70° C., preferably from about 55° C. to about 65° C., and more preferably about 60° C. to provide Form 4 of Compound I.

Figure 14:
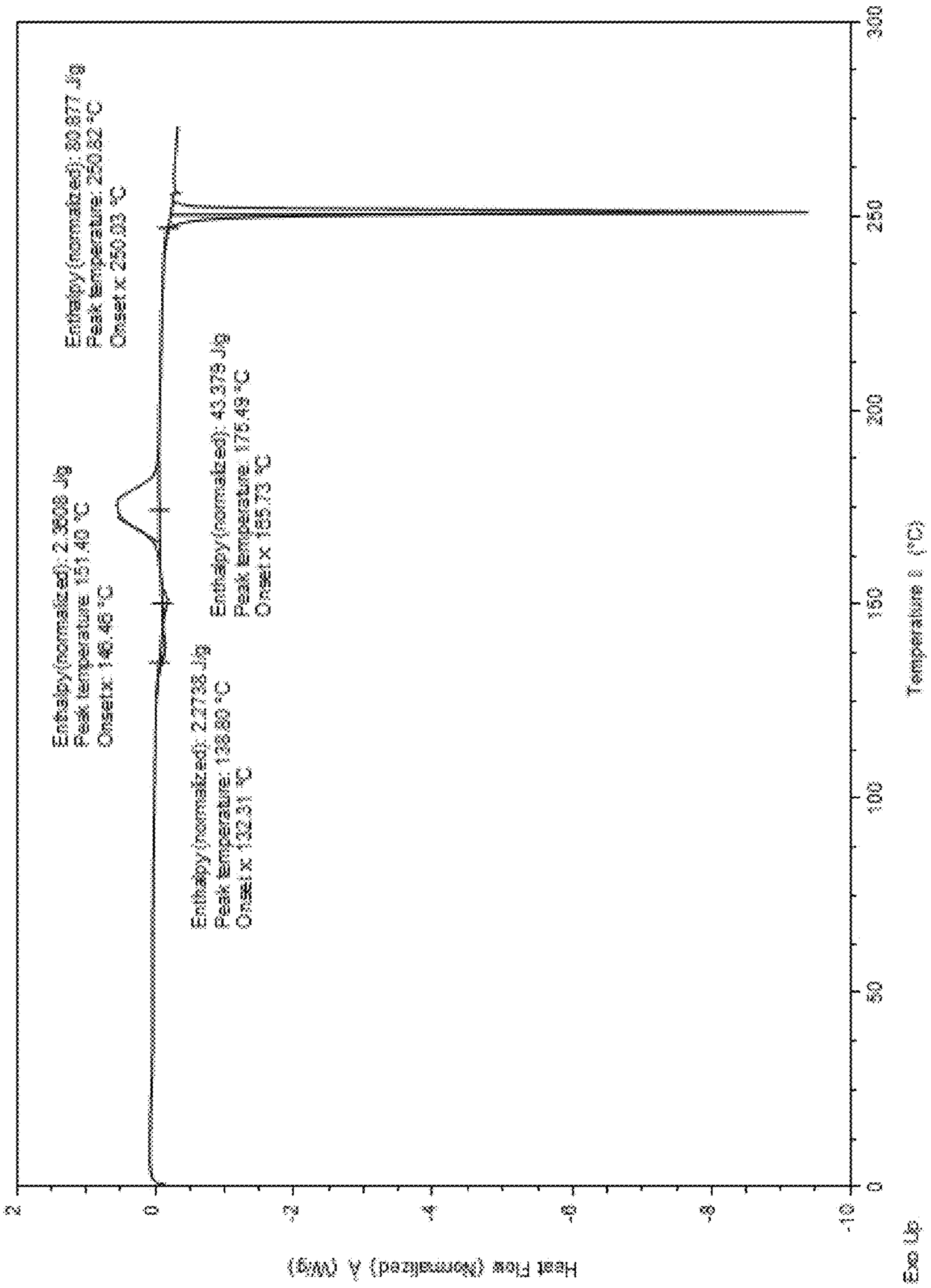
FIG. 14 is the DSC thermogram for a mixture of Form 2 and Form 4 of Compound I.

The DSC thermogram of the mixture of Form 2 and Form 4 is shown in FIG. 14. The DSC thermogram has both a characteristic melting endotherm at 175° C. with an onset temperature at 166° C. and an endotherm at 139° C. with an onset temperature at 132° C. The DSC thermogram also has a characteristic exotherm at 151° C. with an onset temperature at 147° C. followed by an endotherm at 251° C. with an onset temperature at 250° C.

Figure 13:
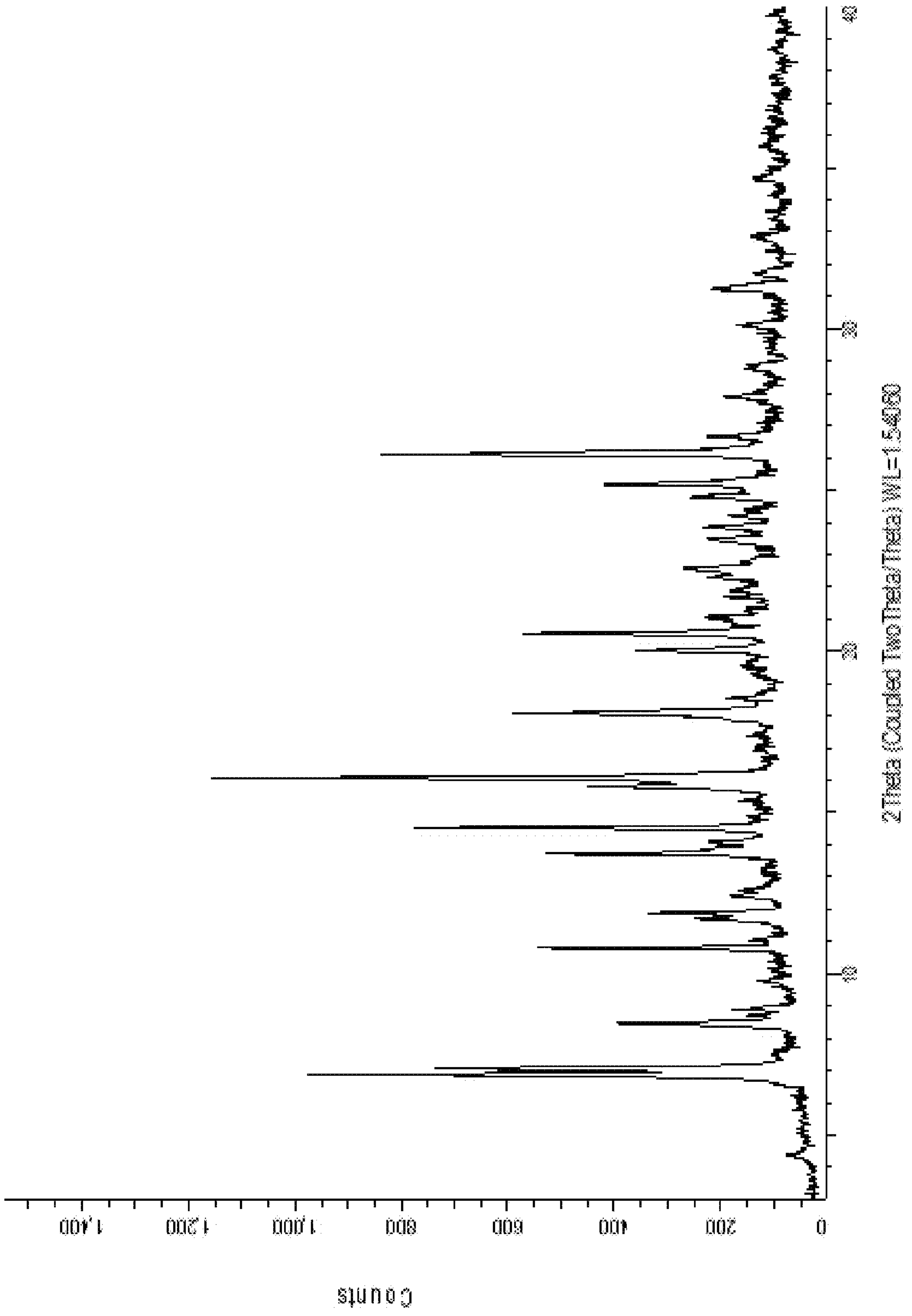
FIG. 13 is the XRPD pattern for a mixture of Form 2 and Form 4 of Compound I.

The characteristic peaks (2θ) in X-ray powder diffraction pattern of the mixture of Form 2 and Form 4 are shown in FIG. 13. The characteristic peaks (2θ) are at 4.36, 6.87, 7.06, 8.46, 8.71, 8.92, 9.77, 10.80, 11.04, 11.72, 11.89, 12.43, 12.58, 13.73, 14.06, 14.53, 15.81, 16.07, 18.08, 18.55, 20.03, 20.56, 21.06, 21.68, 21.87, 22.30, 22.58, 23.44, 23.86, 24.21, 24.79, 25.18, 26.11, 26.66, 27.90, 30.11, 31.25, 31.72, 32.88, and 35.72. The characteristic peaks can alternatively be represented as (2θ) 4.4, 6.9, 7.1, 8.5, 8.7, 8.9, 9.8, 10.8, 11.0, 11.7, 11.9, 12.4, 12.6, 13.7, 14.1, 14.5, 15.8, 16.1, 18.1, 18.6, 20.0, 20.6, 21.1, 21.7, 21.9, 22.3, 22.6, 23.4, 23.9, 24.2, 24.8, 25.2, 26.1, 26.7, 27.9, 30.1, 31.3, 31.7, 32.9, and 35.7.

In one embodiment, the present invention provides a method of preparing a mixture of Form 2 and Form 4 of Compound I. The method comprises the step of heating form J of Compound I to a temperature from about 100° C. to about 140° C., preferably from about 120° C. to about 130° C., and more preferably about 125° C. to provide the mixture of Form 2 and Form 4 of Compound I.

Figure 16:
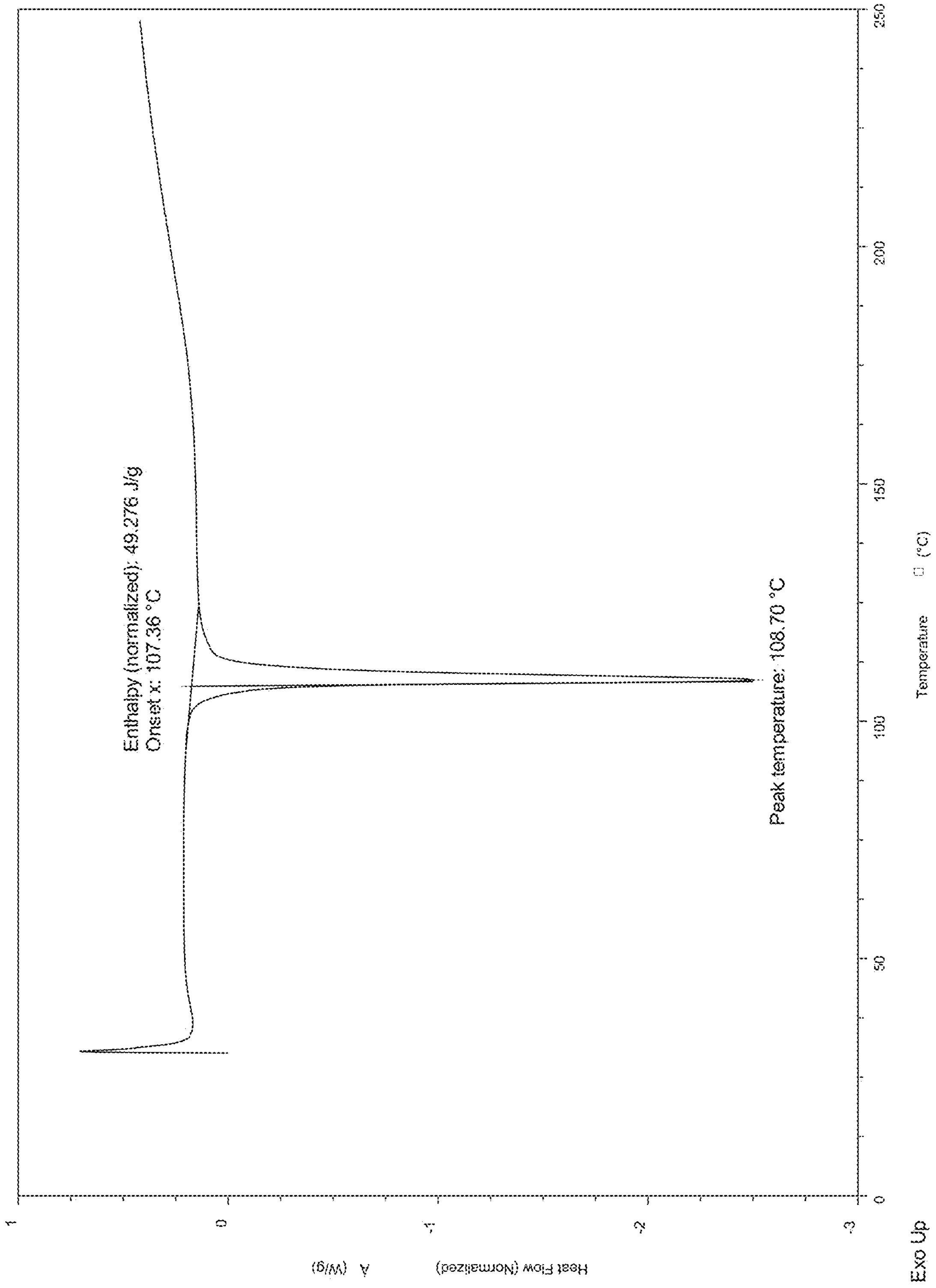
FIG. 16 is the DSC thermogram of Form A of Compound I.

The DSC thermogram of Form A of Compound I is shown in FIG. 16. The DSC of Form A has characteristic endotherm at 109° C. with an onset temperature at 107° C.

Figure 15:
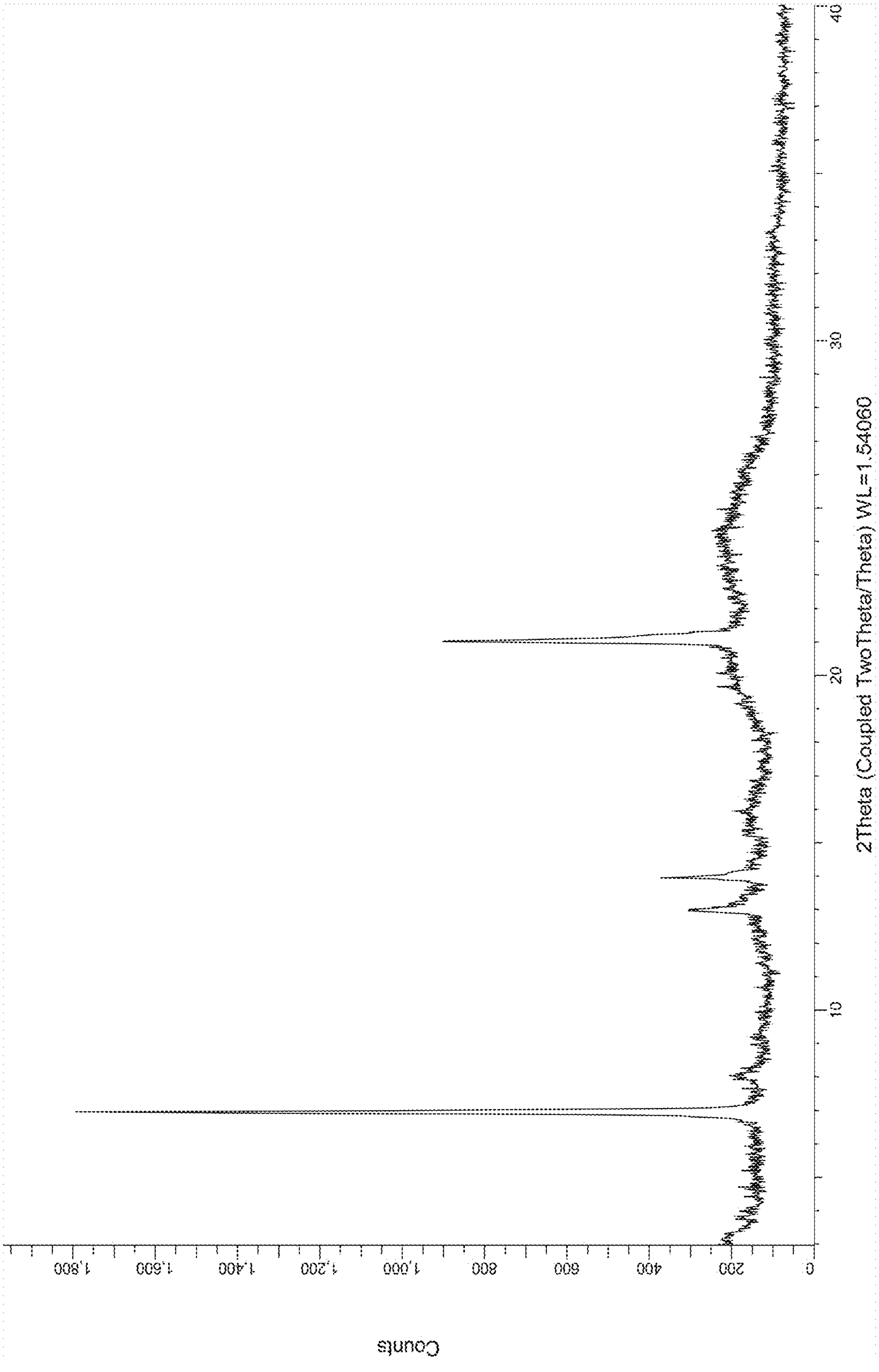
FIG. 15 is the XRPD pattern of Form A of Compound I.

The characteristic peaks (2θ) in X-ray powder diffraction pattern of Form A are shown in FIG. 15. The characteristic peaks are at values of two theta (2θ) of: 6.96, 8.05, 13.00, 13.97, and 21.03. The characteristic peaks can alternatively be represented as (2θ) 7.0, 8.1, 13.0, 14.0, and 21.0.

In one embodiment, the present invention provides a method for preparing Form A of Compound I. The method comprises the steps of:

i. preparing a suspension of the amorphous form of Compound I in a mixture of benzyl alcohol and toluene in a volume ratio from about 1:1 to about 4:1;
ii. heating and subsequent cooling of the suspension between about 5° C. and 50° C. for multiple cycles for about 1 to 20 days, preferably about 12 days, to obtain a suspension of Form A of Compound I; and
iii. filtering the suspension of Form A of Compound I from step ii at a temperature between about 10° C. and 30° C., preferably from about 15° C. to about 25° C., and more preferably about 22° C. to provide Form A of Compound I.

Figure 18:
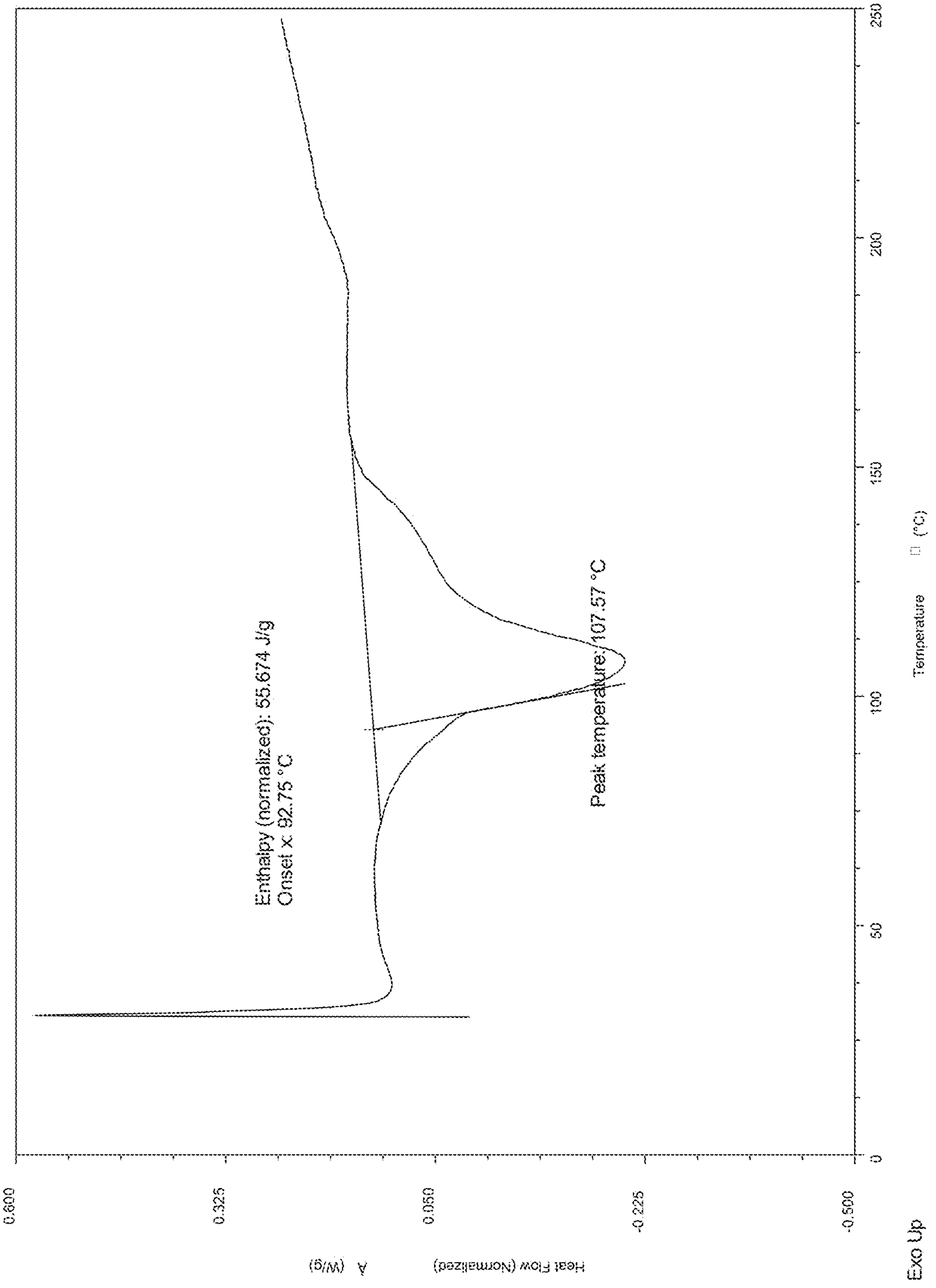
FIG. 18 is the DSC thermogram of Form B of Compound I.

The DSC thermogram of Form B of Compound I is shown in FIG. 18. The DSC thermogram of Form B has a characteristic endotherm at 108° C. with an onset temperature at 93° C.

Figure 17:
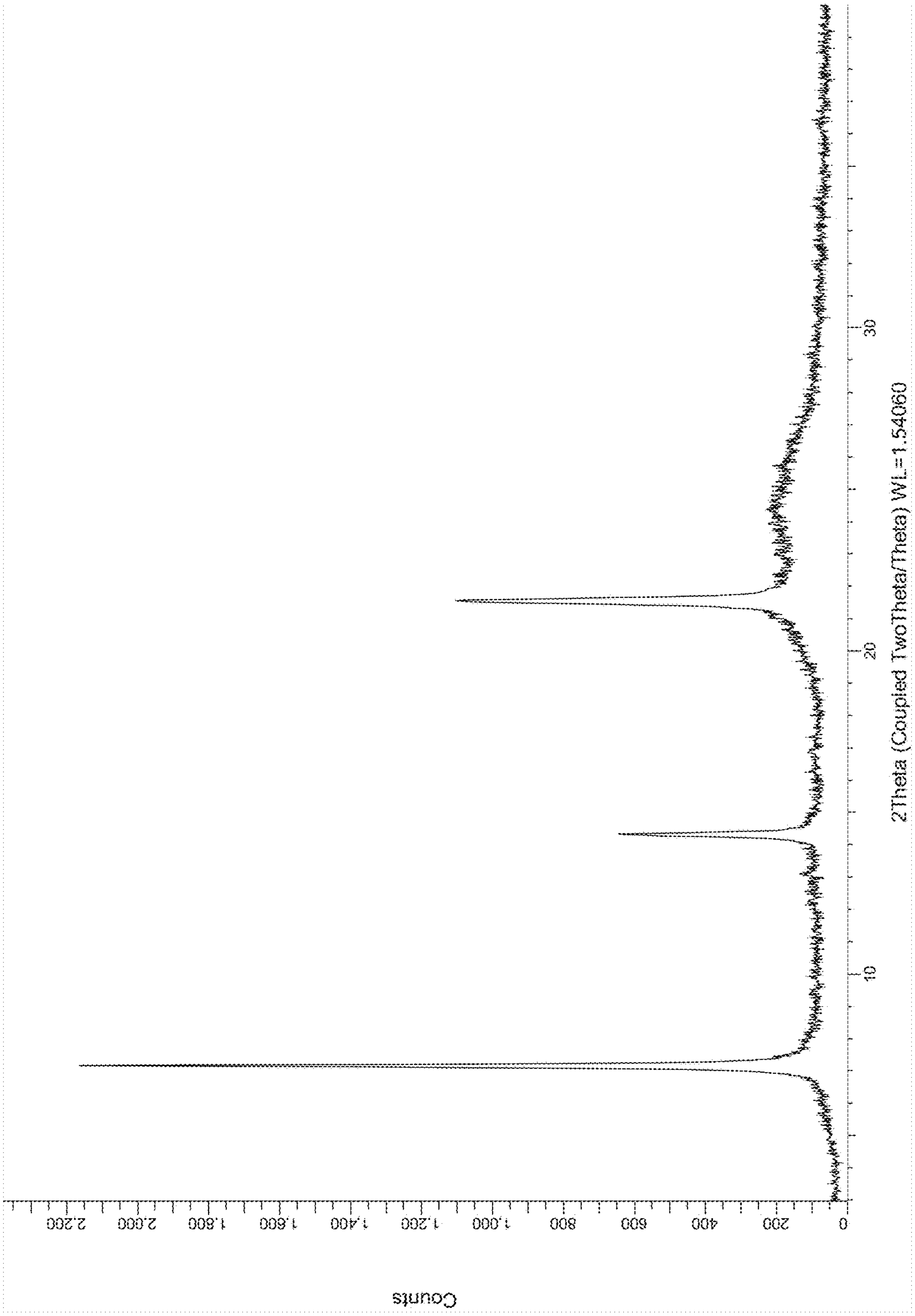
FIG. 17 is the XRPD pattern of Form B of Compound I.

The characteristic peaks (2θ) in the X-ray powder diffraction pattern of Form B are shown in FIG. 17. The characteristic peaks are at values of two theta (2θ) of 7.17, 14.33, and 21.55. The characteristic peaks can alternatively be designated as (2θ) 7.2, 14.3, and 21.6.

In one embodiment, the present invention provides a method for preparing Form B of Compound I. The method comprises the steps of:

i. preparing a suspension of the amorphous form of Compound I in anisole;
ii. heating and cooling the suspension between about 5° C. and 50° C. repeatedly for about 1 day to 10 days, preferably about 5 days, to obtain a suspension of Form B of Compound I; and
iii. Filtering the suspension at a temperature between about 10° C. and 30° C., preferably from about 15° C. to about 25° C., and more preferably about 22° C., to provide Form B of Compound I.

Figure 19:
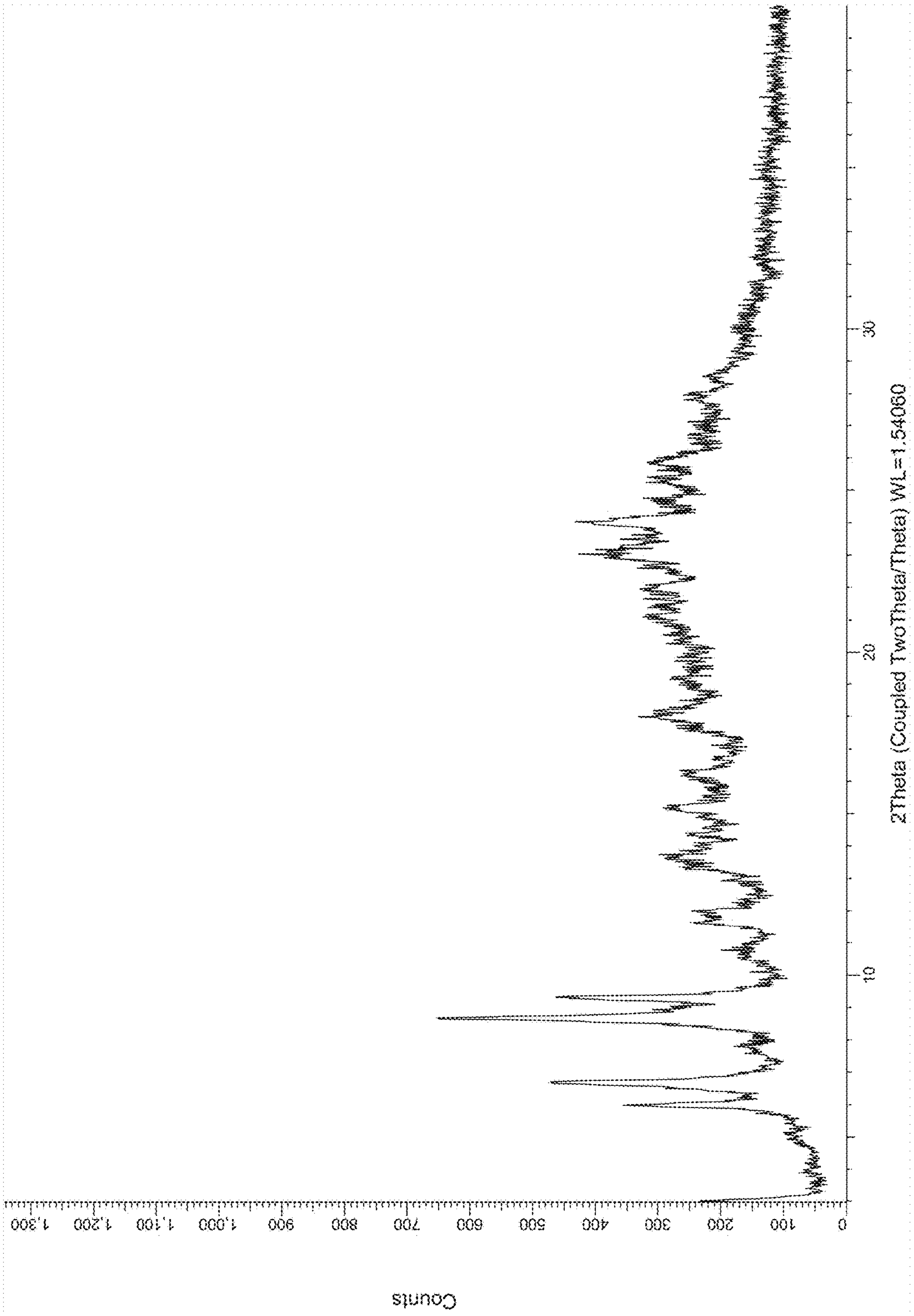
FIG. 19 is the XRPD pattern of Form C of Compound I.

The characteristic peaks (2θ) in the X-ray powder diffraction pattern of Form C are shown in FIG. 19. The characteristic peaks are at values of two theta (2θ) of 4.99, 6.01, 6.72, 7.83, 8.70, 9.33, 10.68, 10.98, 11.66, 11.90, 12.96, 13.43, 13.71, 14.01, 14.92, 15.19, 15.53, 16.28, 17.73, 18.22, 18.96, 20.44, 21.11, 21.99, 23.09, 24.06, 25.33, 25.86, 27.91, and 28.52. The characteristic peaks can alternatively be represented as (2θ) 5.0, 6.0, 6.7, 7.8, 8.7, 9.3, 10.7, 11.0, 11.7, 11.9, 13.0, 13.4, 13.7, 14.0, 14.9, 15.2, 15.5, 16.3, 17.7, 18.2, 19.0, 20.4, 21.1, 22.0, 23.1, 24.1, 25.3, 25.9, 27.9, and 28.5.

In one embodiment, the present invention provides a method for preparing Form C of Compound I. The method comprises the steps of:

i. preparing a clear solution of the amorphous form of Compound I in anisole (about 6× by volume);
ii. removing the anisole by slow evaporation between about 10° C. and 30° C., preferably from about 15° C. to about 25° C., and more preferably about 22° C., in about 1 day to 10 days, preferably about 6 days, to obtain a suspension, and
iii. filtering the suspension to provide Form C of Compound I.

Figure 21:
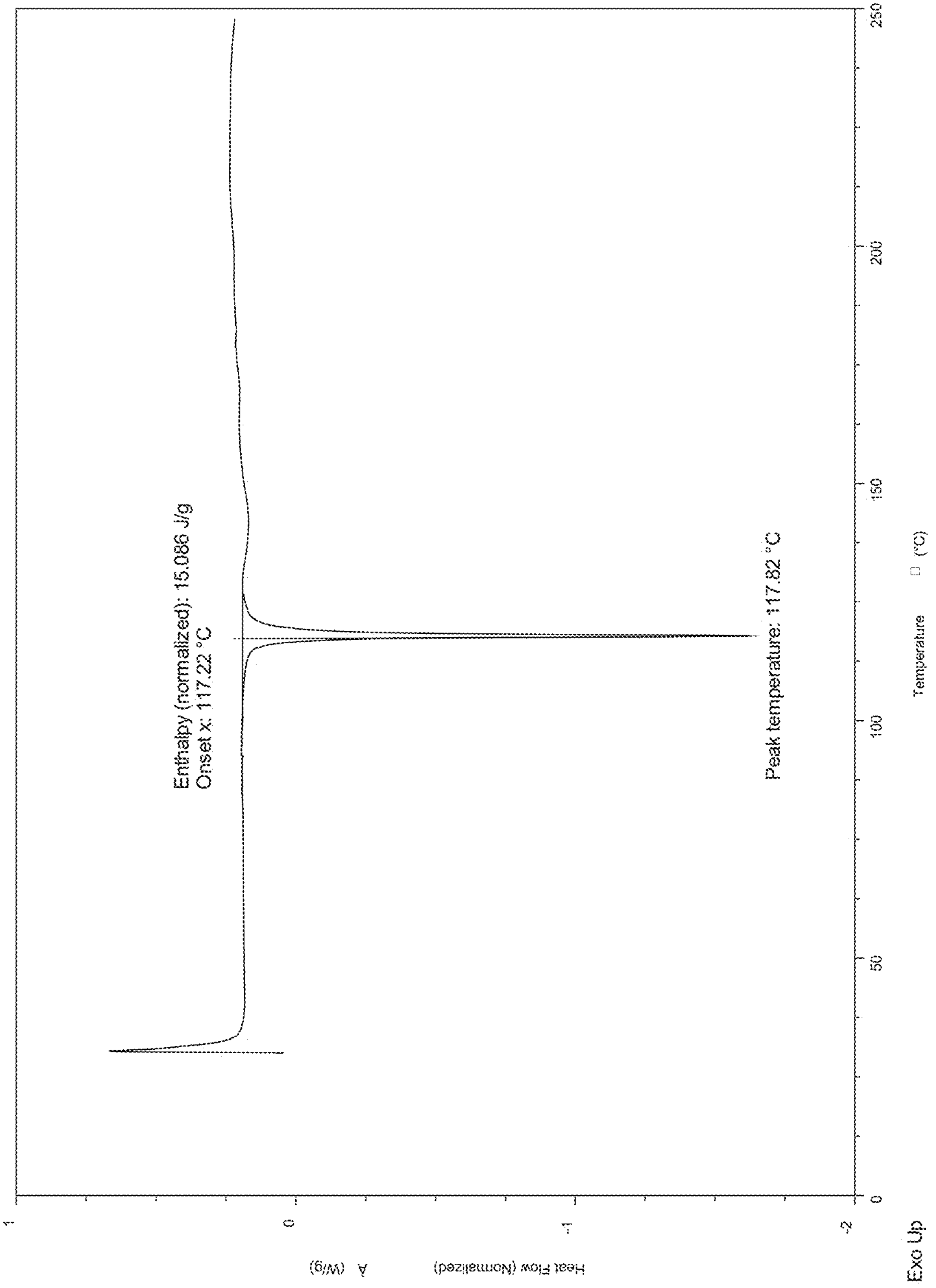
FIG. 21 is the DSC thermogram of Form D of Compound I.

The DSC thermogram of Form D of Compound I is shown in FIG. 21. The DSC thermogram of Form D has a characteristic endotherm at 118° C. with an onset temperature at 117° C.

Figure 20:
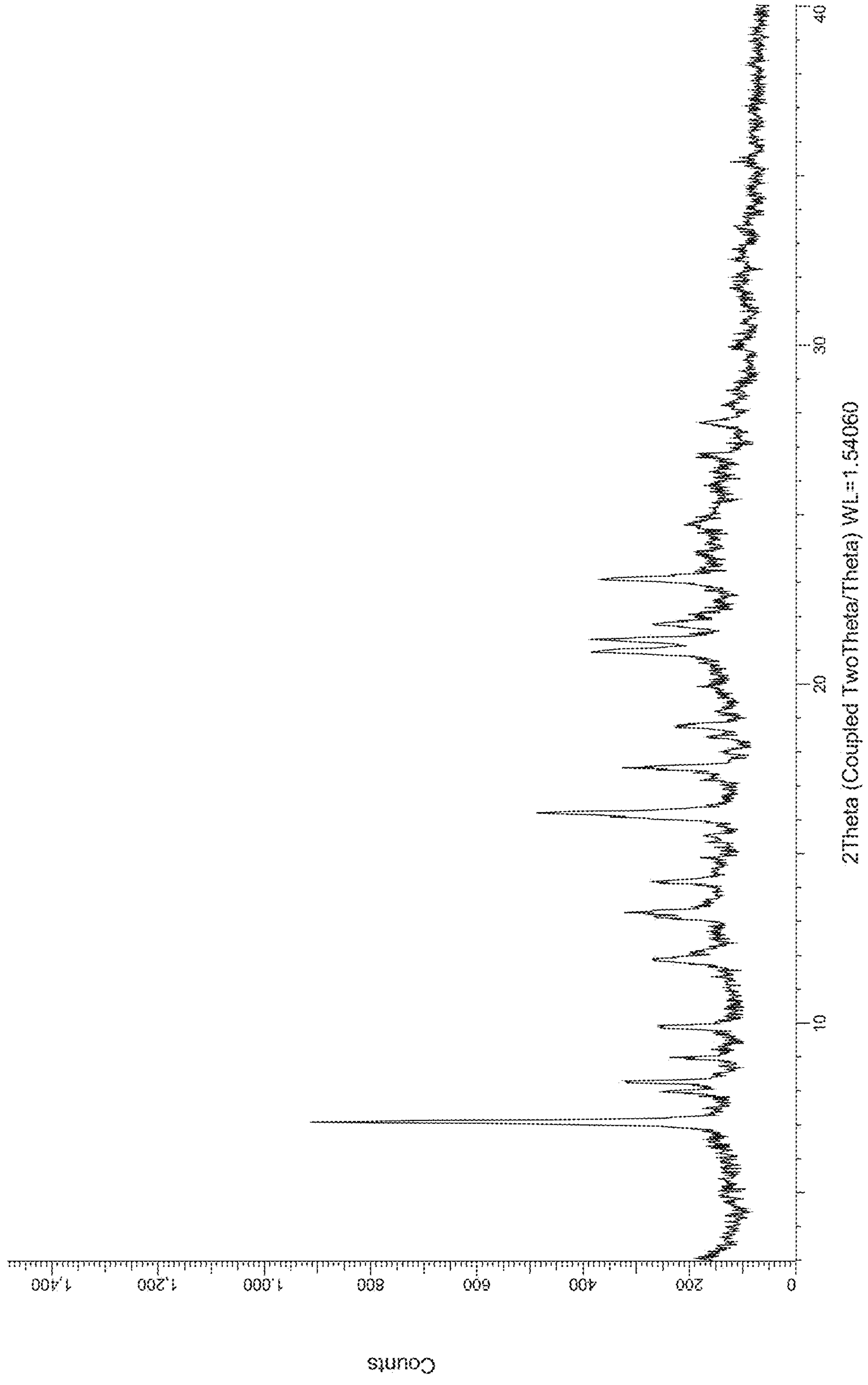
FIG. 20 is the XRPD pattern of Form D of Compound I.

In one embodiment, the characteristic peaks (2θ) in X-ray powder diffraction pattern of Form D are shown in FIG. 20. The characteristic peaks are at values of two theta (2θ) of 7.10, 7.99, 8.27, 8.98, 9.89, 11.88, 13, 14, 13.27, 14.16, 16.21, 17.55, 18.45, 18.77, 20.97, 21.32, 21.79, 23.11, 24.72, 26.71, and 27.72. The characteristic peaks can alternatively be represented as (2θ) 7.1, 8.0, 8.3, 9.0, 9.9, 11.9, 13.1, 13.3, 14.2, 16.2, 17.6, 18.5, 18.8, 21.0, 21.3, 21.8, 23.1, 24.7, 26.7, and 27.7.

Figure 22:
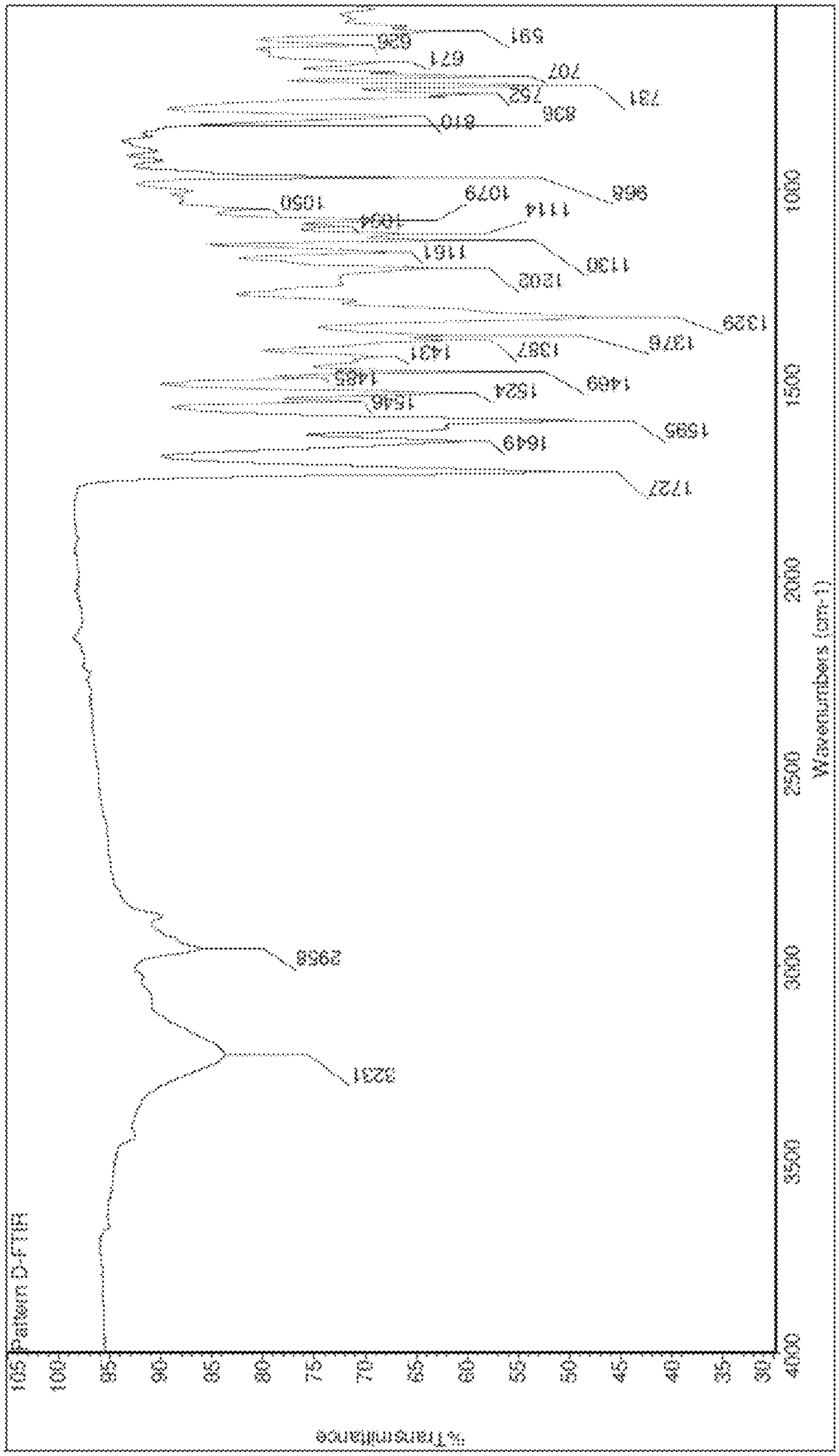
FIG. 22 is the FT-IR spectrum of Form D of Compound I.

In one embodiment, the Fourier-Transform Infrared (FT-IR) spectrum of Form D is shown in FIG. 22. The FT-IR spectrum of Form D has characteristic peaks in wave numbers ($cm^{-1}$) at 591, 626, 671, 696, 707, 731, 752, 810, 968, 1050, 1079, 1094, 1114, 1130, 1161, 1202, 1329, 1376, 1387, 1431, 1469, 1485, 1524, 1546, 1595, 1649, 1727, 2958, and 3231.

In one embodiment, the present invention includes provides a method of preparing Form D of Compound I. The method comprises the steps of:

i. preparing a suspension of Form A of Compound I in a mixed solvent comprising acetone and water;
ii. stirring the suspension at a temperature between about 10° C. and 40° C., preferably from about 20° C. to about 30° C., and more preferably about 25° C.; and
iii. filtering the suspension to provide Form D of Compound I.

Figure 24:
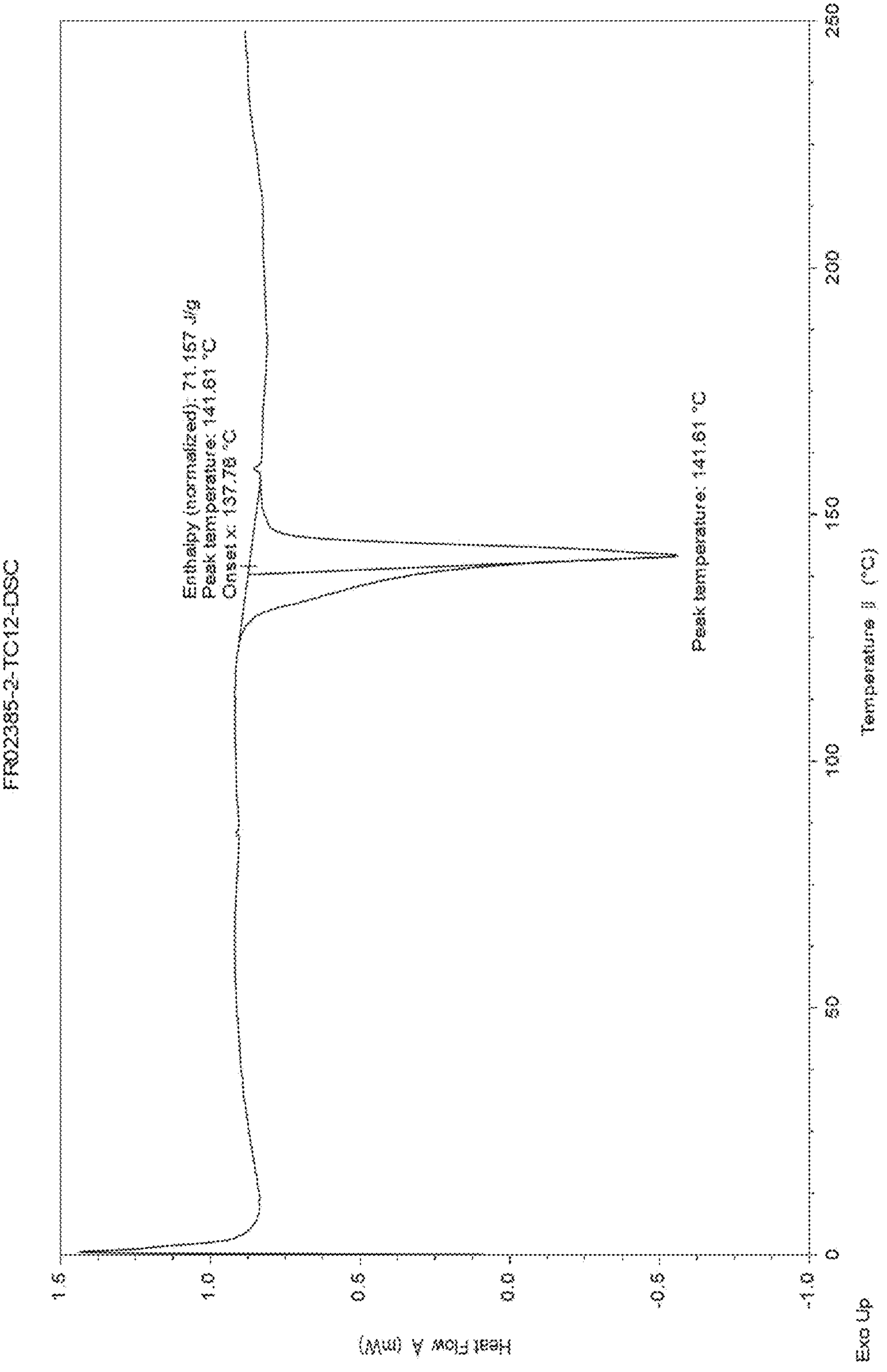
FIG. 24 is the DSC thermogram of Form E of Compound I.

The DSC thermogram of the Form E is shown in FIG. 24. The DSC thermogram of Form E has a characteristic endotherm at 142° C. with an onset temperature at 138° C.

Figure 23:
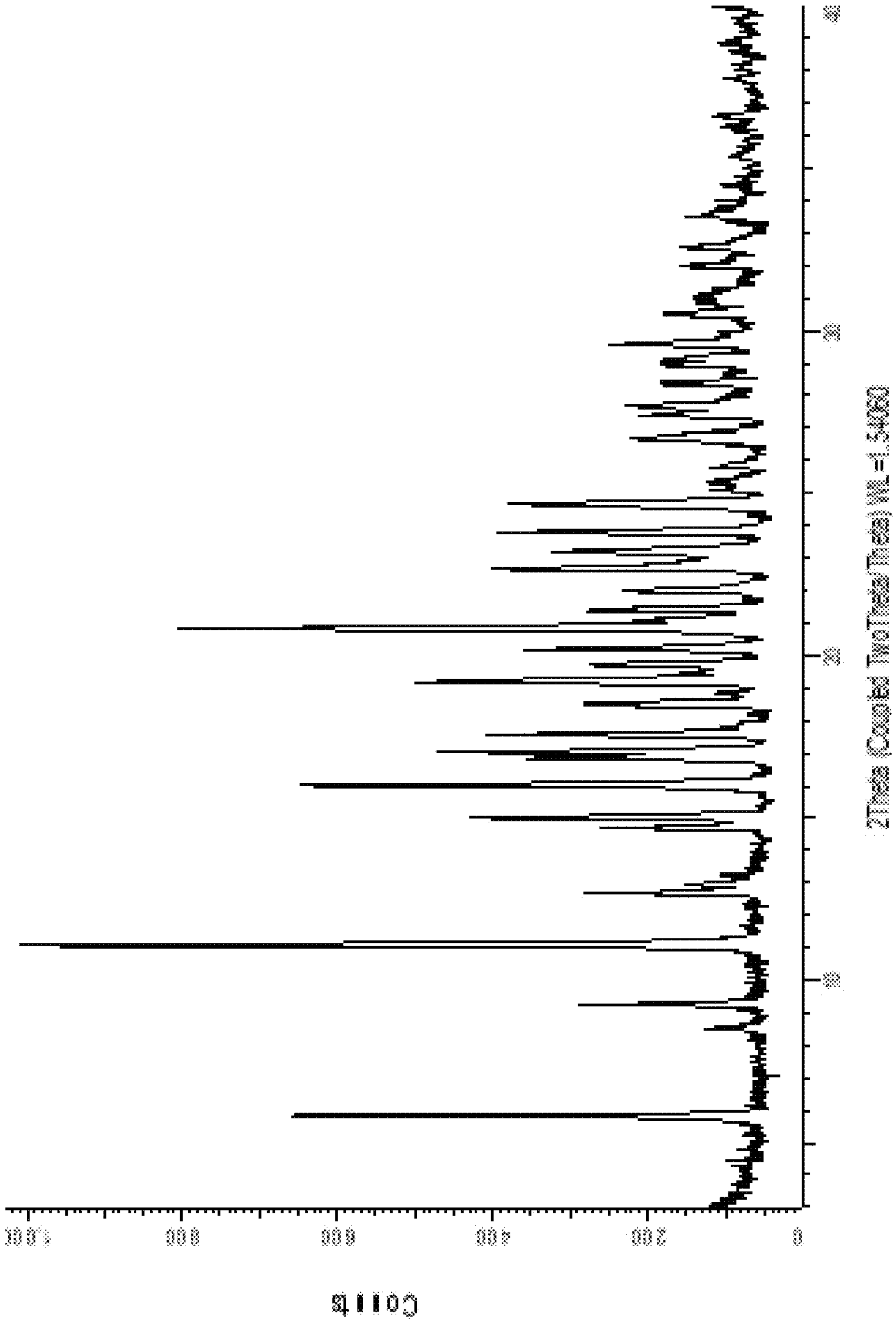
FIG. 23 is the XRPD pattern of Form E of Compound I.

The characteristic peaks (2θ) in the X-ray powder diffraction pattern of Form E are shown in FIG. 23. The characteristic peaks are at values of two theta (2θ) of 5.85, 8.52, 9.26, 11.08, 12.69, 12.95, 13.22, 14.71, 15.01, 16.01, 16.83, 17.04, 17.56, 18.54, 18.83, 19.18, 19.73, 20.19, 20.83, 21.09, 21.38, 21.99, 22.67, 23.19, 23.77, 24.67, 25.10, 25.84, 26.68, 27.40, 27.69, 28.41, 28.97, 29.60, 30.51, 30.83, 31.99, 32.56, and 33.52. The characteristic peaks can alternatively be represented as at values of two theta (2θ) of: 5.9, 8.5, 9.3, 11.1, 12.7, 13.0, 13.2, 14.7, 15.0, 16.0, 16.8, 17.0, 17.6, 18.5, 18.8, 19.2, 19.7, 20.2, 20.8, 21.1, 21.4, 22.0, 22.7, 23.2, 23.8, 24.7, 25.1, 25.8, 26.7, 27.4, 27.7, 28.4, 29.0, 29.6, 30.5, 30.8, 32.0, 32.6, and 33.5.

In one embodiment, the present invention provides a method for preparing Form E of Compound I. The method comprises the steps of:

i. preparing a suspension of Form D of Compound I in a solvent mixture comprising dimethyl sulfoxide (dimethyl sulfoxide volume/Compound I weight in about 1/1 ratio) and water (water volume/Compound I weight in about 1/1 ratio);
ii. Preferably adding about 0.0001X (X=weight of Compound I in step 1) to about 0.1X of Form E of Compound I, more preferably 0.001X by weight as seed;
iii. heating and cooling the suspension repeatedly between preferably about 5° C. and 50° C. for preferably about 15 times to 25 times, and more preferably about 20 times; and
iv. filtering the resulting suspension to provide Form E of Compound I.

Figure 25:
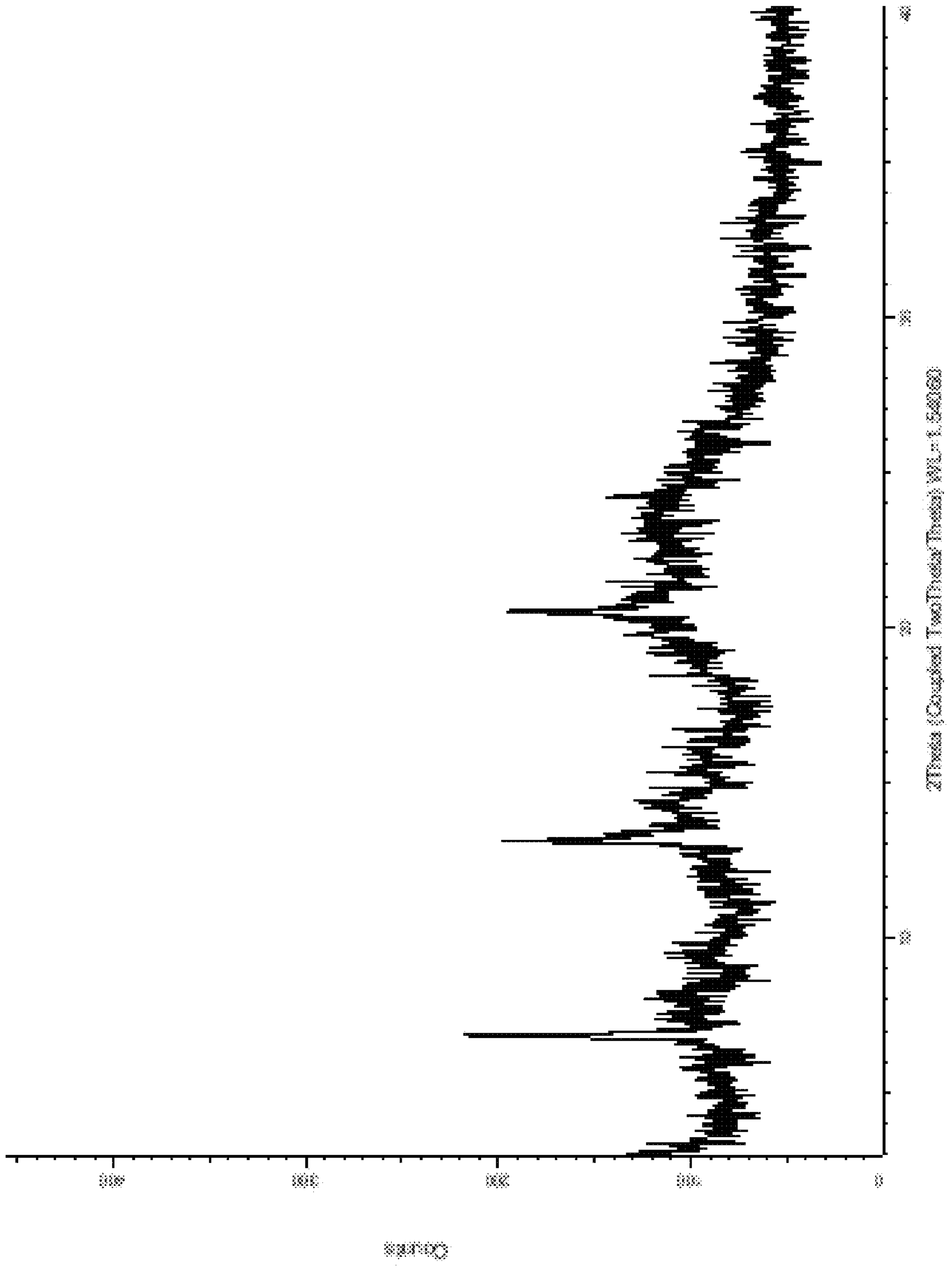
FIG. 25 is the XRPD pattern of Form F of Compound I.

The characteristic peaks (2θ) in X-ray powder diffraction pattern of Form F are shown in FIG. 25. The characteristic peaks are at values of two theta (2θ) of: 6.87, 13.07, and 20.63. The characteristic peaks can alternatively be represented as (2θ) 6.9, 13.1, and 20.6.

In one embodiment, the present invention provides a method for preparing Form F of Compound I. The method comprises the steps of:

i. preparing a suspension of Form D of Compound I in a solvent mixture comprising polyethylene glycol (polyethylene glycol volume/Compound I weight in about 1/1 ratio) and water (water volume/Compound I weight in about 1/1 ratio);
ii. heating and cooling of the suspension repeatedly between preferably about 5° C. and 50° C. for preferably about 5 times to 15 times, and more preferably about 10 times; and
iii. filtering the suspension to provide Form F of Compound I.

Figure 27:
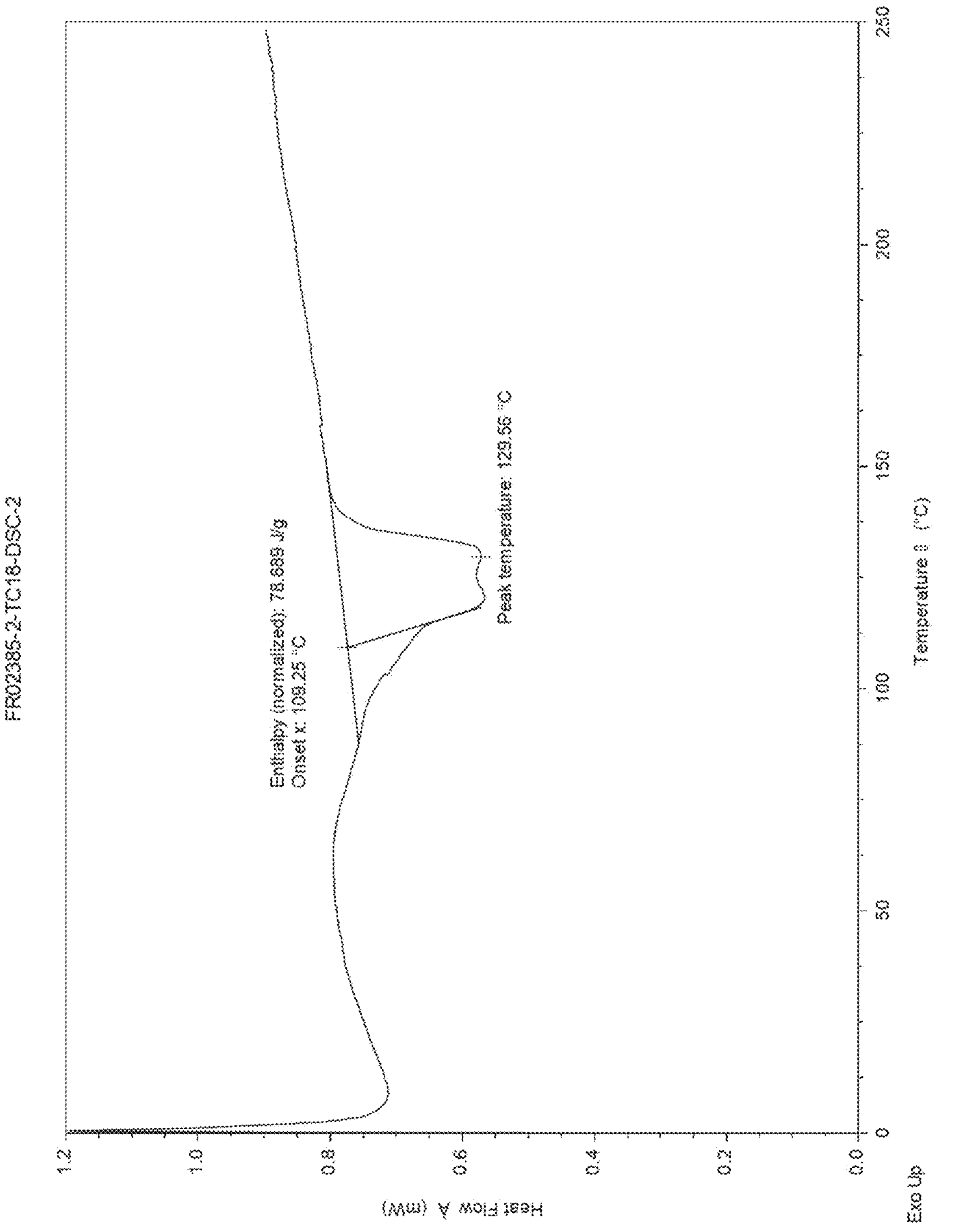
FIG. 27 is the DSC thermogram of Form G of Compound I.

The DSC thermogram of Form G of Compound I is shown in FIG. 27. The DSC thermogram has a characteristic endotherm at 130° C. with an onset temperature at 109° C.

Figure 26:
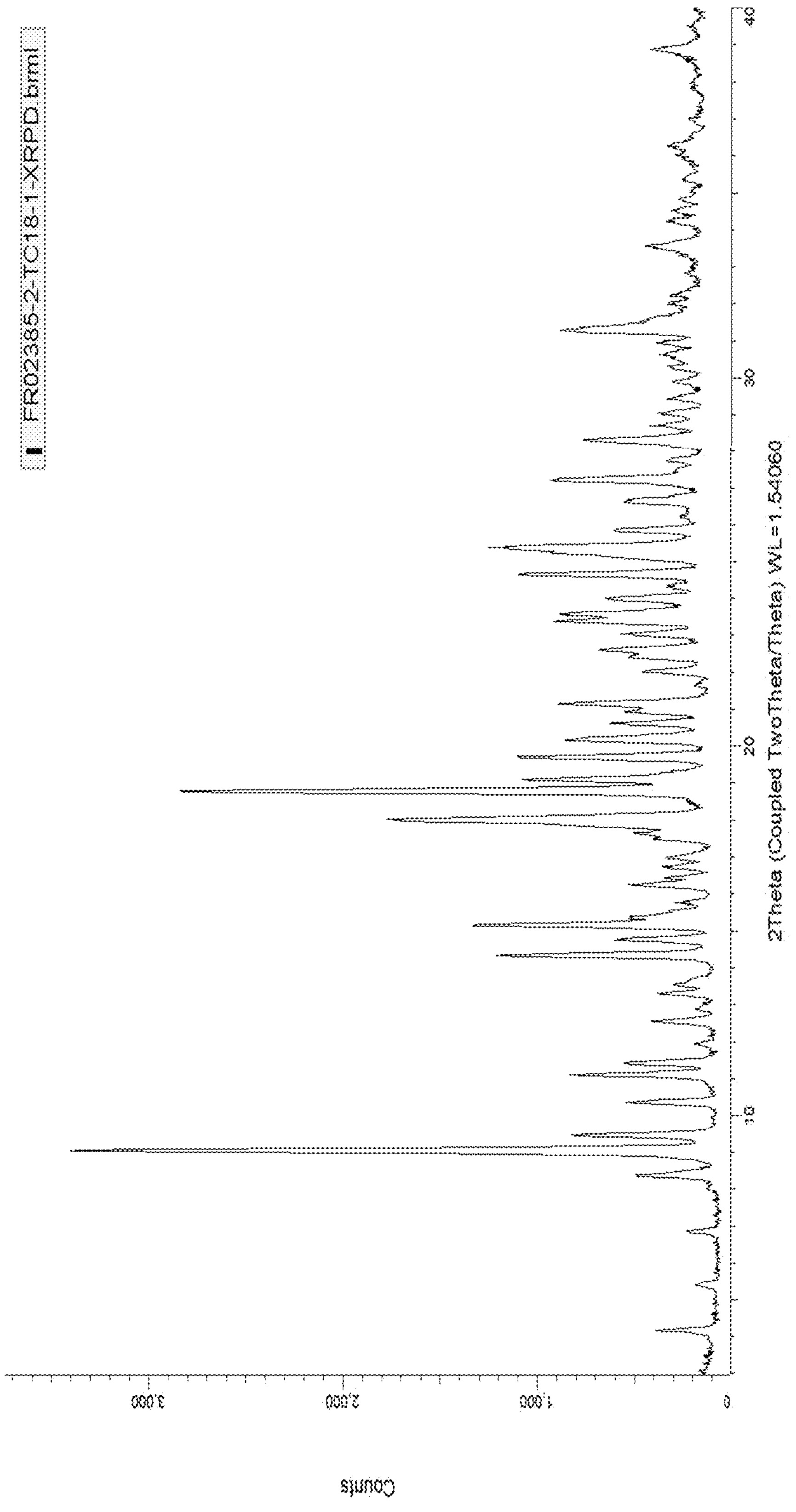
FIG. 26 is the XRPD pattern of Form G of Compound I.

The characteristic peaks (2θ) in the X-ray powder diffraction pattern of Form G are shown in FIG. 26. The characteristic peaks are at values of two theta (2θ) of: 4.18, 6.86, 8.35, 9.03, 9.44, 10.34, 11.08, 11.39, 12.53, 12.86, 13.28, 13.52, 14.31, 14.75, 15.14, 15.73, 16.22, 16.72, 16.96, 17.48, 17.62, 17.97, 18.75, 19.08, 19.68, 20.16, 20.60, 20.90, 21.13, 22.02, 22.39, 23.01, 23.38, 23.57, 23.98, 24.31, 24.64, 25.07, 25.38, 25.84, 26.63, 27.21, 28.29, 28.72, 29.01, 29.91, and 31.30. The characteristic peaks can alternatively be represented as (2θ) 4.2, 6.9, 8.4, 9.0, 9.4, 10.3, 11.1, 11.4, 12.5, 12.9, 13.3, 13.6, 14.3, 14.8, 15.1, 15.7, 16.2, 16.7, 17.0, 17.5, 17.6, 18.0, 18.8, 19.1, 19.7, 20.2, 20.6, 20.9, 21.1, 22.0, 22.4, 23.0, 23.4, 23.6, 24.0, 24.3, 24.6, 25.1, 25.4, 25.8, 26.6, 27.2, 28.3, 28.7, 29.0, 29.9, and 31.3.

In one embodiment, the present invention provides a method for preparing Form G of Compound I. The method comprises the steps of:

i. preparing a suspension of form D of Compound I in a solvent mixture comprising methyl ethyl ketone (methyl ethyl ketone volume/Compound I weight in about 1/1 ratio) and heptane (heptane volume/Compound I weight in about 1/1 ratio);
ii. Preferably adding about 0.0001X (X=weight of Compound I in step 1) to about 0.1X of Form G of Compound I, more preferably 0.001X by weight as seed;
iii. heating and cooling the suspension repeatedly at a temperature preferably between about 5° C. and 50° C.; the heating and cooling cycle is preferably conducted about 5 times to 15 times, and more preferably about 10 times; and
iv. filtering the suspension to provide form G of Compound I.

Figure 29:
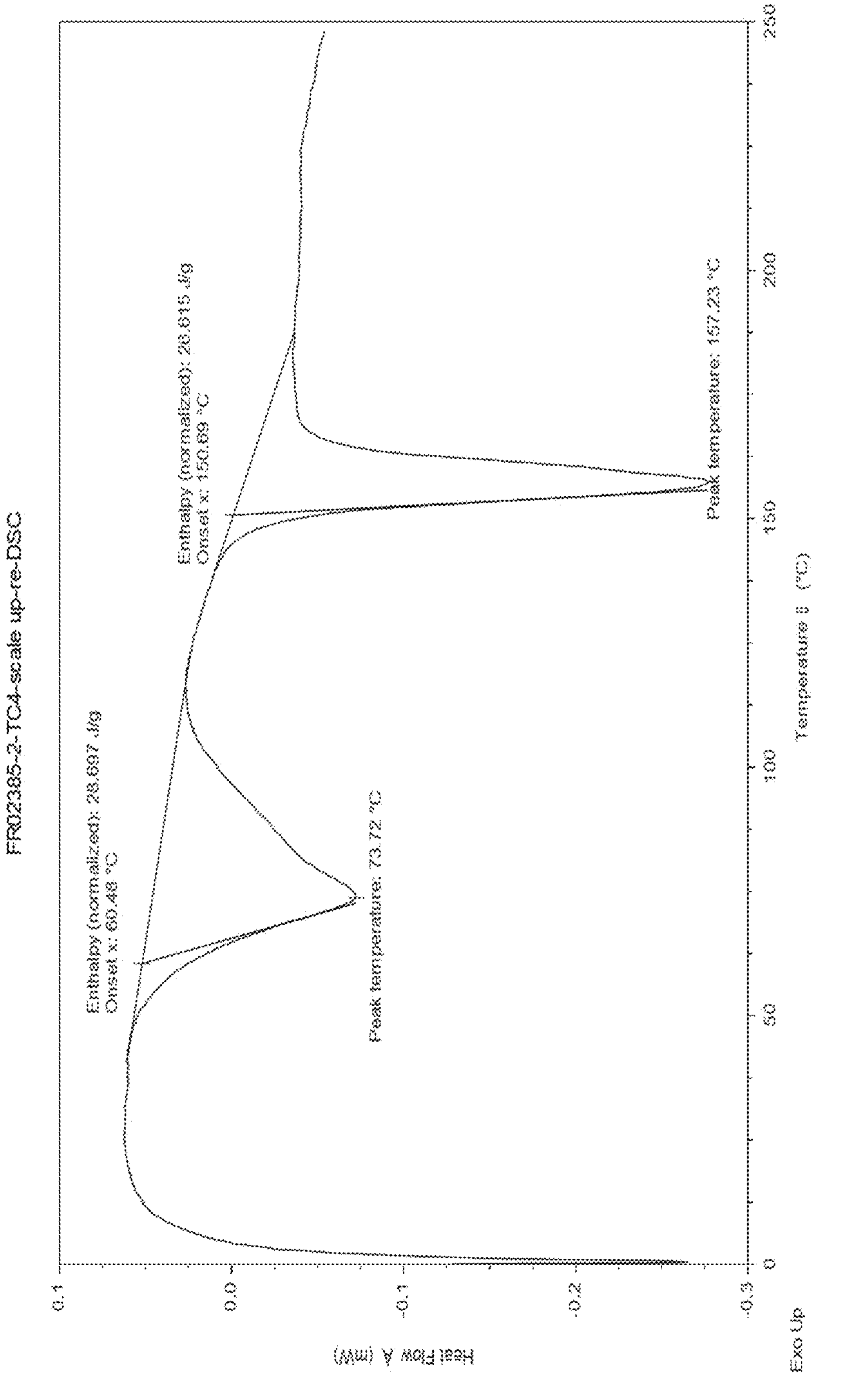
FIG. 29 is the DSC thermogram of Form H of Compound I.

The DSC thermogram of Form H of Compound I is shown in FIG. 29. The DSC thermogram of Form H has a characteristic endotherm at 74° C. with an onset temperature at 60° C. followed by an endotherm at 157° C. with an onset temperature at 151° C.

Figure 28:
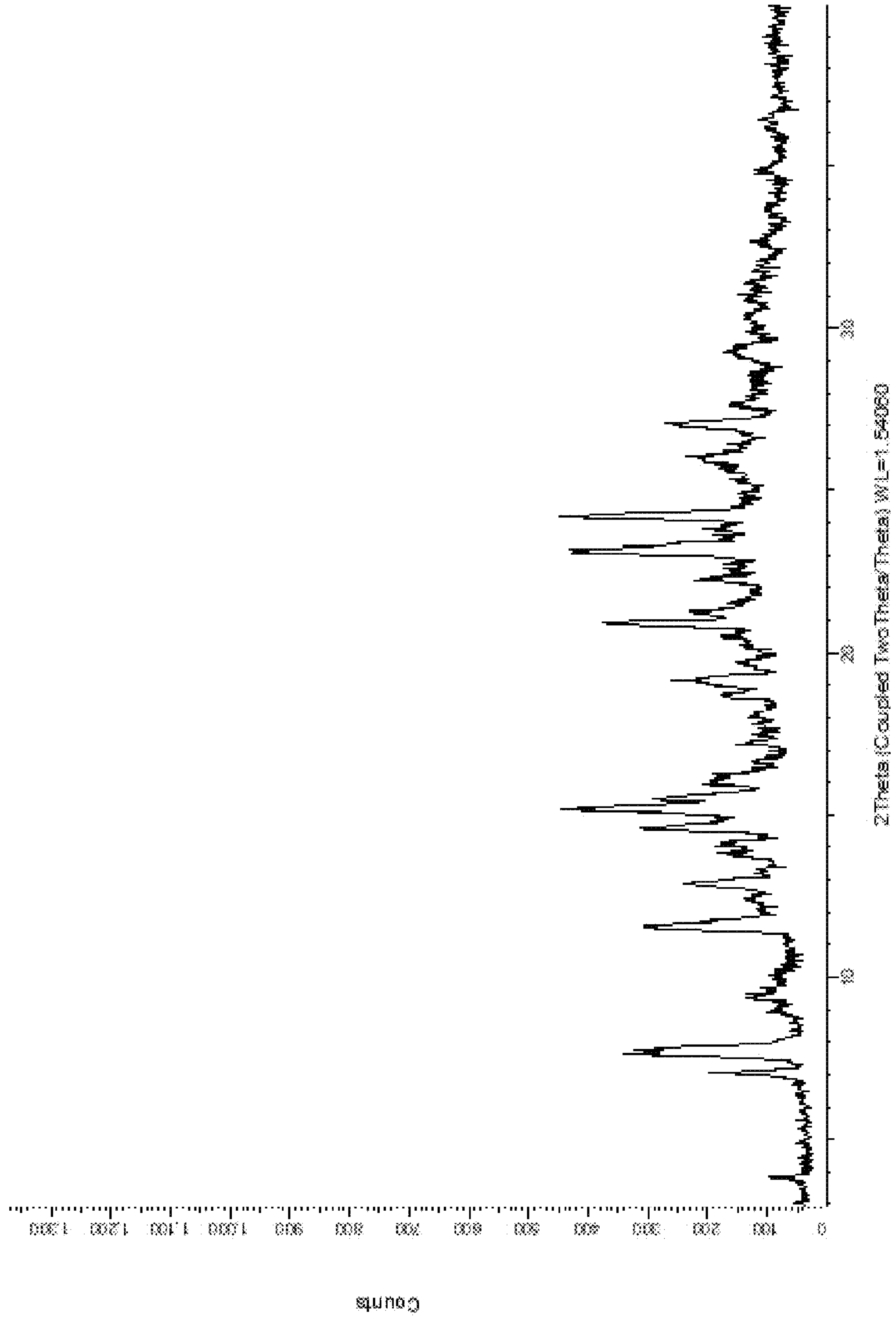
FIG. 28 is the XRPD pattern of Form H of Compound I

The characteristic peaks (2θ) in X-ray powder diffraction pattern of Form H are shown in FIG. 28. The characteristic peaks are at values of two theta (2θ) of: 3.83, 7.04, 7.61, 7.79, 8.94, 9.37, 11.46, 11.68, 12.32, 12.81, 13.21, 13.74, 14.06, 14.56, 14.80, 15.14, 15.47, 15.93, 16.15, 16.63, 17.17, 17.44, 18.01, 18.64, 19.03, 19.13, 19.59, 20.46, 20.82, 21.21, 22.20, 23.02, 23.22, 3.56, 23.80, 24.14, 25.85, 26.76, 26.96, and 27.56. The characteristic peaks can alternatively be represented as (2θ) 3.8, 7.0, 7.6, 7.8, 8.9, 9.4, 11.5, 11.7, 12.3, 12.8, 13.2, 13.7, 14.1, 14.6, 14.8, 15.1, 15.5, 15.9, 16.2, 16.6, 17.2, 17.4, 18.0, 18.6, 19.0, 19.1, 19.6, 20.5, 20.8, 21.2, 22.2, 23.0, 23.2, 23.6, 23.8, 24.1, 25.9, 26.8, 27.0, and 27.6.

In one embodiment, the present invention provides a method of preparing Form H of Compound I. The method comprises the steps of:

i. preparing a suspension of Form D of Compound I in a solvent mixture comprising isopropyl alcohol (isopropyl alcohol volume/Compound I weight in about 1/1 ratio) and water (water volume/Compound I weight in about 1/1 ratio);
ii. Preferably adding about 0.0001X (X=weight of Compound I in step 1) to about 0.1X of Form H of Compound I, more preferably 0.001X by weight as seed;
iii. stirring the suspension between preferably about 10° C. and 40° C., preferably about 20° C. and 30° C. more preferably about 25° C., for preferably about 5 days to about 15 days, and more preferably about 10 days; and
iv. filtering the suspension to provide Form H of Compound I.

Figure 30:
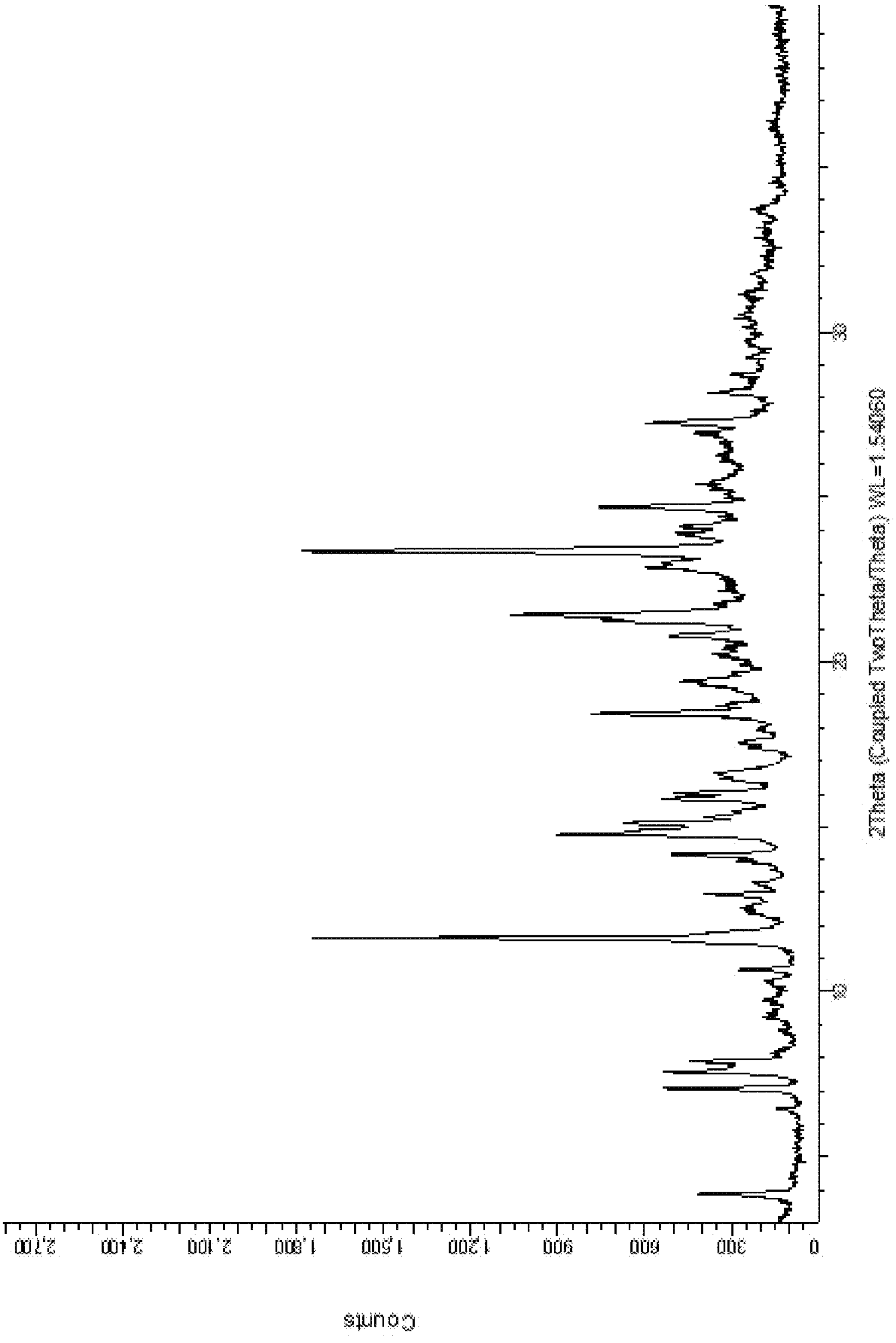
FIG. 30 is the XRPD pattern of Form H1 of Compound I.

In one embodiment, the characteristic peaks (2θ) in X-ray powder diffraction pattern of Form H1 are shown in FIG. 30. The characteristic peaks are at values of two theta (2θ) of: 3.91, 6.45, 7.08, 7.58, 7.90, 8.14, 9.28, 9.76, 10.32, 10.68, 11.63, 12.51, 12.95, 13.27, 14.15, 14.78, 15.12, 15.86, 16.57, 17.56, 17.98, 18.43, 18.67, 19.41, 20.25, 20.79, 21.25, 21.42, 21.74, 22.93, 23.36, 23.86, 24.09, 24.69, 25.40, 26.24, 26.94, 27.24, 28.16, 28.67, 29.67, 30.48, 31.12, 31.75, and 33.71. The characteristic peaks can alternatively be represented as (2θ) 3.9, 6.5, 7.1, 7.6, 7.9, 8.1, 9.3, 9.8, 10.3, 10.7, 11.6, 12.5, 13.0, 13.3, 14.2, 14.8, 15.1, 15.9, 16.6, 17.6, 18.0, 18.4, 18.7, 19.4, 20.3, 20.8, 21.3, 21.4, 21.7, 22.9, 23.4, 23.9, 24.1, 24.7, 25.4, 26.2, 26.9, 27.2, 28.2, 28.7, 29.7, 30.5, 31.1, 31.8, and 33.7.

Figure 31:
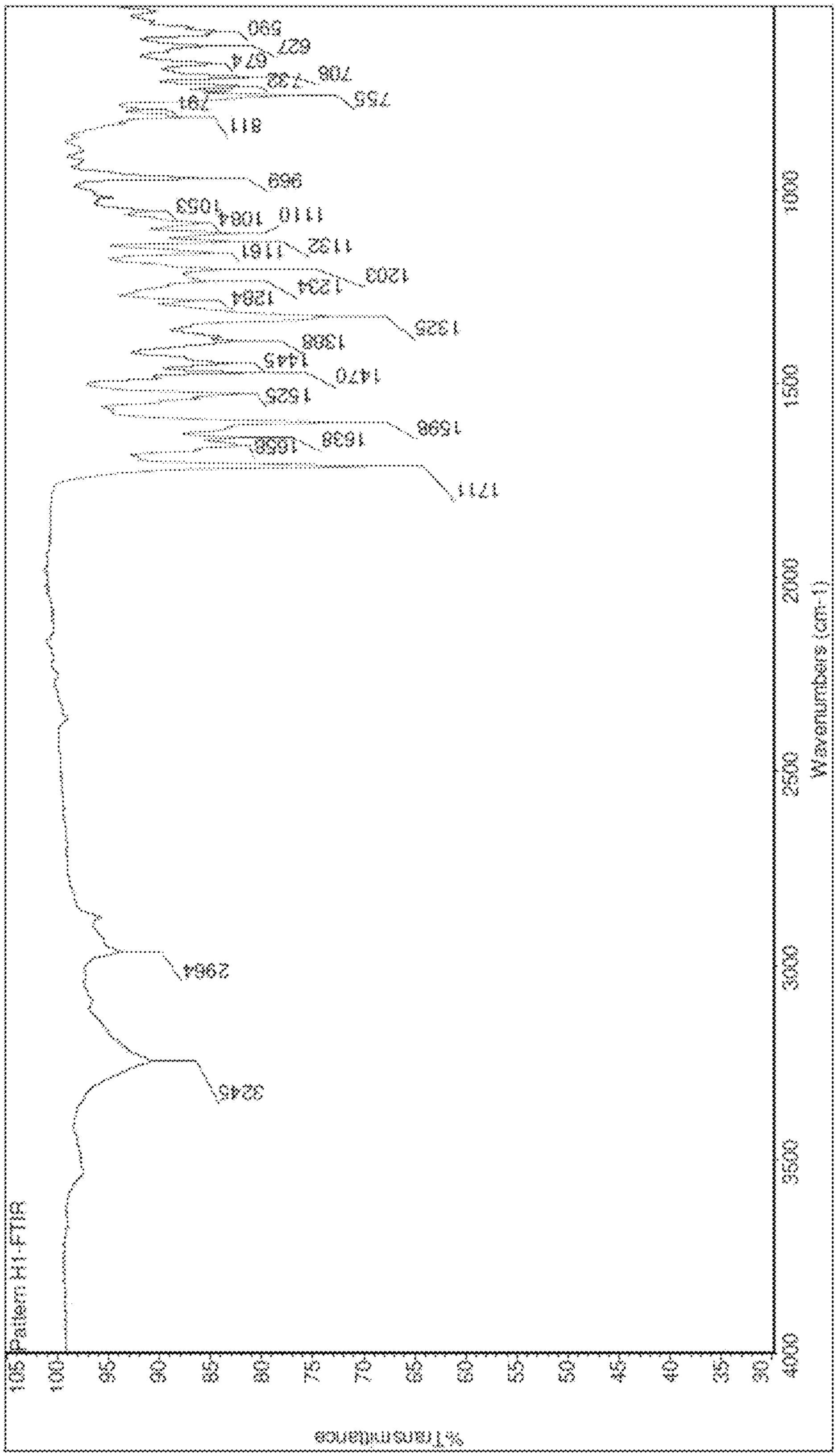
FIG. 31 is the FT-IR spectrum of Form H1 of Compound I.

In one embodiment, the Fourier-Transform Infrared (FT-IR) spectrum of the crystalline Form H1 is shown in FIG. 31. The FT-IR spectrum has characteristic peaks at ($cm^{-1}$) 537, 590, 627, 674, 708, 732, 744, 755, 791, 811, 969, 1053, 1084, 1110, 1132, 1161, 1203, 1234, 1284 1325, 1388, 1445, 1470, 1525, 1598, 1638, 1658, 1711, and 3245.

The present invention provides a method for preparing Form H1 of Compound I. The method comprises storing Form H of Compound I between about −15° C. and 20° C., preferably about 0° C. and 10° C., more preferably about 25° C., for preferably about 1 month to 12 months, and more preferably about 6 months to provide Form H1 of Compound I.

Figure 33:
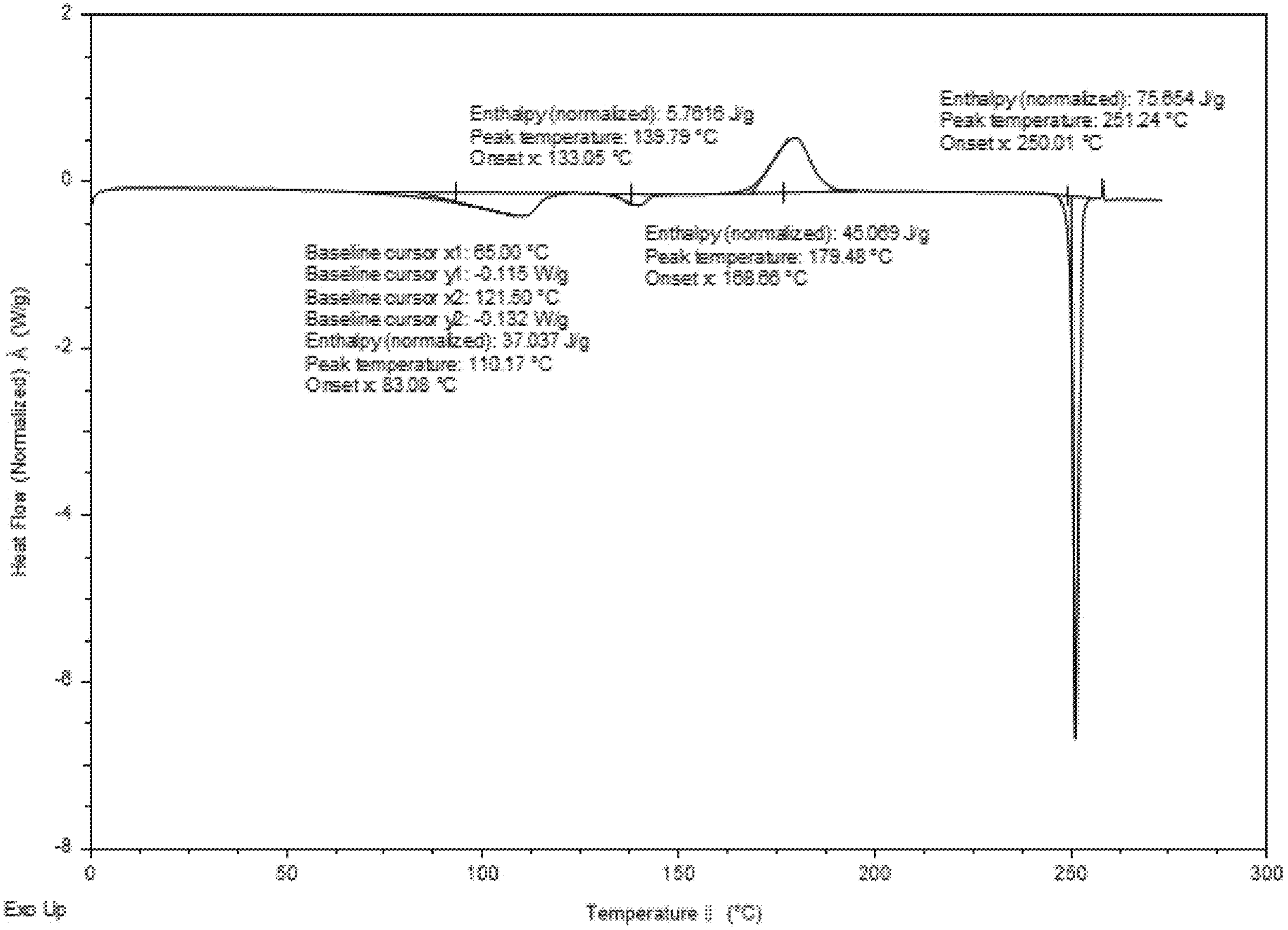
FIG. 33 is the DSC thermogram of Form J of Compound I.

The DSC thermogram of Form J of Compound I is shown in FIG. 33. The DSC thermogram has a characteristic endotherm at 110° C. with an onset temperature at 83° C. and an endotherm at 140° C. with an onset temperature at 133° C. The DSC thermogram also has a characteristic exotherm at 179° C. with an onset temperature at 133° C. followed by an endotherm at 251° C. with an onset temperature at 250° C.

Figure 32:
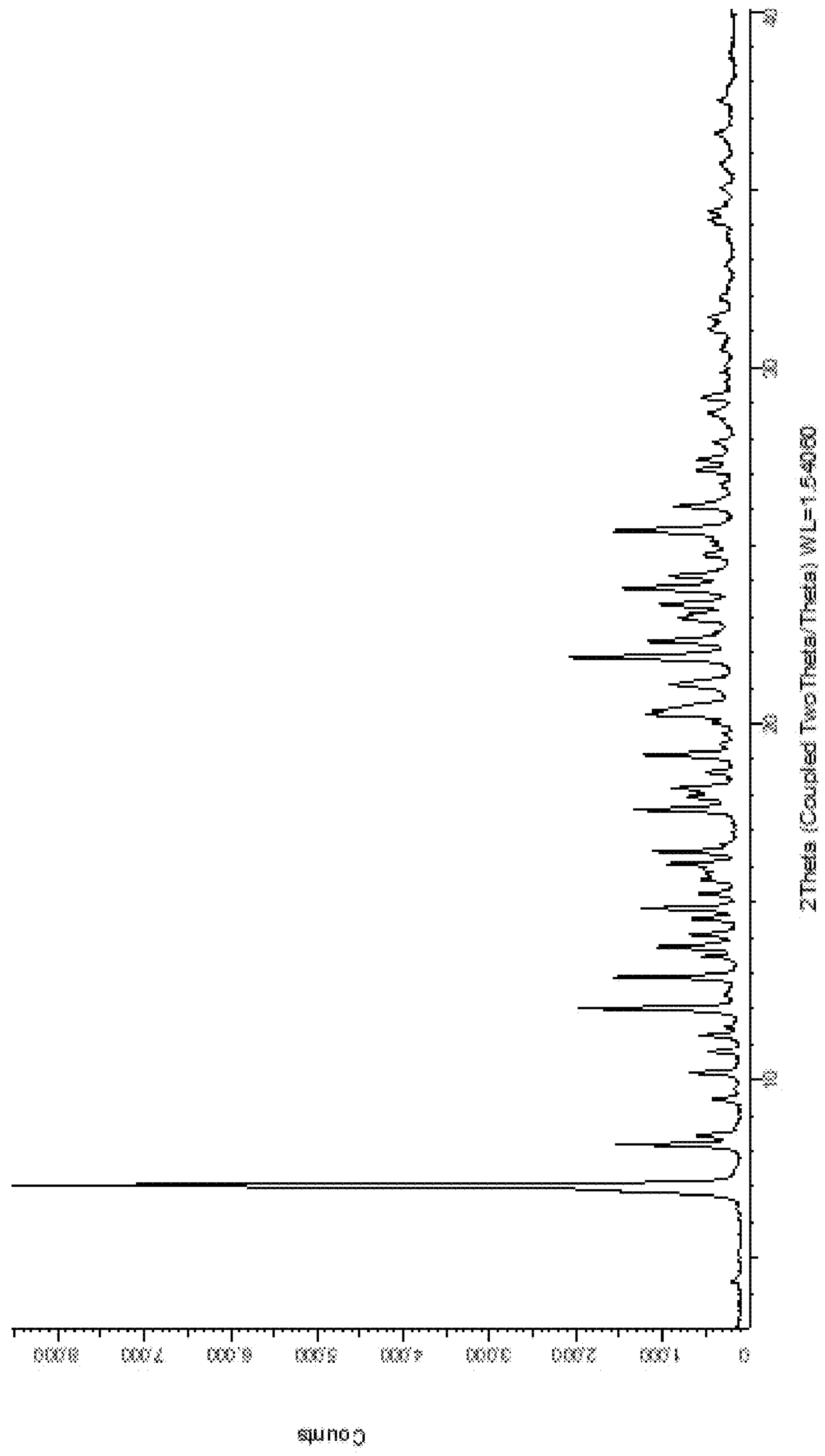
FIG. 32 is the XRPD pattern of Form J of Compound I.

The characteristic peaks (2θ) in X-ray powder diffraction pattern of Form J are shown in FIG. 32. The characteristic peaks are at values of two theta (2θ) of: 4.36, 6.92, 7.05, 7.44, 8.21, 8.45, 9.47, 9.76, 10.22, 10.80, 11.26, 11.49, 12.02, 12.41, 12.90, 13.48, 13.74, 14.09, 14.53, 14.82, 15.24, 15.63, 15.78, 16.07, 16.41, 16.61, 17.60, 17.95, 18.20, 18.64, 19.13, 19.43, 19.72, 20.03, 20.26, 20.36, 20.51, 21.11, 21.87, 22.32, 22.97, 23.07, 23.35, 23.80, 24.14, 24.75, 24.99, 25.16, 25.42, 26.11, 26.69, 27.12, 27.42, 27.89, 28.51, 28.74, 29.16, 29.89, 30.06, 30.51, 31.07, 31.42, 31.98, 32.33, 32.88, 33.67, 34.13, 34.38, 35.03, 35.73, 36.53, 37.47, and 38.84. The characteristic peaks can alternatively be represented as (2θ) 4.4, 6.9, 7.1, 7.4, 8.2, 8.5, 9.5, 9.8, 10.2, 10.8, 11.3, 11.5, 12.0, 12.4, 12.9, 13.5, 13.7, 14.1, 14.5, 14.8, 15.2, 15.6, 15.8, 16.1, 16.4, 16.6, 17.6, 18.0, 18.2, 18.6, 19.1, 19.4, 19.7, 20.0, 20.3, 20.4, 20.5, 21.1, 21.9, 22.3, 23.0, 23.1, 23.4, 23.8, 24.1, 24.8, 25.0, 25.2, 25.4, 26.1, 26.7, 27.1, 27.4, 27.9, 28.5, 28.7, 29.2, 29.9, 30.1, 30.5, 31.1, 31.4, 32.0, 32.3, 32.9, 33.7, 34.1, 34.4, 35.0, 35.7, 36.5, 37.5, and 38.8.

Figure 34:
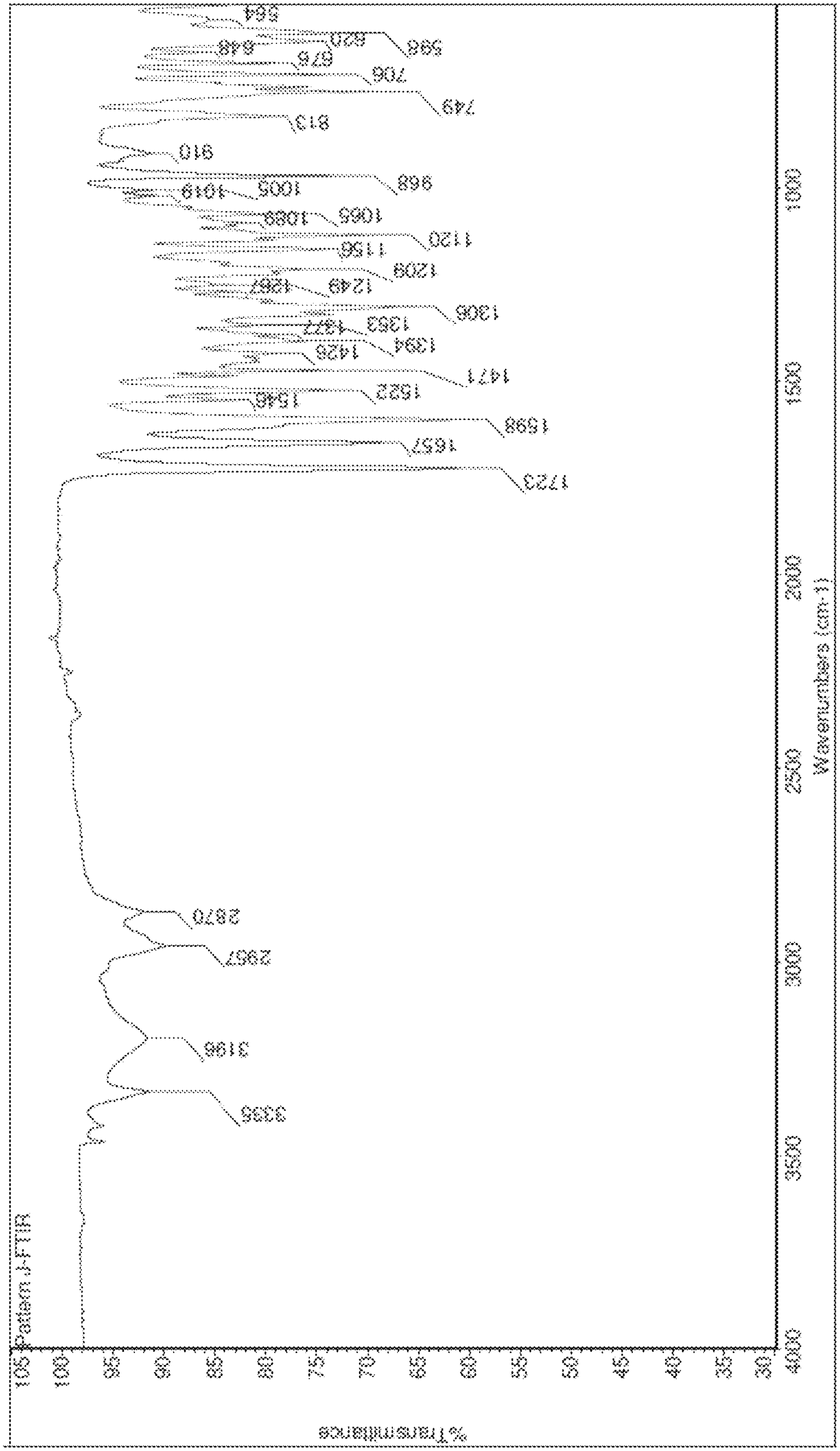
FIG. 34 is the FT-IR spectrum of form J of Compound I.

The Fourier-Transform Infrared (FT-IR) spectrum of Form J is shown in FIG. 34. The FT-IR spectrum has characteristic peaks in wave numbers ($cm^{-1}$) at 564, 598, 620, 648, 676, 706, 737, 749, 813, 910, 968, 1005, 1019, 1065, 1089, 1120, 1133, 1156, 1209, 1249, 1267, 1306, 1326, 1353, 1377, 1394, 1426, 1439, 1471, 1484, 1522, 1546, 1598, 1657, 1723, 2870, 2957, 3196, 3335.

In one embodiment, the present invention provides a method for preparing Form J of Compound I. The method comprises the steps of:

i. preparing a solution of Compound I in about 2.3X (X=weight of Compound I) tetrahydrofuran by volume between preferably about 10° C. and 40° C., more preferably about 22° C. and 25° C.;
ii. Preferably adding about 0.001X to about 0.1X Form J of Compound I as seed and adding about 3X by volume of heptane to provide a suspension of Form J of Compound I; and
iii. filtering the suspension to provide Form J of Compound I.

In another aspect, the present invention features a crystalline (polymorph or pseudopolymorph) form of Compound I which has characteristic peaks in the X-ray powder diffraction (XRPD) pattern as shown in FIG. 3, FIG. 7, FIG. 9, FIG. 12, FIG. 13, FIG. 15, FIG. 17, FIG. 19, FIG. 20, FIG. 23, FIG. 25, FIG. 26, FIG. 28, FIG. 30, FIG. 32 and which is substantially pure. As used herein, the term "substantially pure", when used in reference to a given crystalline form, refers to the crystalline form which is at least about 90% pure. This means that the crystalline form does not contain more than about 10% of any other form of Compound I. Preferably, the term "substantially pure" refers to a crystalline form of Compound I which is at least about 95% pure. This means that the crystalline form of Compound I does not contain more than about 5% of any other form of Compound I. More preferably, the term "substantially pure" refers to a crystalline form of Compound I which is at least about 97% pure. This means that the crystalline form of Compound I does not contain more than about 3% of any other form of Compound I.

The $^{1}$HNMR spectrum of each polymorph and pseudopolymorph disclosed herein is predominantly consistent with Compound I.

The instruments and related methods used to characterize the polymorphs and pseudopolymorphs of Compound I are listed in Table 11. The results of these studies are presented in FIGS. 1-34. As is known in the art, the relative intensity of each peak in FIG. 1-FIG. 34 may change or shift under certain conditions, although the polymorph and pseudopolymorph forms are the same. One of ordinary skill in the art is able to readily determine whether a given polymorphic or pseudopolymorphic form is the same polymorph or pseudopolymorph form as described herein by comparing its XRPD pattern with FIG. 3, FIG. 7, FIG. 9, FIG. 12, FIG. 13, FIG. 15, FIG. 17, FIG. 19, FIG. 20, FIG. 23, FIG. 25, FIG. 26, FIG. 28, FIG. 30, and FIG. 32; comparing its DSC thermogram with FIG. 4, FIG. 8, FIG. 10, FIG. 14, FIG. 16, FIG. 18, FIG. 21, FIG. 24, FIG. 27, FIG. 29 and, FIG. 33 for DSC; and comparing its FTIR spectrum with FIG. 5, FIG. 11, FIG. 22, FIG. 31, and FIG. 34.

TABLE 11

Instrumental methods for XRPD, DSC, NMR, FT-IR and single crystal X-Ray diffraction

| X-ray Powder Diffractometer (XRPD) | |
|---|---|
| Instrument | Bruker D8 Advance |
| X-ray geometry | Reflection |
| Detector | LYNXEYE_XE_T (1D mode) |
| Open angle | 2.9° (max) |
| Radiation | Cu/K-Alpha1 (λ = 1.5406 Å) |
| X-ray generator power | 40 kV, 40 mA |
| Primary beam path slits | Twin Primary motorized slit: 20.0 mm by sample length; Primary Soller slit: 2.5° |
| Secondary beam path slits | Secondary Soller slit: 2.5° |
| Scan mode | Continuous scan |
| Scan type | Locked coupled |
| Step size | 0.02° |
| Time per step | 0.3 or 0.12 second per step |
| Scan range | 2° or 3° to 40° |
| Sample rotation speed | 15 rpm |
| Sample holder | Flat monocrystalline silicon |
| **Differential Scanning Calorimeter (DSC)** | |
| Instrument | TA Instruments Discovery 2500 |
| Sample pan | Tzero pan and Tzero hermetic lid with a manually punched pin hole of about 0.7 mm in diameter |
| Temperature range | ~30° C. to 250° C. or before decomposition |
| Heating rate | 10° C./min |
| Nitrogen flow | 50 mL/min |
| Sample mass | ~0.5-5 mg |

TABLE 11-continued

| Instrumental methods for XRPD, DSC, NMR, FT-IR and single crystal X-Ray diffraction | |
|---|---|
| Nuclear Magnetic Resonance (NMR) | |
| Instrument | Bruker Advance-AV 400M (for $^1$H-NMR) |
| Frequency | 400 MHz |
| Probe | 5 mm PABBO BB/19F-1H/D Z-GRD Z108618/0406 (for $^1$H- NMR) |
| Number of scans | 8 |
| Temperature | 297.6 K |
| Relaxation delay | 1 second |
| Instrument | Bruker D8 Venture |
| Single Crystal X-ray Diffractometer (SCXRD) method | |
| Detector | CMOS area detector |
| Temperature | 170(2) K |
| Radiation | Cu/K-Alpha1 (λ = 1.5418 Å) |
| X-ray generator power | 50 kV, 1.2 mA |
| Distance from sample to area detector | 40 mm |
| Exposure time | 3 second |
| Resolution | 0.80 Å |
| Fourier Transform Infrared Spectrometer (FT-IR) | |
| Instrument | Thermo Nicolet iS5 |
| Number of scans | 32 |
| Mode | ATR |
| Resolution | 4 |
| Sample compartment | Main |
| Detector | DTGS KBr |
| Beamsplitter | KBr |
| Source | IR |
| Accessory | ID7 |
| Window | Diamond |
| Recommended range | 4,000-525 $cm^{-1}$ |
| Gain: 1 | 1.0 |
| Optical velocity | 0.4747 |
| Aperture | 100 |

In one embodiment, a process or composition of the invention described herein (including any process or composition described in any aspect, embodiment, example or preference) uses or comprises a crystalline Form 1 of Compound I which is substantially pure. For example, the crystalline Form 1 can be at least 90% pure, preferably at least 95% pure, or more preferably at least 97% pure.

In one embodiment, a process or composition of the invention described herein (including any process or composition described in any aspect, embodiment, example or preference) uses or comprises a Form 2 of Compound I which is substantially pure. For example, the Form 2 can be at least 90% pure, preferably at least 95% pure, or more preferably at least 97% pure.

In one embodiment, a process or composition of the invention described herein (including any process or composition described in any aspect, embodiment, example or preference) uses or comprises a Form 3 of Compound I which is substantially pure. For example, the Form 3 can be at least 90% pure, preferably at least 95% pure, or more preferably at least 97% pure.

In one embodiment, a process or composition of the invention described above (including any process or composition described in any aspect, embodiment, example or preference) uses a Form 4 of Compound I which is substantially pure. For example, the Form 4 can be at least 90% pure, preferably at least 95% pure, or more preferably at least 97% pure.

In one embodiment, a process of the invention described above (including any process described in any aspect, embodiment, example or preference) uses a Form A of Compound I which is substantially pure. For example, the Form A can be at least 90% pure, preferably at least 95% pure, or more preferably at least 97% pure.

In one embodiment, a process of the invention described above (including any process described in any aspect, embodiment, example or preference) uses a Form B of Compound I which is substantially pure. For example, the Form B can be at least 90% pure, preferably at least 95% pure, or more preferably at least 97% pure.

In one embodiment, a process of the invention described above (including any process described in any aspect, embodiment, example or preference) uses a Form C of Compound I which is substantially pure. For example, the Form C can be at least 90% pure, preferably at least 95% pure, or more preferably at least 97% pure.

In one embodiment, a process of the invention described above (including any process described in any aspect, embodiment, example or preference) uses a Form D of Compound I which is substantially pure. For example, the Form D can be at least 90% pure, preferably at least 95% pure, or more preferably at least 97% pure.

In one embodiment, a process of the invention described above (including any process described in any aspect, embodiment, example or preference) uses a Form E of Compound I which is substantially pure. For example, the Form E can be at least 90% pure, preferably at least 95% pure, or more preferably at least 97% pure.

In one embodiment, a process of the invention described above (including any process described in any aspect, embodiment, example or preference) uses a Form F of Compound I which is substantially pure. For example, the Form F can be at least 90% pure, preferably at least 95% pure, or more preferably at least 97% pure.

In one embodiment, a process of the invention described above (including any process described in any aspect, embodiment, example or preference) uses a Form G of Compound I which is substantially pure. For example, the Form G can be at least 90% pure, preferably at least 95% pure, or more preferably at least 97% pure.

In one embodiment, a process of the invention described above (including any process described in any aspect, embodiment, example or preference) uses a Form H of Compound I which is substantially pure. For example, the Form H can be at least 90% pure, preferably at least 95% pure, or more preferably at least 97% pure.

In one embodiment, a process of the invention described above (including any process described in any aspect, embodiment, example or preference) uses a Form H1 of Compound I which is substantially pure. For example, the Form H1 can be at least 90% pure, preferably at least 95% pure, or more preferably at least 97% pure.

In one embodiment, a process of the invention described above (including any process described in any aspect, embodiment, example or preference) uses a Form J of Compound I which is substantially pure. For example, the Form J can be at least 90% pure, preferably at least 95% pure, or more preferably at least 97% pure.

Unless otherwise defined, all technical and scientific terms used herein are accorded the meaning commonly known to one of ordinary skill in the art. All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

Pharmaceutical Compositions

The pharmaceutical compositions of the present invention comprise a therapeutically effective amount of a polymorph or pseudopolymorph of Compound I the invention or a combination of two or more such polymorphs or pseudopolymorphs of Compound I formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intra-arterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectable.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches.

The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to Van Devanter et al., U.S. Pat. No. 5,508,269 to Smith et al., and WO 98/43650 by Montgomery, all of which are incorporated herein by reference).

Antiviral Activity

The present invention provides a treatment of prevention of a viral infection in a subject in need thereof, comprising administering to the subject a therapeutically effective amount of a polymorph or pseudopolymorph of Compound I as described herein or a combination of two or more thereof. The viral infection is preferably a coronavirus infection. In certain embodiments, the coronavirus is SARS-CoV-1, SARS-CoV-2, or MERS-CoV. Preferably the coronavirus is SARS-CoV-2.

A viral inhibitory amount or dose of the Compound I of the present invention may range from about 0.01 mg/Kg to about 500 mg/Kg, alternatively from about 1 to about 50 mg/Kg. Inhibitory amounts or doses will also vary depending on route of administration, as well as the possibility of co-usage with other agents.

According to the methods of treatment of the present invention, viral infections are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). A therapeutically effective amount of the compound described above may range, for example, from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily dose of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the present invention described herein can, for example, be administered by injection, intravenously, intra-arterial, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound. Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Combination and Alternation Therapy

The compounds of the present invention may be used in combination with one or more antiviral therapeutic agents or anti-inflammatory agents useful in the prevention or treatment of viral diseases or associated pathophysiology. Thus, the compounds of the present invention and their salts, solvates, or other pharmaceutically acceptable derivatives thereof, may be employed alone or in combination with other antiviral or anti-inflammatory therapeutic agents. The compounds herein and pharmaceutically acceptable salts thereof may be used in combination with one or more other agents which may be useful in the prevention or treatment of respiratory disease, inflammatory disease, autoimmune disease, for example; antihistamines, corticosteroids, (e.g., fluticasone propionate, fluticasone furoate, beclomethasone dipropionate, budesonide, ciclesonide, mometasone furoate, triamcinolone, flunisolide), NSAIDs, leukotriene modulators (e.g., montelukast, zafirlukast, pranlukast), tryptase inhibitors, IKK2 inhibitors, p38 inhibitors, Syk inhibitors, protease inhibitors such as elastase inhibitors, integrin antagonists (e.g., beta-2 integrin antagonists), adenosine A2a agonists, mediator release inhibitors such as sodium chromoglycate, 5-lipoxygenase inhibitors (zyflo), DP1 antagonists, DP2 antagonists, PI3K delta inhibitors, ITK inhibitors, LP (lysophosphatidic) inhibitors or FLAP (5-lipoxygenase activating protein) inhibitors (e.g., sodium 3-(3-(tert-butylthio)-1-(4-(6-ethoxypyridin-3-yl)benzyl)-5-((5-ethylpyridin-2-yl)methoxy)-1H-indol-2-yl)-2,2-dimethylpropanoate), bronchodilators (e.g., muscarinic antagonists, beta-2 agonists), methotrexate, and similar agents; monoclonal antibody therapy such as anti-IgE, anti-TNF, anti-IL-5, anti-IL-6, anti-IL-12, anti-IL-1 and similar agents; cytokine receptor therapies e.g. etanercept and similar agents; antigen non-specific immunotherapies (e.g. interferon or other cytokines/chemokines, chemokine receptor modulators such as CCR3, CCR4 or CXCR2 antagonists, other cytokine/chemokine agonists or antagonists, TLR agonists and similar agents), suitable anti-infective agents including antibiotic agents, antifungal agents, antheimintic agents, antimalarial agents, antiprotozoal agents, antituberculosis agents, and antiviral agents, including those listed at https://www.drugs.com/drug-class/anti-infectives.html. In general, combination therapy is typically preferred over alternation therapy because it induces multiple simultaneous stresses on the virus.

When the compositions of this invention comprise one or more polymorphs and/or pseudopolymorphs of Compound I as described herein and one or more additional therapeutic or prophylactic agents, both the Compound I and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention.

Alternatively, those agents may be part of a single dosage form, combined with a compound of this invention in a single composition.

The "additional therapeutic or prophylactic agents" include but are not limited to, immune therapies (e.g. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (e.g. N-acetylcysteine), cytokine agonists, cytokine antagonists, lung surfactants and/or antimicrobial and anti-viral agents (e.g. ribavirin and amantidine). The compositions according to the invention may also be used in combination with gene replacement therapy.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1: Preparation of Form 1 of Compound I

Procedure 1A: Ethyl acetate (700 mL, 10 V (volume), 1 volume means 1 g of solid in 1 mL of solvent) was added into reactor (R1) followed by adding the compound (3R,5'S)-1'-(N-methyl-N-(4,6,7-trifluoro-1H-indole-2-carbonyl)-L-leucyl)-2-oxospiro[indoline-3,3'-pyrrolidine]-5'-carboxamide (70 g). The reaction was cooled to 0° C. (−5 to +5° C.) and then triethylamine (89.6 g) was added followed by trifluoroacetic anhydride (92.4 g) at 0° C. (−5 to 5° C.). The reaction was stirred for 1 hour (0.5-2 hours) at 0° C. (−5 to 5° C.). Once the reaction was complete, the reaction mixture was added slowly to 0.2 N aqueous HCl solution (700 g) over 1 hour at 0° C. (−5~5° C.). The resulting solution was stirred for 10-30 minutes at 0° C. (−5~5° C.) and the organic layer was separated. The organic layer was separated and washed with 10% brine for five times. Then the organic layer was separated and distilled to 280 mL (note: 280 mL is the total volume of the solution). Form 1 seed was added to induce the crystallization at 50° C. Then toluene-EtOAc exchange was performed to control the level of EtOAc at 1-5% wt/wt (weight of EtOAc/weight of toluene by Gas Chromatography) by adding about 10 V of toluene followed by distillation to 8 V, and then repeating the cycle by adding 8 V of toluene followed by distillation to 8 V (note: volume of the solution). The suspension was slowly cooled down from 50° C. to 25° C. for over 1 hour and stirred for 5 hours (3~8 hours) at 25° C. (20-30° C.). The suspension was filtered, and the wet cake was rinsed with toluene (2V). The wet cake was dried at 50° C. (45-55° C.) for 48 hours to provide Form 1 of compound I as a white solid in 80-85% yield. $^{1}$H NMR (400 MHz, Acetone-$d_6$) δ 11.17 (s, 1H), 9.65 (s, 1H), 7.02 (dd, J=13.7, 7.3 Hz, 2H), 6.94 (dd, J=6.0, 3.5

Hz, 1H), 6.92-6.85 (m, 2H), 6.81 (t, J=7.5 Hz, 1H), 5.56 (dd, J=9.4, 5.6 Hz, 1H), 5.21 (t, J=8.3 Hz, 1H), 4.25 (d, J=10.7 Hz, 1H), 3.99 (d, J=10.6 Hz, 1H), 3.43 (s, 3H), 2.79-2.61 (m, 2H), 1.93 (ddd, J=14.4, 9.5, 5.1 Hz, 1H), 1.79 (ddd, J=14.2, 8.7, 5.6 Hz, 1H), 1.64 (dpd, J=8.7, 6.6, 5.1 Hz, 1H), 0.98 (dd, J=18.5, 6.6 Hz, 6H).

Procedure 1B: Ethyl acetate (300 mL, 10 volume, 1 volume means 1 g of solid in 1 mL of solvent) was added into reactor (R1) followed by adding the compound (3R, 5'S)-1'-(N-methyl-N-(4,6,7-trifluoro-1H-indole-2-carbonyl)-L-leucyl)-2-oxospiro[indoline-3,3'-pyrrolidine]-5-carboxamide (30 g) to form a clear solution. The reaction was cooled to 0° C. (−5 to 5° C.) and then triethylamine (38.3 g) was added followed by trifluoroacetic anhydride (39.7 g) at 0° C. (−5 to 5° C.). The reaction was stirred for 20 min at 0° C. (−5 to 5° C.) before taking sample for purity analysis. Once the reaction was complete, the reaction mixture was added slowly to 0.2 N aqueous HCl solution (300 g) in reactor R2 over 1 hour at 0° C. (−5 to 5° C.). The resulting solution was stirred for 20 minutes at 0° C. (−5 to 5° C.) and the organic layer was separated and washed with 10% brine (300 mL) for five times. Then the organic layer was separated and distilled to 60 mL (note: 60 mL is the volume of the solution) below 50° C. under vacuum. Toluene (300 mL) was then added, and the mixture was concentrated into 120 mL. Additional Toluene (300 mL) was added, and the resulting mixture was concentrated to a final volume of 240 mL. The temperature of mixture was adjusted to 75° C. (70-80° C.) and stirred for 1 hour at 75° C. (70-80° C.). Then the mixture was slowly cooled to 20° C. (15-25° C.) over 1 h and the resulting suspension was stirred for 1 hours (0.5-2 hours) at 20° C. (15-25° C.). The suspension was filtered, and the wet cake was rinsed with toluene (60 mL). The wet cake was dried at 50° C. (45-55° C.) for 16 hours to provide Form 1 of Compound I as a white solid in 80-85% yield. 1H NMR (400 MHz, Acetone-d6) δ 11.17 (s, 1H), 9.65 (s, 1H), 7.02 (dd, J=13.7, 7.3 Hz, 2H), 6.94 (dd, J=6.0, 3.5 Hz, 1H), 6.92-6.85 (m, 2H), 6.81 (t, J=7.5 Hz, 1H), 5.56 (dd, J=9.4, 5.6 Hz, 1H), 5.21 (t, J=8.3 Hz, 1H), 4.25 (d, J=10.7 Hz, 1H), 3.99 (d, J=10.6 Hz, 1H), 3.43 (s, 3H), 2.79-2.61 (m, 2H), 1.93 (ddd, J=14.4, 9.5, 5.1 Hz, 1H), 1.79 (ddd, J=14.2, 8.7, 5.6 Hz, 1H), 1.64 (dpd, J=8.7, 6.6, 5.1 Hz, 1H), 0.98 (dd, J=18.5, 6.6 Hz, 6H).

Procedure 2: The following procedure is used to further purify Form 1 of Compound I, such as Form 1 prepared as described in Procedure 1(a) or 1(b) above. 20 g of Compound I and ethanol (300 mL, 15 V) were added to the reactor at 20-30° C. The mixture was stirred at 70-80° C. to completely dissolve Form 1 of Compound I. The solution was slowly cooled to 60° C. over 1 hour. Form 1 of Compound I seed was added to induce the crystallization and the resulting suspension was stirred at 60° C. for 0.5-1.5 hours. The suspension was then slowly cooled to 20-30° C. over 1 hour. Water (300 mL, 15 V) was slowly added into the suspension over 5 hours. The obtained suspension was stirred at 20-30° C. for 0.5-2 hours. The slurry was filtered and the wet cake was rinsed with $EtOH/H_2O$ (30 mL/30 mL). The wet cake was dried at 50° C. (45-55° C.) for 48 hours to afford Form 1 of Compound I as a solid in 95-100% yield. 1H NMR (400 MHz, Acetone-$d_6$) δ 11.17 (s, 1H), 9.65 (s, 1H), 7.02 (dd, J=13.7, 7.3 Hz, 2H), 6.94 (dd, J=6.0, 3.5 Hz, 1H), 6.92-6.85 (m, 2H), 6.81 (t, J=7.5 Hz, 1H), 5.56 (dd, J=9.4, 5.6 Hz, 1H), 5.21 (t, J=8.3 Hz, 1H), 4.25 (d, J=10.7 Hz, 1H), 3.99 (d, J=10.6 Hz, 1H), 3.43 (s, 3H), 2.79-2.61 (m, 2H), 1.93 (ddd, J=14.4, 9.5, 5.1 Hz, 1H), 1.79 (ddd, J=14.2, 8.7, 5.6 Hz, 1H), 1.64 (dpd, J=8.7, 6.6, 5.1 Hz, 1H), 0.98 (dd, J=18.5, 6.6 Hz, 6H).

Example 2: Preparation of Form 2 of Compound I

About 15 mg of Form J of Compound I was heated to 155° C. at a rate of 10° C./min and hold at 155° C. for 3 minutes to provide Form 2 of Compound I.

Example 3: Preparation of Form 3 of Compound I

About 15 mg of Form J of Compound I was heated to 80° C. during a Variable Temperature Powder X-ray Diffraction (VT-XRPD) experiment and then cooled at ambient condition for about 3 hours to provide Form 3 of Compound I.

Example 4: Preparation of Form 4 of Compound I

About 15 mg of Form J of Compound I was heated to 60° C. during a Variable Temperature Powder X-ray Diffraction (VT-XRPD) experiment to provide Form 4 of Compound I.

Example 5: Preparation of Form a of Compound I 100 mg of amorphous Compound I was stirred in a mixture of benzyl alcohol (BnOH) and toluene (20:80, v/v) with temperature cycling between 5° C. and 50° C. using a heating/cooling rate of 0.1° C./min. After repeating about 4 to 15 cycles, wet cake was collected by filtration to provide Form A of Compound I. The wet cake contains about 23.1% BnOH by weight (1.5 equiv.) and 0.5% toluene by weight (0.04 equiv.) by 41-NMR.

Example 6: Preparation of Form B of Compound I 100 mg of amorphous Compound I was stirred in anisole with temperature cycling between 5° C. and 50° C. using a heating/cooling rate of 0.1° C./min. After repeating about 4 to 15 cycles, a wet cake was collected by filtration to provide Form B of Compound I. The wet cake contains 13.4% anisole by weight (0.8 equiv.) by $^1$H-NMR.

Example 7: Preparation of Form C of Compound I

About 30 mg of amorphous Compound I was dissolved in anisole. The resulting solution was filtered through a 0.45 μm membrane filter. The resulting clear solution was slowly evaporated under ambient conditions to provide Form C of Compound I. The wet cake contains about 60.7% anisole by weight (7.7 equiv.) by $^1$H NMR.

Example 8: Preparation of Form D of Compound I 10 g of amorphous Compound I was dissolved in 100 ml of EtOAc. Solvent exchange was performed to replace EtOAc with toluene under vacuum to a final volume of about 30-40 ml at no more than 50° C. Additional toluene (50 mL) was added, and the slurry was stirred at 50° C. for 2 hours. The suspension was cooled down to 20° C. for over 1-2 hours and then stirred for 10 hours at 20° C. (1525° C.). The suspension was filtered and rinsed with toluene (20 mL), and then dried to provide Form D of Compound I.

Example 9: Preparation of Form E of Compound I

About 200 mg of Form D of Compound I was added into a 2-mL glass vial. 1.2 mL of DMSO/water (1:1, v/v) was added into the vial. The mixture was stirred at 25° C. for about 5 minutes to obtain a suspension. About 10 mg of Form E seeds was added to the suspension. The suspension was stirred with temperature cycling between 5° C. and 50° C. using a heating/cooling rate of 0.1° C./min for 20 cycles. The resulting suspensions was filtered through a 0.45 μm membrane filter by centrifugation. Wet cake was collected to provide Form E of Compound I.

Example 10: Preparation of Form F of Compound I

About 50 mg of Form D of Compound I was stirred in 0.1-0.2 mL of PEG/water (1:1, v/v) with temperature cycling between 5° C. and 50° C. using a heating/cooling rate of 0.1° C./min for at least 10 cycles. The resulting suspension was filtered through a 0.45 μm membrane filter by centrifugation at 14,000 rpm. The wet cake was collected to provide Form F of Compound I.

Example 11: Preparation of Form G of Compound I

About 200 mg of Form D of Compound I was added into a 2-mL glass vial. 0.4 mL of MEK/heptane (1:1, v/v) was added to the vial. The mixture was stirred at 25° C. for about 5 minutes to obtain a suspension. About 10 mg of Form G seeds was added into the suspension. The suspension was stirred with temperature cycling between 5° C. and 50° C. using a heating/cooling rate of 0.1° C./min for 10 cycles. Obtained suspensions were filtered through a 0.45 μm membrane filter by centrifugation at 14,000 rpm. Wet cake was collected to provide Form G of Compound I.

Example 12: Preparation of Form H of Compound I

About 200 mg of Form D of Compound I was added into a 2-mL glass vial. 0.4 mL of IPA/water (1:1, v/v) was added into the vial. The resulting mixture was stirred at 25° C. for about 5 minutes to obtain a suspension. About 10 mg of Form H seeds was added into above suspension. The suspension was stirred at 25° C. for about 10 days. Solids were collected by centrifugation and then dried at 50° C. under vacuum for about 1 hour. About 180 mg of Form H of Compound I was obtained as an off-white solid in 90% yield.

Example 13: Preparation of Form H1 of Compound I

About 10 mg of Form H of Compound I was stored at 4° C. for 6 months to provide Form H1 of Compound I.

Example 14: Preparation of Form J of Compound I

About 130 mg Form 1 of Compound I was dissolved in 0.3 mL of THF at about 22-25° C. Obtained solution was filtered through a 0.45 μm membrane filter. Form J seeds were added into obtained clear solution followed by adding 0.4 mL of heptane slowly to form a suspension. Solids were collected by centrifugation filtration through a 0.45 μm membrane filter at 14,000 rpm to provide Form J of Compound I.

ABBREVIATIONS

DSC: Differential Scanning calorimetry
DVS: Dynamic Vapor Sorption
FT-IR: Fourier-Transform Infrared
RH: Relative Humidity
PEG: Polyethylene glycol
XRPD: X-ray powder diffraction
$^1$H-NMR: proton nuclear magnetic resonance
T3P: propanephosphonic acid anhydride
TFAA: trifluoroacetic anhydride
$P_2O_5$: phosphorus pentoxide
MEK: methyl ethyl ketone
EtOH: ethanol
$H_2O$: water
DMSO: dimethyl sulfoxide
EtOAc: ethyl acetate
HCl: hydrogen chloride
ACN: acetonitrile While this invention has been particularly shown and described with references to preferred embodiments thereof, it will be understood by those skilled in the art that various changes in form and details may be made therein without departing from the scope of the invention encompassed by the appended claims.

What is claimed is:

1. A crystalline Form 1 of Compound I,

Compound I

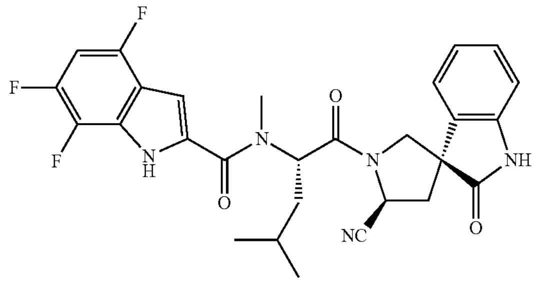

wherein said crystalline form is characterized by an x-ray powder diffraction pattern having characteristic peaks at values of two theta (° 2θ) of 6.9, 8.3, 10.8, 11.9, 13.2, 13.7, 14.5, 15.4, 16.1, 18.2, 19.2, 20.0, 20.6, 21.7, 22.3, 23.9, 24.8, 25.2, 25.3, 26.1, 26.7, 27.6, 27.9, 28.9, 29.3, 30.1, 31.3, 31.3, 31.7, 32.5, 32.9, 34.7, 35.0, 35.8, 36.1, 36.8, 37.1, 37.8, 38.8, and 39.7.

2. The crystalline form of claim 1, further characterized by a differential Scanning Calorimeter thermogram having an Endotherm at 251° C. with an onset temperature at 250° C.

3. The crystalline form of claim 1, wherein said crystalline form is characterized by a differential Scanning Calorimeter thermogram having an Endotherm at 175° C. with an onset temperature at 175° C. and endotherm at 251° C. with an onset temperature at 250° C.

4. A crystalline Form 2 of Compound I,

Compound I

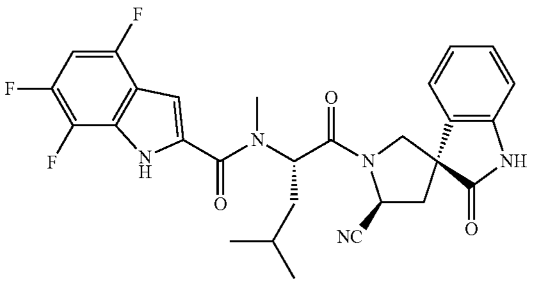

wherein said crystalline form is characterized by an x-ray powder diffraction (XRPD) pattern having characteristic peaks of two theta (° 2θ) of 6.9, 10.8, 11.9, 13.7, 14.5, 16.1, 18.1, 20.0, 20.6, 21.7, 22.3, 23.9, 24.8, 25.2, 26.1, 26.7, 27.9, 28.8, 29.2, 30.1, 31.3, 32.8, 34.3, 34.7, 35.77, 36.1, 37.1, and 39.9.

5. The crystalline form of claim 4, wherein said crystalline form is further characterized by a differential Scanning Calorimeter thermogram having an Endotherm at 175° C. with an onset temperature at 175° C. and endotherm at 251° C. with an onset temperature at 250° C.

6. A crystalline Form 3 of Compound I,

Compound I

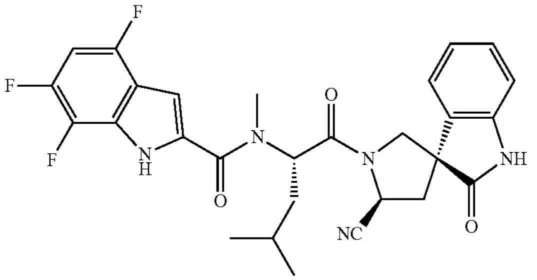

wherein said crystalline form is characterized by an X-ray powder diffraction (XRPD) pattern having characteristic peaks at values of two theta (° 2θ) of 7.1, 8.7, 8.9, 11.0, 11.7, 13.1, 14.1, 15.2, 15.6, 16.2, 17.1, 17.5, 18.0, 19.2, 19.6, 20.4, 20.7, 21.9, 22.6, 23.5, 23.8, 24.7, 25.8, 26.3, 27.0, 28.1, 28.6, 29.7, 30.4, 31.3, 31.8, 32.3, 32.8, 33.3, 34.7, 35.6, 36.1, 36.5, 37.1, 37.9, and 38.2.

7. A crystalline Form 4 of Compound I,

Compound I

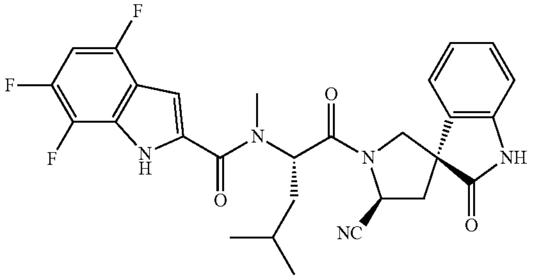

wherein said crystalline form is characterized by an X-ray powder diffraction (XRPD) pattern having characteristic peaks at values of two theta (° 2θ) of 4.4, 5.1, 7.1, 7.5, 8.5, 8.9, 9.8, 10.1, 10.3, 11.0, 11.7, 12.5, 13.1, 13.8, 14.1, 14.6, 14.8, 15.4, 15.8, 16.0, 16.9, 17.5, 17.9, 18.5, 19.2, 19.7, 20.1, 21.0, 21.8, 22.5, 23.4, 24.2, 24.9, 25.1, 26.2, 26.5, 27.8, 28.5, 29.4, and 31.0.

8. A composition comprising a crystalline form according to claim 1.

9. A process for making a pharmaceutical composition comprising Compound I, comprising dissolving the crystalline form according to claim 1 in a solvent.

10. A process for the preparation of the crystalline Form 1 of claim 1, said process comprising the steps of:

1) preparing a solution of Compound I by dehydrating (3R,5'S)-1'-(N-methyl-N-(4,6,7-trifluoro-1H-indole-2-carbonyl)-L-leucyl)-2-oxospiro[indoline-3,3'-pyrrolidine]-5'-carboxamide (Compound n) in the presence of a suitable dehydration reagent or reagents, a suitable base, and a suitable solvent, thereby producing a solution of Compound 1;
2) concentrating the solution of Compound I from step 1 at a temperature from about 20° C. to about 80° C., to a solvent/Compound n ratio by volume (milliliter)/weight (gram) from about 2:1 to about 6:1;
3) optionally adding about 0.0001X (X=weight of Compound n in step 1) to about 0.1X of Form 1 of Compound I by weight to the concentrated solution from step 2, to induce crystallization of Form 1 of Compound I;
4) exchanging the solvent to a suitable solvent to a solvent/Compound n ratio by volume (milliliter)/weight (gram) from about 6:1 to about 10:1, at a temperature from about 20° C. to about 80° C., and the said suitable solvent is selected from anisole, toluene, xylene, ethyl acetate, isopropyl acetate, and mixtures of two or more thereof;
5) cooling the solution produced in step (4) to a temperature of about 0° C. to about 50° C., thereby producing Form 1 of Compound I; and
6) Filtering the product of step 5) to provide Form 1 of Compound I.

11. The process as claimed in claim 9, wherein the solvent is selected from anisole, toluene, xylene, ethyl acetate, isopropyl acetate, and mixtures of two or more thereof.

12. A process for the preparation of the crystalline Form 1 of claim 1, said process comprising the steps of:

I. adding Compound I to a first solvent thereby producing a solution; wherein the Compound I used to produce the solution is a solid form of Compound I or a mixture of two or more solid forms;
II. removing a portion of the first solvent from the solution, and then adding more of the first solvent;
III. repeating removing a portion of the first solvent from the solution and adding more of the first solvent until a solution of Compound I is produced with residual solvent controlled at no greater than a predetermined value;
IV. adding a second solvent to the solution to precipitate the Form 1 of Compound I; and
V. isolating the Form 1 of Compound I by filtration.

13. The process as claimed in claim 12, wherein the first solvent is EtOH, isopropanol, acetone, ethyl acetate, isopropyl acetate, or methyl tert-butyl ether.

14. The method of claim 12, wherein the second solvent water or n-heptane.

* * * * *